(12) United States Patent
Fujihara et al.

(10) Patent No.: US 8,940,879 B2
(45) Date of Patent: *Jan. 27, 2015

(54) FUNCTIONAL MOLECULE, FUNCTIONAL MOLECULE SYNTHESIZING AMIDITE AND TARGET SUBSTANCE ANALYSIS METHOD

(75) Inventors: Tsuyoshi Fujihara, Kawasaki (JP); Shozo Fujita, Kawasaki (JP)

(73) Assignee: Apta Biosciences Ltd., Ledbury (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/599,552

(22) Filed: Aug. 30, 2012

(65) Prior Publication Data

US 2013/0017973 A1   Jan. 17, 2013

Related U.S. Application Data

(62) Division of application No. 12/049,825, filed on Mar. 17, 2008, now Pat. No. 8,288,516.

(30) Foreign Application Priority Data

Mar. 16, 2007   (JP) .................................. 2007-069378

(51) Int. Cl.
*C07H 19/00*   (2006.01)
*C12Q 1/68*   (2006.01)

(52) U.S. Cl.
USPC ........................................................ 536/4.1

(58) Field of Classification Search
USPC ........................................... 536/4.1; 435/6.1
See application file for complete search history.

(56) References Cited

U.S. PATENT DOCUMENTS

| | | | |
|---|---|---|---|
| 5,459,255 A * | 10/1995 | Cook et al. | ................. 536/27.13 |
| 6,664,079 B2 | 12/2003 | Ju et al. | |
| 7,057,026 B2 | 6/2006 | Barnes et al. | |
| 7,723,495 B2 * | 5/2010 | Fujihara et al. | ............. 536/22.1 |
| 7,910,726 B2 * | 3/2011 | Fujihara | ....................... 536/26.7 |
| 2008/0167459 A1 | 7/2008 | Fujihara et al. | |

FOREIGN PATENT DOCUMENTS

WO   03/078623 A1   9/2003

OTHER PUBLICATIONS

Japanese Office Action mailed Jul. 17, 2012, issued in corresponding Japanese Patent Application No. 2007-069378.

* cited by examiner

*Primary Examiner* — Jezia Riley
(74) *Attorney, Agent, or Firm* — Westerman, Hattori, Daniels & Adrian, LLP

(57) ABSTRACT

To provide a functional molecule including a modified nucleotide unit having a substituent introduced to a base thereof, wherein the substituent is removably introduced to the base; a functional molecule synthesizing amidite that has a substituent removably introduced to its base and that is used for the manufacture of the functional molecule; and a target substance analysis method including: preparing a random pool of functional molecules using a functional molecule synthesizing amidite; screening a functional molecule having affinity for a target substance from the random pool; amplifying the functional molecules having affinity for the target substance, wherein the method further comprises, prior to the amplification step, removing a substituent from the functional molecule having affinity for the target substance.

5 Claims, 49 Drawing Sheets

1. 25bp ladder
2. $10^6$ start — Not treated with ammonia
3. $10^4$ start
4. $10^3$ start
5. $10^2$ start
6. $10^1$ start — Treated with ammonia
7. $10^0$ start
8. $10^{-1}$ start
9. 50bp ladder 10% acrylamide gel

FIG. 49

Codes appeared are only AT, AC, AA, TA, and GC

```
                        SEQUENCE LISTING

<160> NUMBER OF SEQ ID NOS: 16

<210> SEQ ID NO 1
<211> LENGTH: 40
<212> TYPE: DNA
<213> ORGANISM: Artificial Sequence
<220> FEATURE:
<223> OTHER INFORMATION: Chemically Synthesized

<400> SEQUENCE: 1
gaaggtgaag gtcggctgaa gctaccatca tcaccatctt                           40

<210> SEQ ID NO 2
<211> LENGTH: 10
<212> TYPE: DNA
<213> ORGANISM: Artificial Sequence
<220> FEATURE:
<223> OTHER INFORMATION: Chemically Synthesized

<400> SEQUENCE: 2
cttcaccttc                                                            10

<210> SEQ ID NO 3
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 3
gaaggtgaag gtcggagtca acggctggaa atcccatcac catcttc                   47

<210> SEQ ID NO 4
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 4
ttatcaacaa aatactccaa ttgactgctt tcgaaagatc ccaacgaaaa g              51

<210> SEQ ID NO 5
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 5
ttatcaacaa aatactccaa ttg                                             23

<210> SEQ ID NO 6
<211> LENGTH: 19
<212> TYPE: DNA
<213> ORGANISM: Artificial Sequence
```

```
<220> FEATURE:
<223> OTHER INFORMATION: Chemically Synthesized

<400> SEQUENCE: 6
cttttcgttg ggatctttc                                                     19

<210> SEQ ID NO 7
<211> LENGTH: 117
<212> TYPE: DNA
<213> ORGANISM: Artificial Sequence
<220> FEATURE:
<223> OTHER INFORMATION: Chemically Synthesized

<400> SEQUENCE: 7
gaaggtgaag gtcggagtca acgacgcgat gcctaatggc aacgcaacgc gcggcgccgc        60
tacaacgcgc gacacgatgc cgcgccacaa gaagccggaa atcccatcac catcttc          117

<210> SEQ ID NO 8
<211> LENGTH: 117
<212> TYPE: DNA
<213> ORGANISM: Artificial Sequence
<220> FEATURE:
<223> OTHER INFORMATION: Chemically Synthesized

<400> SEQUENCE: 8
gaaggtgaag gtcggagtca acgaatagta atgaaatggc aacaatagac tagactaggc        60
tgcgcgatta gaataggcgc caagcggcac ggcaagggaa atcccatcac catcttc          117

<210> SEQ ID NO 9
<211> LENGTH: 117
<212> TYPE: DNA
<213> ORGANISM: Artificial Sequence
<220> FEATURE:
<223> OTHER INFORMATION: Chemically Synthesized

<400> SEQUENCE: 9
gaaggtgaag gtcggagtca acgacgccgc gcctaatgaa accgcaagat acgtaaaggc        60
tgcaccatac gtaacctagc cgcaccgcac gtaatcggaa atcccatcac catcttc          117

<210> SEQ ID NO 10
<211> LENGTH: 117
<212> TYPE: DNA
<213> ORGANISM: Artificial Sequence
<220> FEATURE:
<223> OTHER INFORMATION: Chemically Synthesized

<400> SEQUENCE: 10
gaaggtgaag gtcggagtca acgatgcgaa tagacgcggc tacaagcgat aagatatcgc        60
tgcaagatta cgcgccatgc gtaacggcaa cgcatgggaa atcccatcac catcttc          117

<210> SEQ ID NO 11
<211> LENGTH: 117
<212> TYPE: DNA
<213> ORGANISM: Artificial Sequence
<220> FEATURE:
<223> OTHER INFORMATION: Chemically Synthesized

<400> SEQUENCE: 11
gaaggtgaag gtcggagtca acgactacat tagtaacgta acgacgccat aagattaggc        60
ttaacggcaa gtaaacatta gattaggcaa gacaagggaa atcccatcac catcttc          117

<210> SEQ ID NO 12
```

```
<211> LENGTH: 117
<212> TYPE: DNA
<213> ORGANISM: Artificial Sequence
<220> FEATURE:
<223> OTHER INFORMATION: Chemically Synthesized

<400> SEQUENCE: 12
gaaggtgaag gtcggagtca acgactaggc aacgcaagta gcggcatgat gcggcaccgc        60
ttaacgatac gtaatgaata gattaggcgc ggcatcggaa atcccatcac catcttc          117

<210> SEQ ID NO 13
<211> LENGTH: 117
<212> TYPE: DNA
<213> ORGANISM: Artificial Sequence
<220> FEATURE:
<223> OTHER INFORMATION: Chemically Synthesized

<400> SEQUENCE: 13
gaaggtgaag gtcggagtca acggcatgta gcggcatgaa gccacaccac gccgcgccgc        60
taatagtaaa gtatacgcta gtaaaggcat cgcgcgggaa atcccatcac catcttc          117

<210> SEQ ID NO 14
<211> LENGTH: 117
<212> TYPE: DNA
<213> ORGANISM: Artificial Sequence
<220> FEATURE:
<223> OTHER INFORMATION: Chemically Synthesized

<400> SEQUENCE: 14
gaaggtgaag gtcggagtca acgtatacac gccaagcgta taggctacgc aacaataggc        60
taatagtata gtaacgacat cactacaata cactagggaa atcccatcac catcttc          117

<210> SEQ ID NO 15
<211> LENGTH: 117
<212> TYPE: DNA
<213> ORGANISM: Artificial Sequence
<220> FEATURE:
<223> OTHER INFORMATION: Chemically Synthesized

<400> SEQUENCE: 15
gaaggtgaag gtcggagtca acgatgccac gcgaaatcgc atggcatgta accacaaggc        60
taaacgatgc ggcgcctagc ggctactaat ctagcgggaa atcccatcac catcttc          117

<210> SEQ ID NO 16
<211> LENGTH: 117
<212> TYPE: DNA
<213> ORGANISM: Artificial Sequence
<220> FEATURE:
<223> OTHER INFORMATION: Chemically Synthesized

<400> SEQUENCE: 16
gaaggtgaag gtcggagtca acggcaagat aactagcgac gcggctagaa acgacgccgc        60
tgctagtaaa gacgccaagc gataccgcat ggctagggaa atcccatcac catcttc          117
```

US 8,940,879 B2

FUNCTIONAL MOLECULE, FUNCTIONAL MOLECULE SYNTHESIZING AMIDITE AND TARGET SUBSTANCE ANALYSIS METHOD

CROSS-REFERENCE TO RELATED APPLICATIONS

This application is a divisional of U.S. application Ser. No. 12/049,825, filed on Mar. 17, 2008, which is based upon and claims the benefits of priority from Japanese Patent Application No. 2007-069378 filed on Mar. 16, 2007, the entire contents of which are incorporated herein by reference.

BACKGROUND OF THE INVENTION

1. Field of the Invention

The present invention relates to a functional molecule that shows affinity for a target substance and is suitably used in a variety of fields including drugs, drug delivery and biosensors, as well as in controlling of gene expression level, overcoming diseases caused by abnormal genes, elucidation of the function of a protein translated from gene and development of reaction catalysts. More specifically, the present invention related to a functional molecule suitable for the analysis of proteins, a functional molecule synthesizing amidite used for synthesizing the functional molecule, and a target substance analysis method using them.

2. Description of the Related Art

Unraveling of the whole human genome has shifted the focus of interest of scientists and researchers on the analysis of proteins—gene products. It may not be overstating to say that substantial protein analysis can be made possible only when a molecule that shows affinity for a protein of interest has been successfully obtained. A cell, however, contains many different types of proteins, and the amino acid sequence and structure of many of which are still unknown.

The most common technique for obtaining a molecule that shows affinity for a specific protein is to prepare an affinity antibody by utilizing the immune system of animal. However, this technique uses animals and requires a large quantity of proteins, a large number of processes and large costs. Additionally, no affinity antibody may be obtained for specific substances with this technique.

A technique called aptamer method (also referred to as SELEX) that does not rely on any living organism has been proposed to avoid this problem. However, while a molecule obtained by this technique strongly interacts with a specific protein, this technique is not applicable to all proteins. In view of the above-identified circumstances, the inventors of the present invention proposed a modified aptamer method that is established by improving the aptamer method so as to use a modified nucleic acid analogue (see International Publication No. WO2003/078623). However, since the modified aptamer method uses a modified nucleic acid analogue that includes different modified nucleotide units with different substituents, the properties of each of the substituents have to be considered when amplifying a modified nucleic acid analogue showing affinity for a target substance. Thus, it has been difficult to find an excellent PCR condition. Additionally, the above method has a drawback that a modified nucleic acid analogue that tends to be strongly bonded to a target substance is hard to be amplified by PCR. Therefore, there has been a demand to make further improvements on the above method.

BRIEF SUMMARY OF THE INVENTION

According to an aspect of an embodiment, there is a functional molecule including a modified nucleotide unit having a substituent introduced to a base thereof, wherein the substituent is removably introduced to the base.

In another aspect of an embodiment, there is an amidite for manufacturing a functional molecule having the amidite being characterized in that a substituent is removably introduced to the base.

In still another aspect of an embodiment, there is a target substance analysis method including a random pool preparation step of preparing a pool of functional molecules by synthesizing functional molecules using a functional molecule synthesizing amidite, a screening step of screening a functional molecule having affinity for a target substance from the random pool, and an amplification step of amplifying the functional molecule having affinity for the target substance, wherein the method further includes a removal step of removing a substituent of the functional molecules having affinity for the target substance from the functional molecule.

BRIEF DESCRIPTION OF THE SEVERAL VIEWS OF THE DRAWINGS

FIG. 49 is a schematic illustration of part of the sequence obtained as a result of a sequencing operation in Example 3 (Sequence ID No. 7 through Sequence ID No. 16).

DETAILED DESCRIPTION OF THE INVENTION

Functional Molecule

Figure 1:
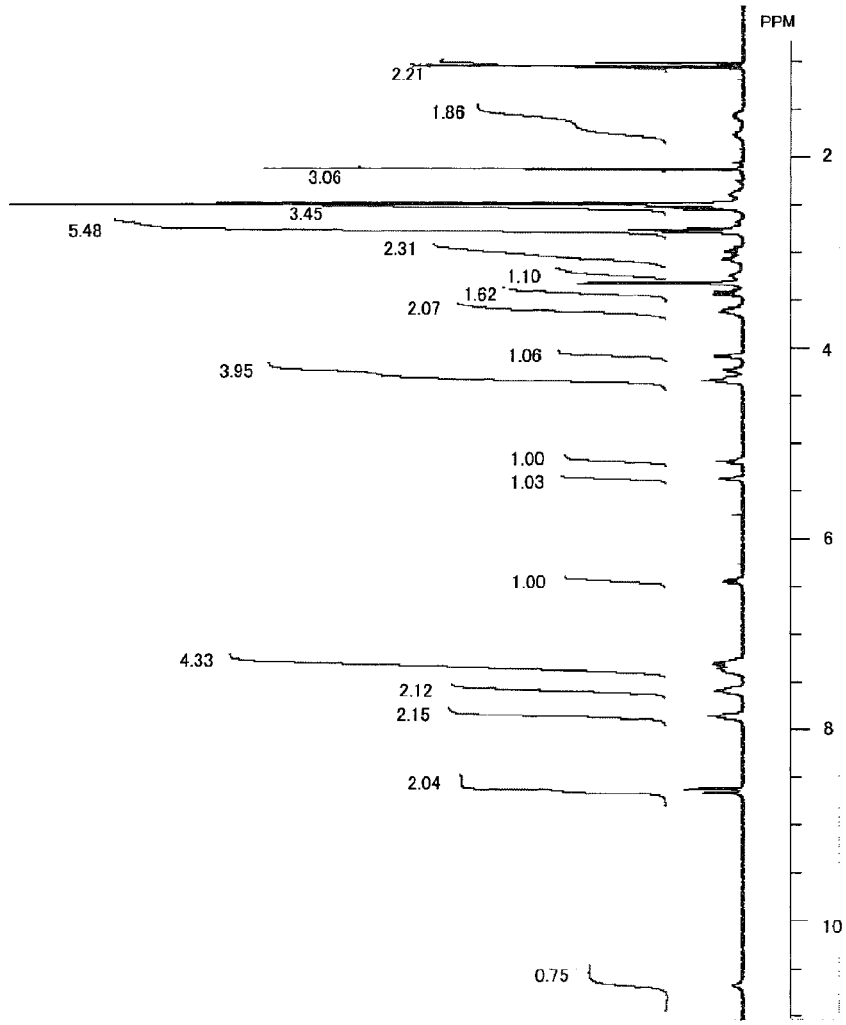
FIG. 1 is a schematic illustration of $^1$H-NMR spectrum of compound IVa of Example 1.
Figure 2:
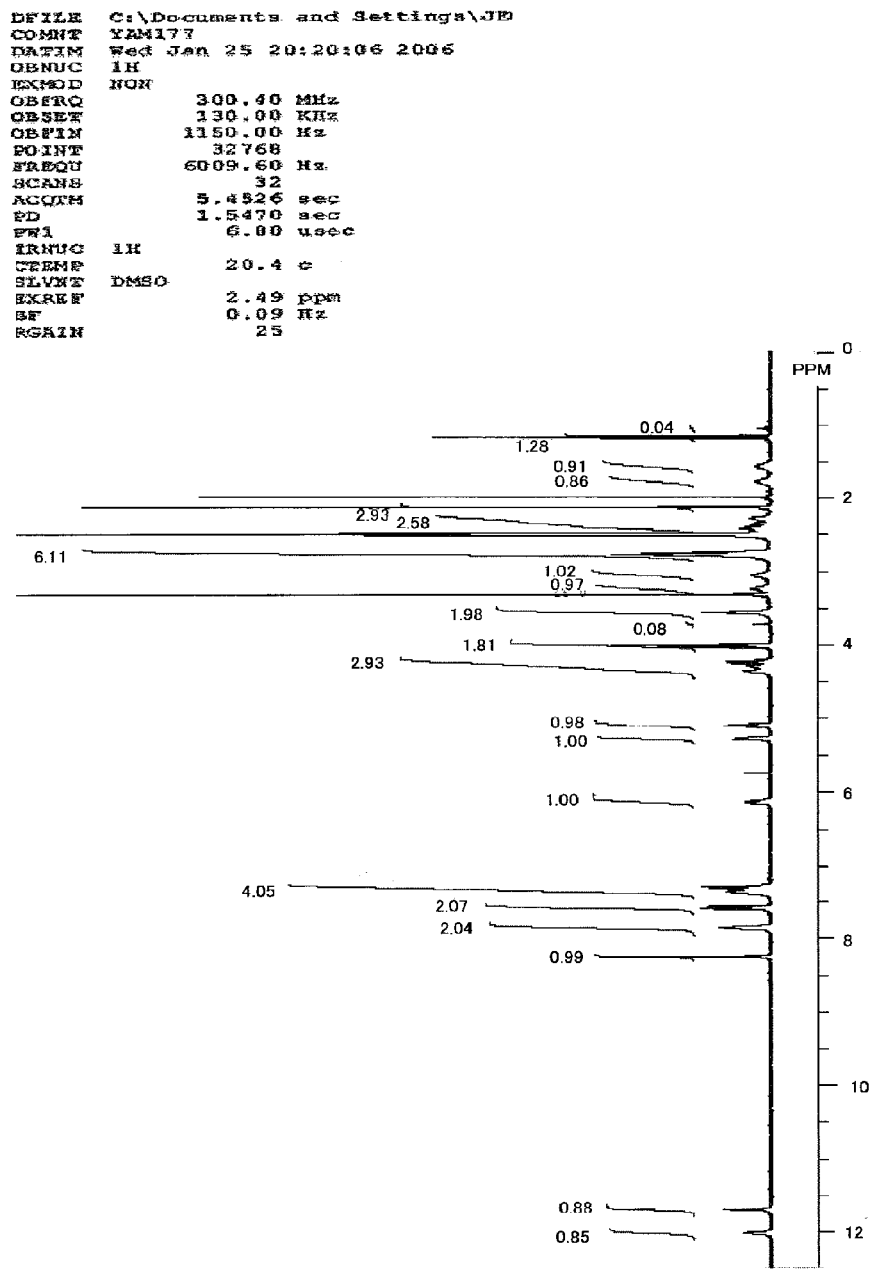
FIG. 2 is a schematic illustration of $^1$H-NMR spectrum of compound IVg of Example 1.
Figure 3:
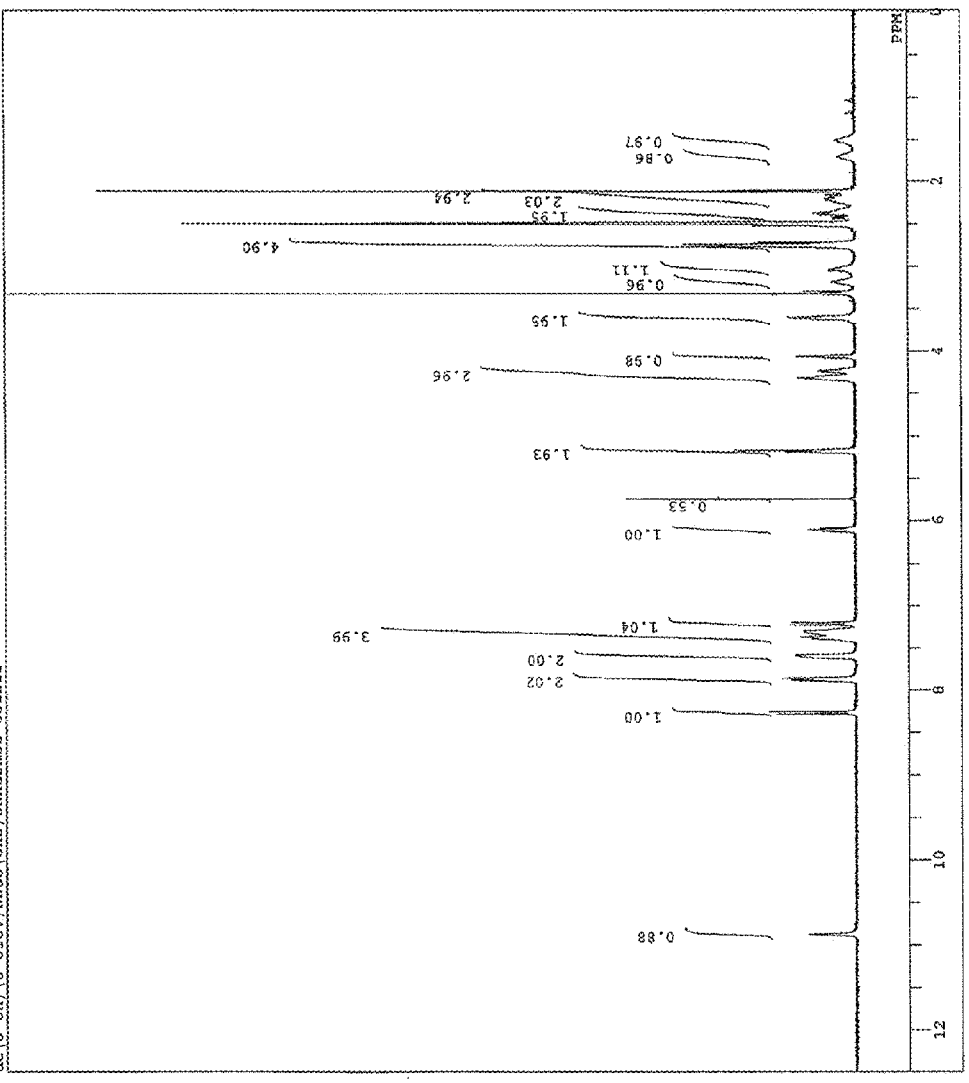
FIG. 3 is a schematic illustration of $^1$H-NMR spectrum of compound IVc of Example 1.
Figure 4:
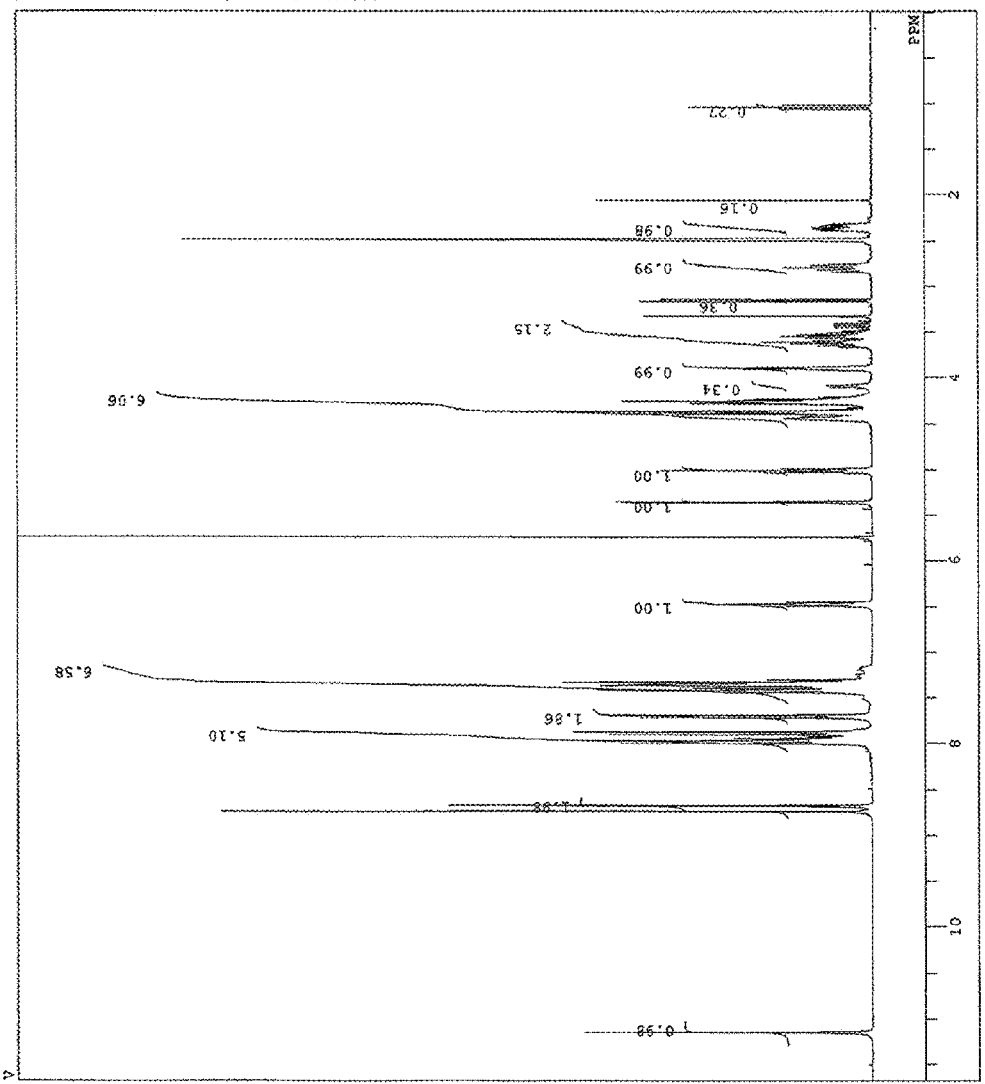
FIG. 4 is a schematic illustration of $^1$H-NMR spectrum of compound V of Example 1.
Figure 5:
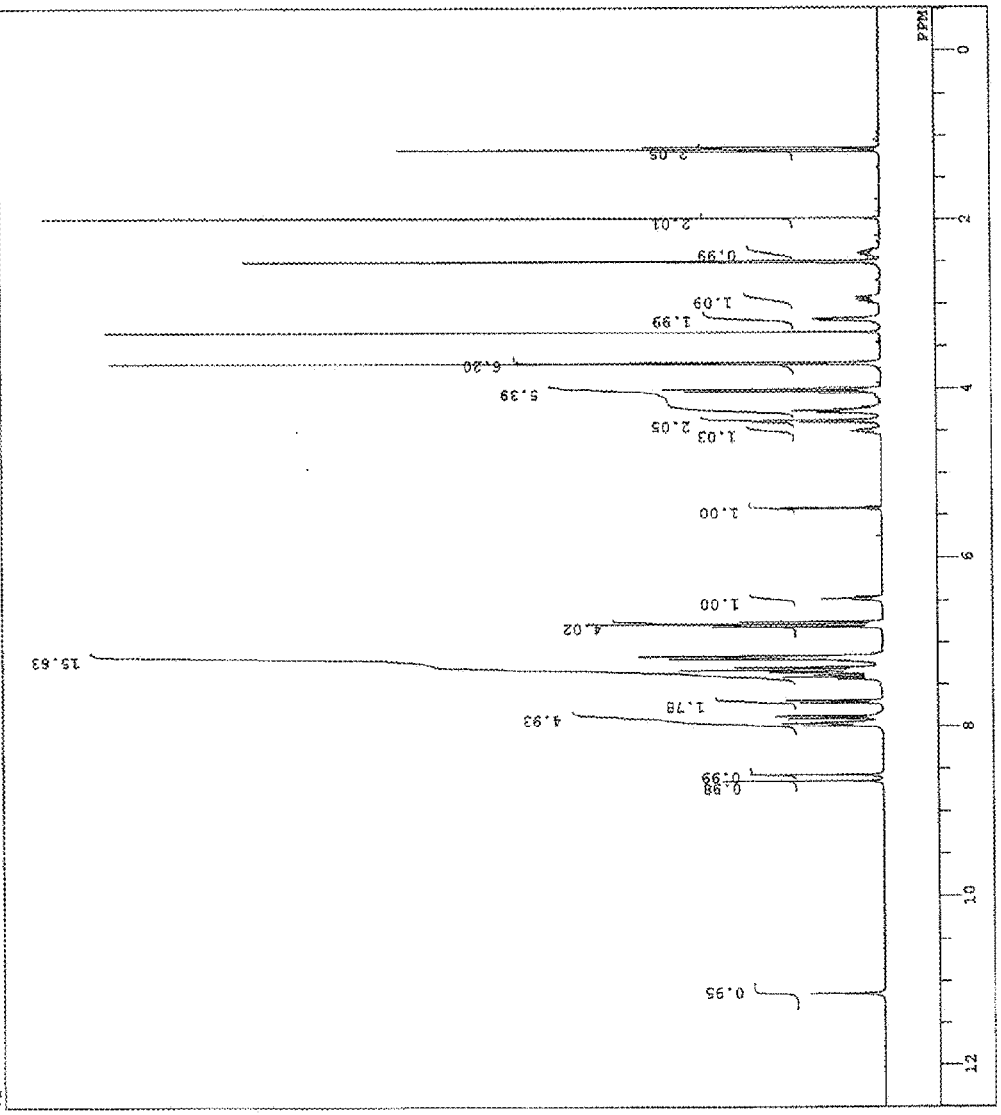
FIG. 5 is a schematic illustration of $^1$H-NMR spectrum of compound VI of Example 1.
Figure 6:
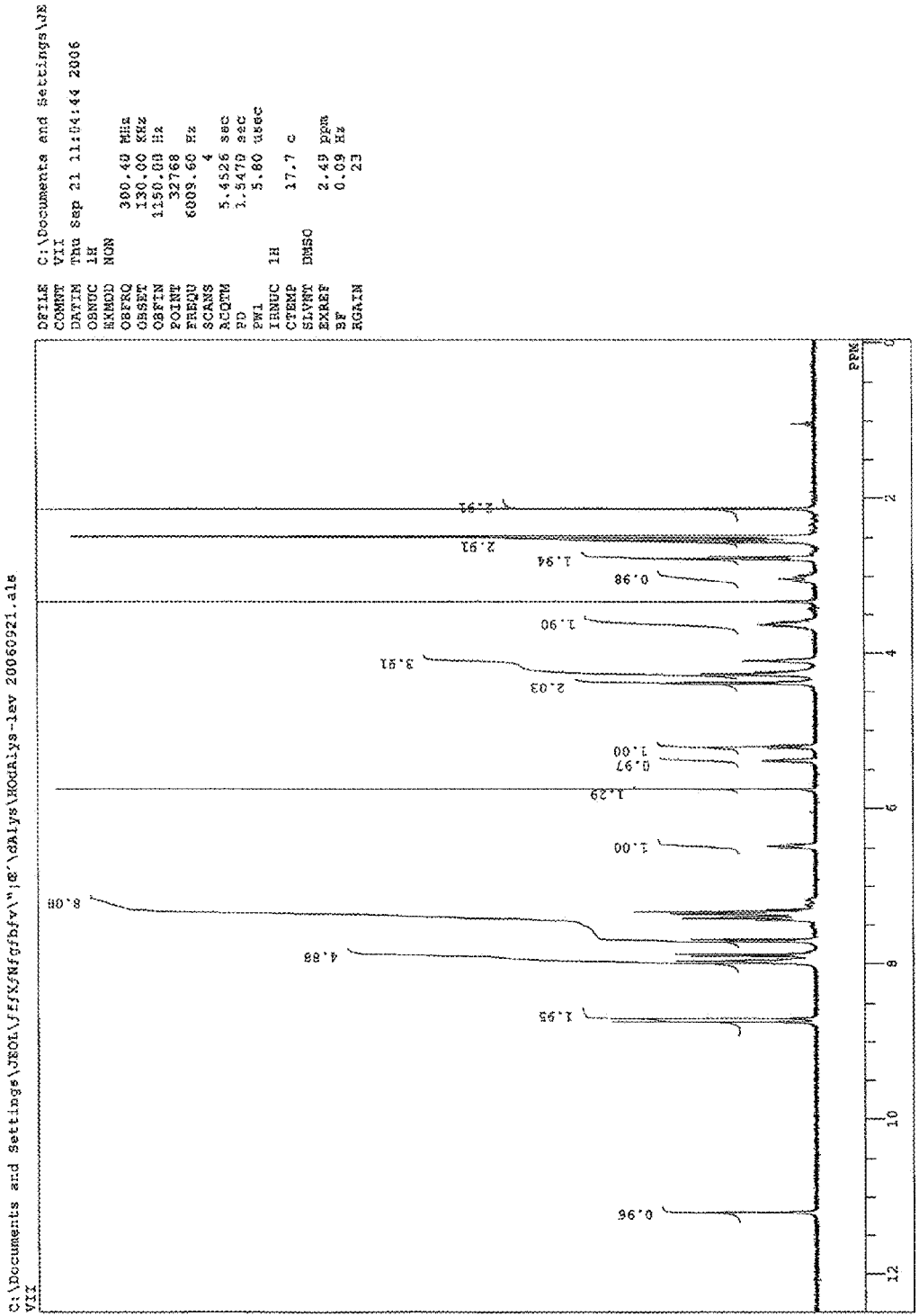
FIG. 6 is a schematic illustration of $^1$H-NMR spectrum of compound VII of Example 1.
Figure 7:
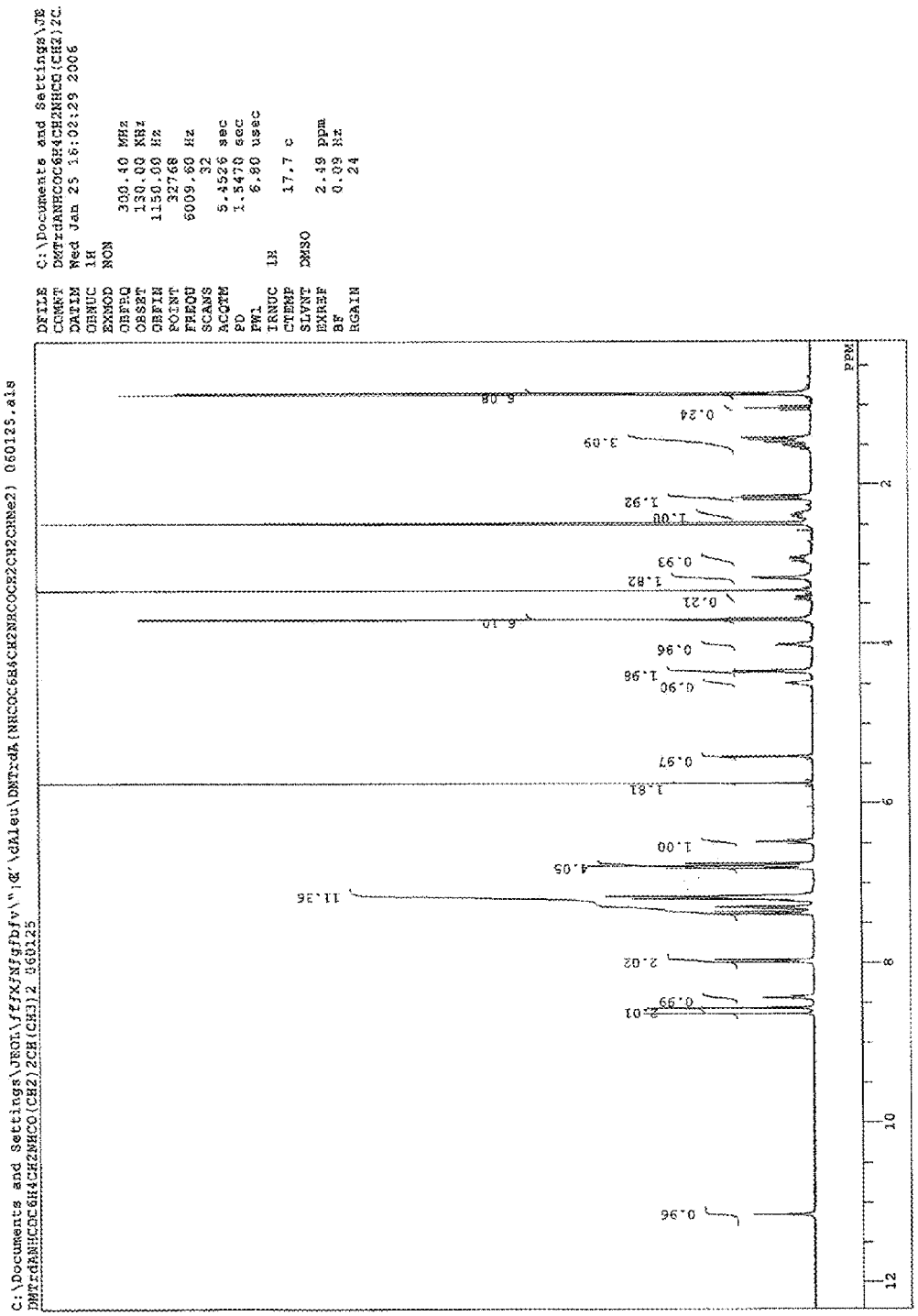
FIG. 7 is a schematic illustration of $^1$H-NMR spectrum of compound $VIII_{Leu}$ of Example 1.
Figure 8:
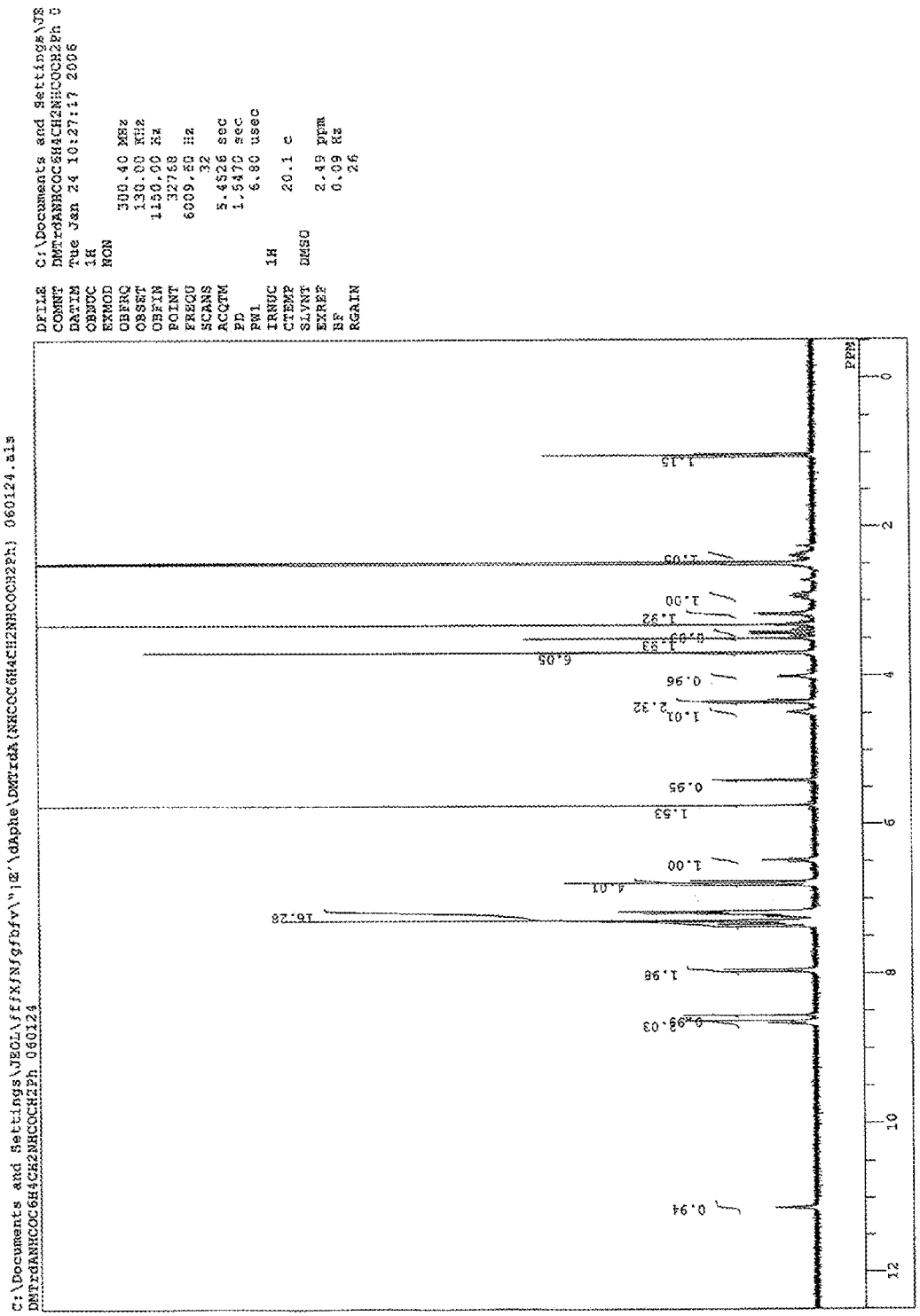
FIG. 8 is a schematic illustration of $^1$H-NMR spectrum of compound $VIII_{Phe}$ of Example 1.
Figure 9:
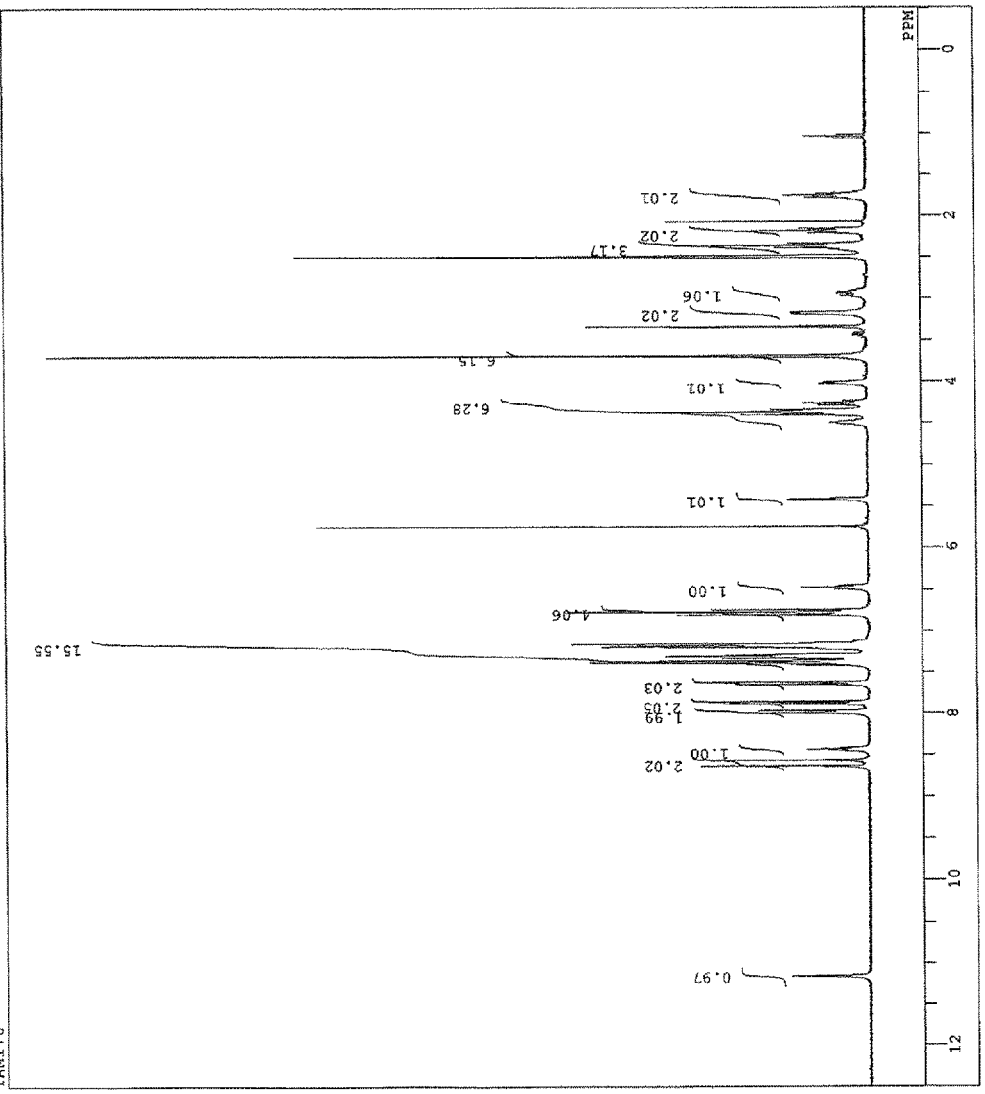
FIG. 9 is a schematic illustration of $^1$H-NMR spectrum of compound $VIII_{Glu}$ of Example 1.
Figure 10:
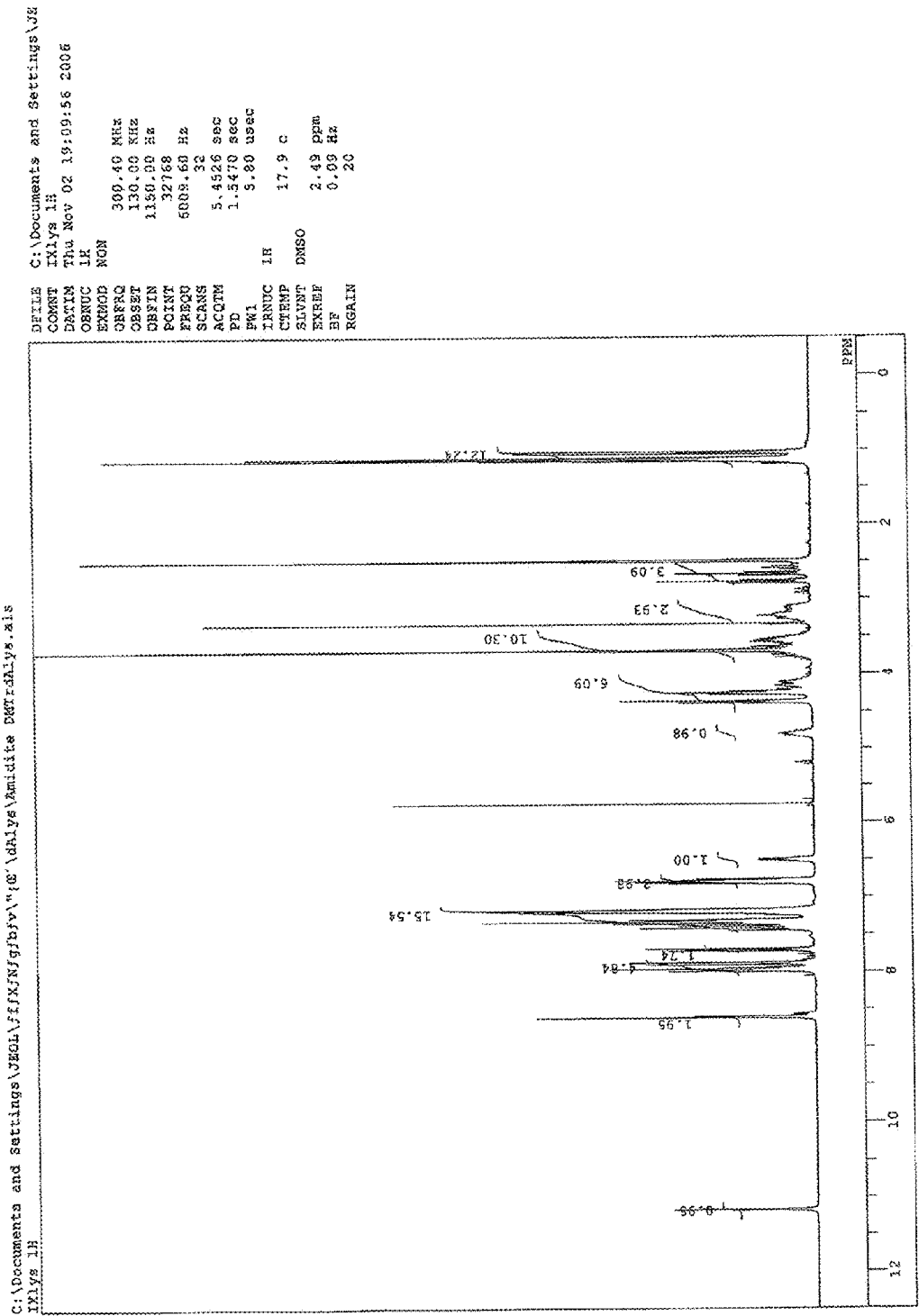
FIG. 10 is a schematic illustration of $^1$H-NMR spectrum of compound $IX_{Lys}$ of Example 1.
Figure 11:
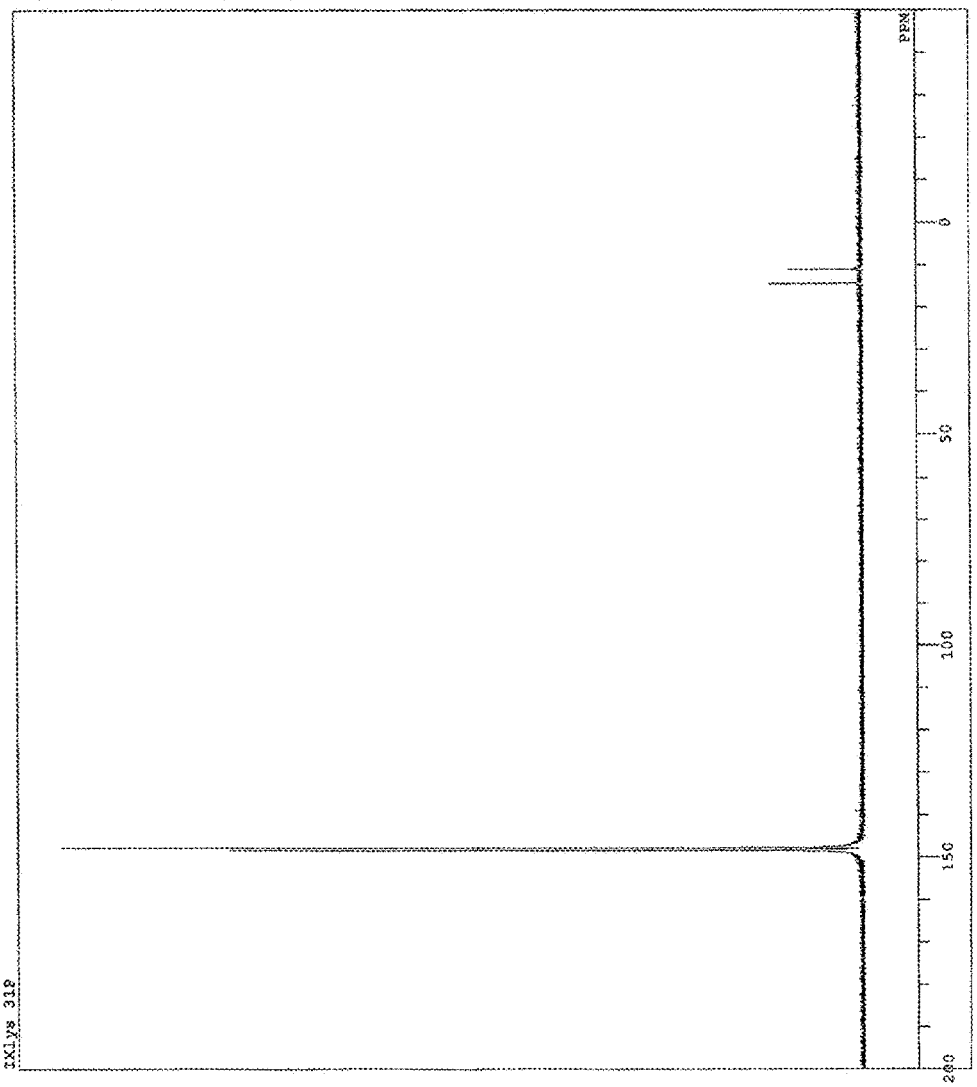
FIG. 11 is a schematic illustration of $^{31}$P-NMR spectrum of compound $IX_{Lys}$ of Example 1.
Figure 12:
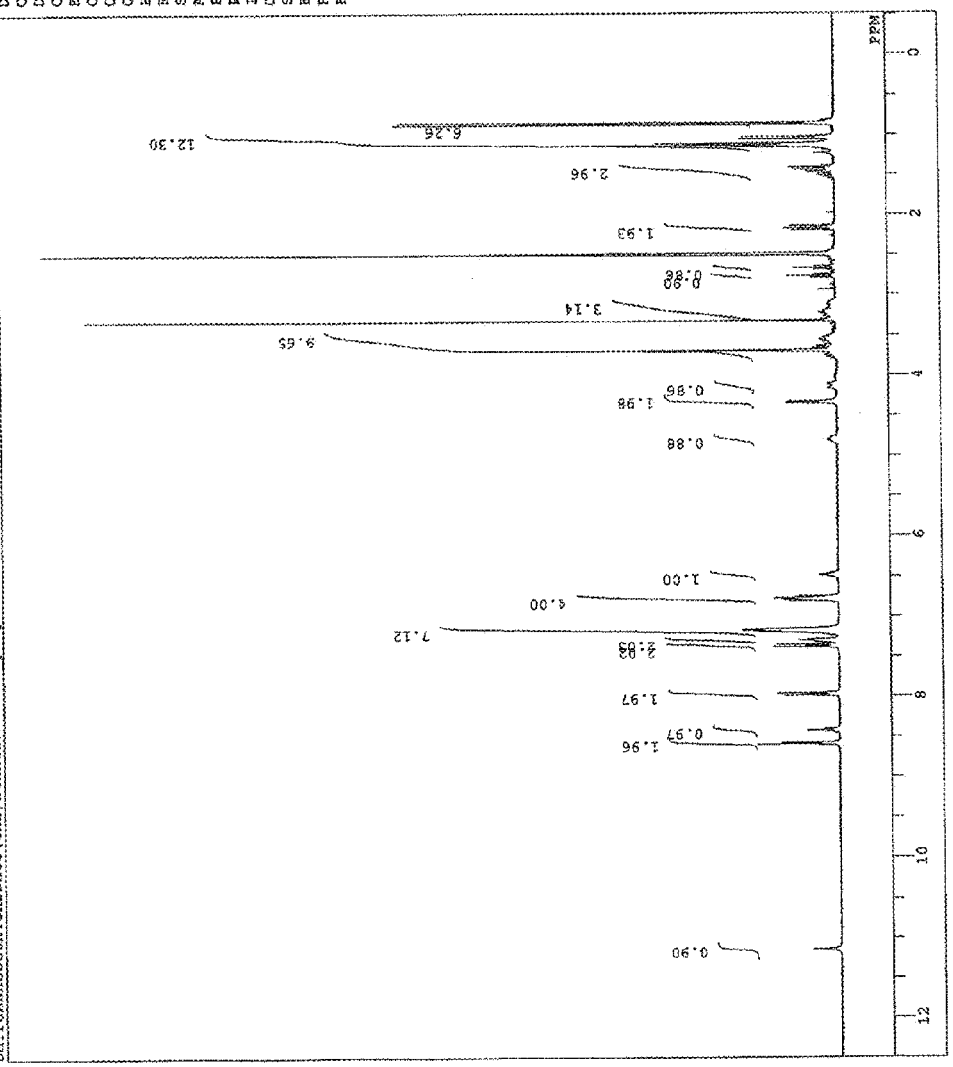
FIG. 12 is a schematic illustration of $^1$H-NMR spectrum of compound $IX_{Leu}$ of Example 1.
Figure 13:
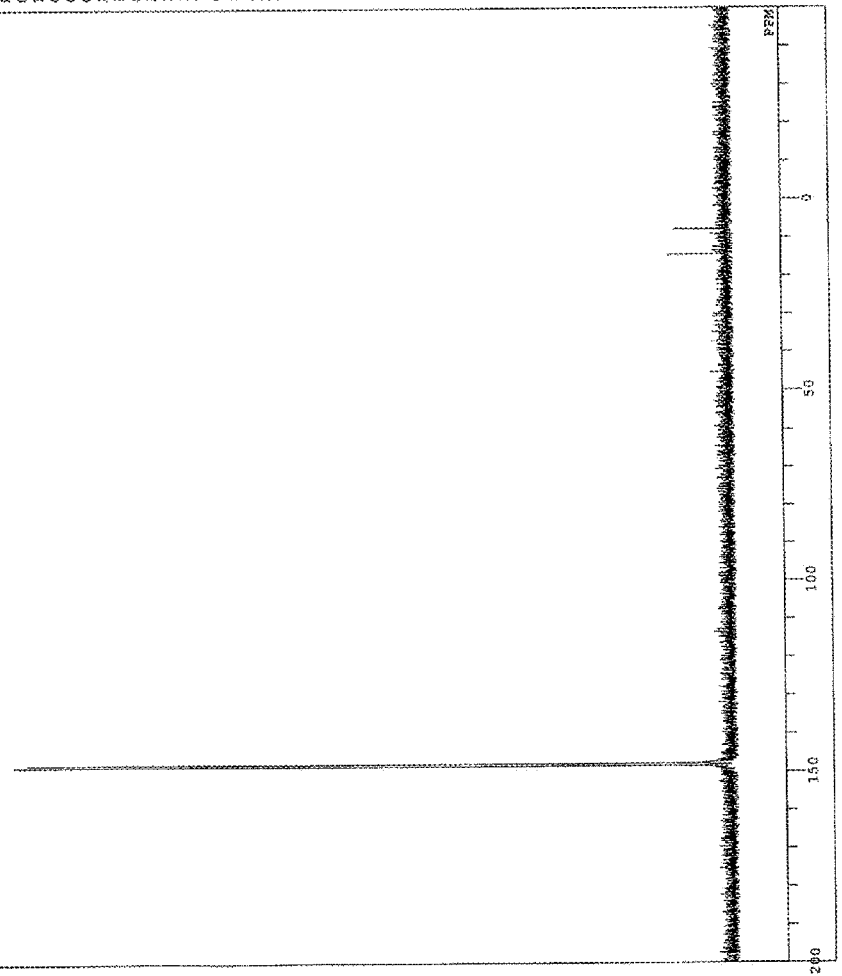
FIG. 13 is a schematic illustration of $^{31}$P-NMR spectrum of compound $IX_{Leu}$ of Example 1.
Figure 14:
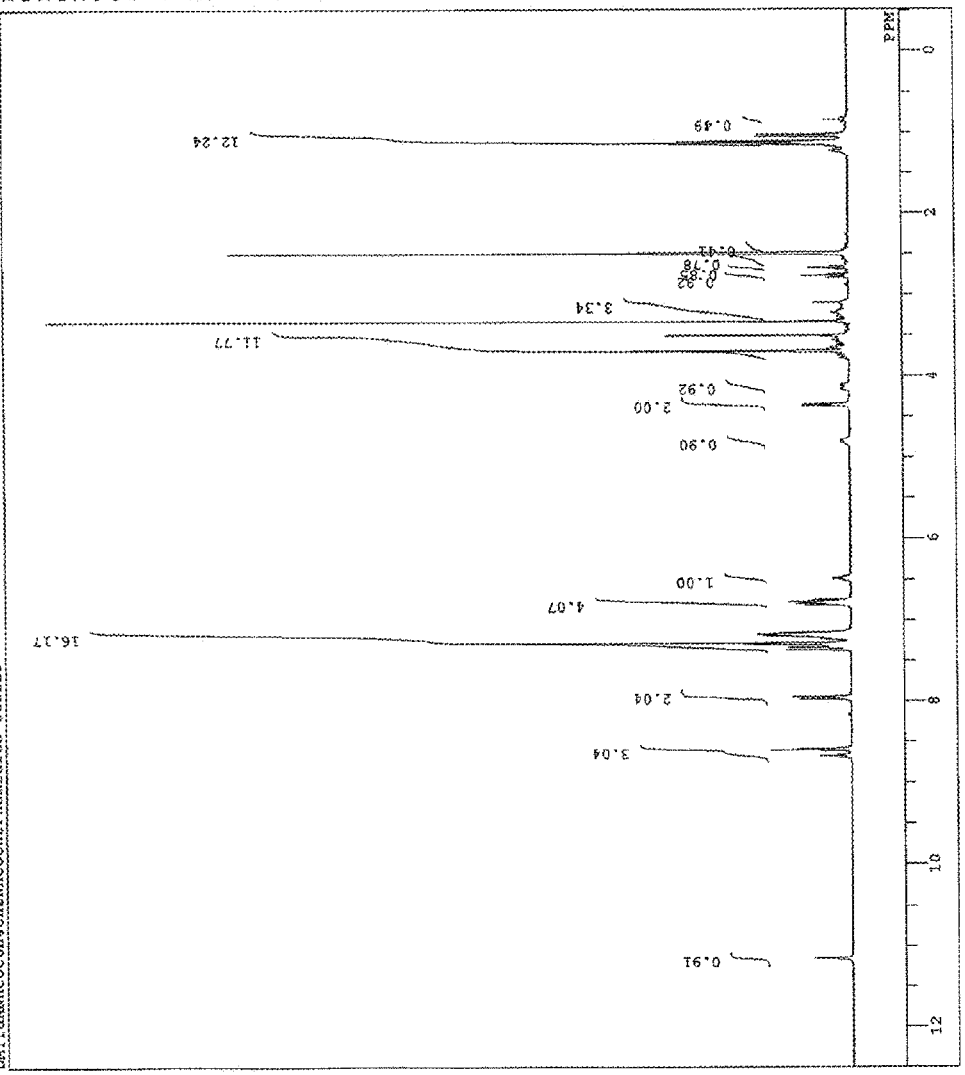
FIG. 14 is a schematic illustration of $^1$H-NMR spectrum of compound $IX_{Phe}$ of Example 1.
Figure 15:
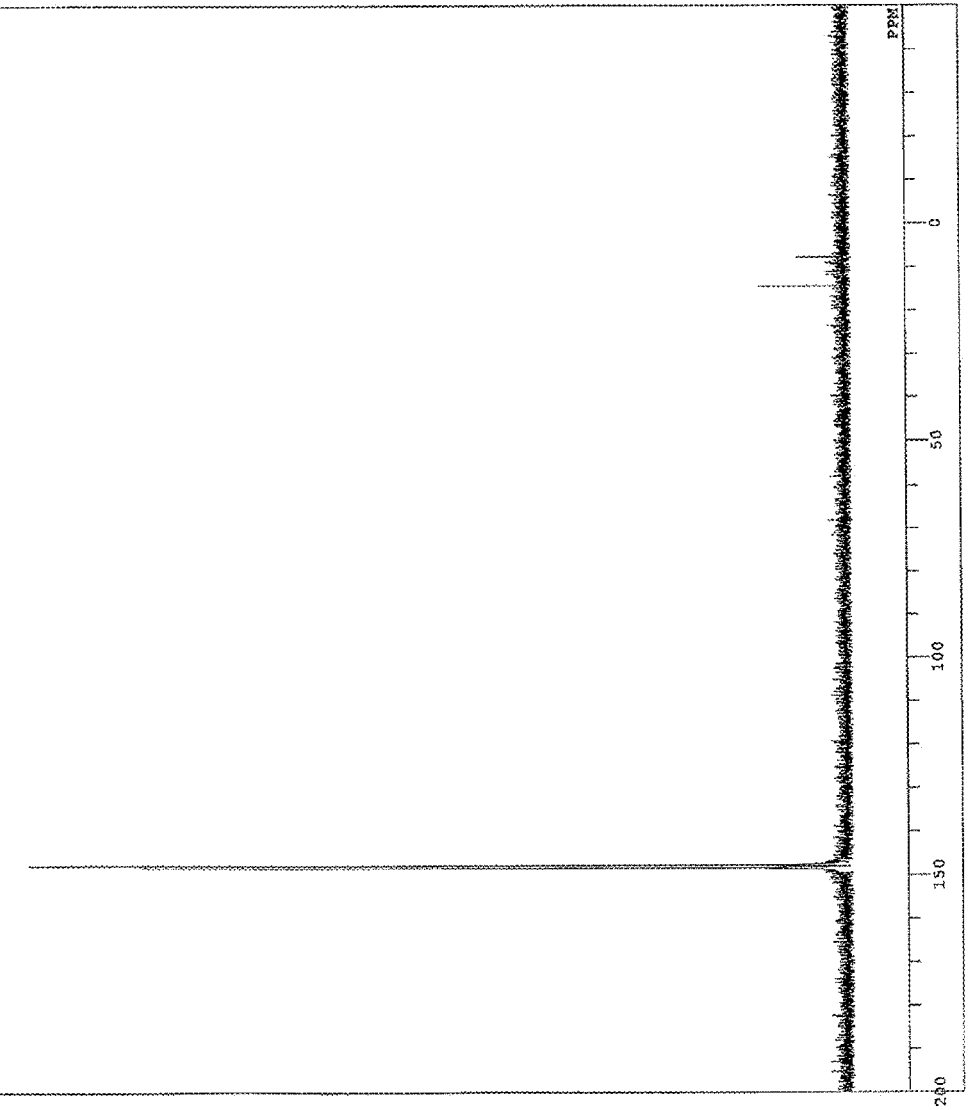
FIG. 15 is a schematic illustration of $^{31}$P-NMR spectrum of compound $IX_{Phe}$ of Example 1.
Figure 16:
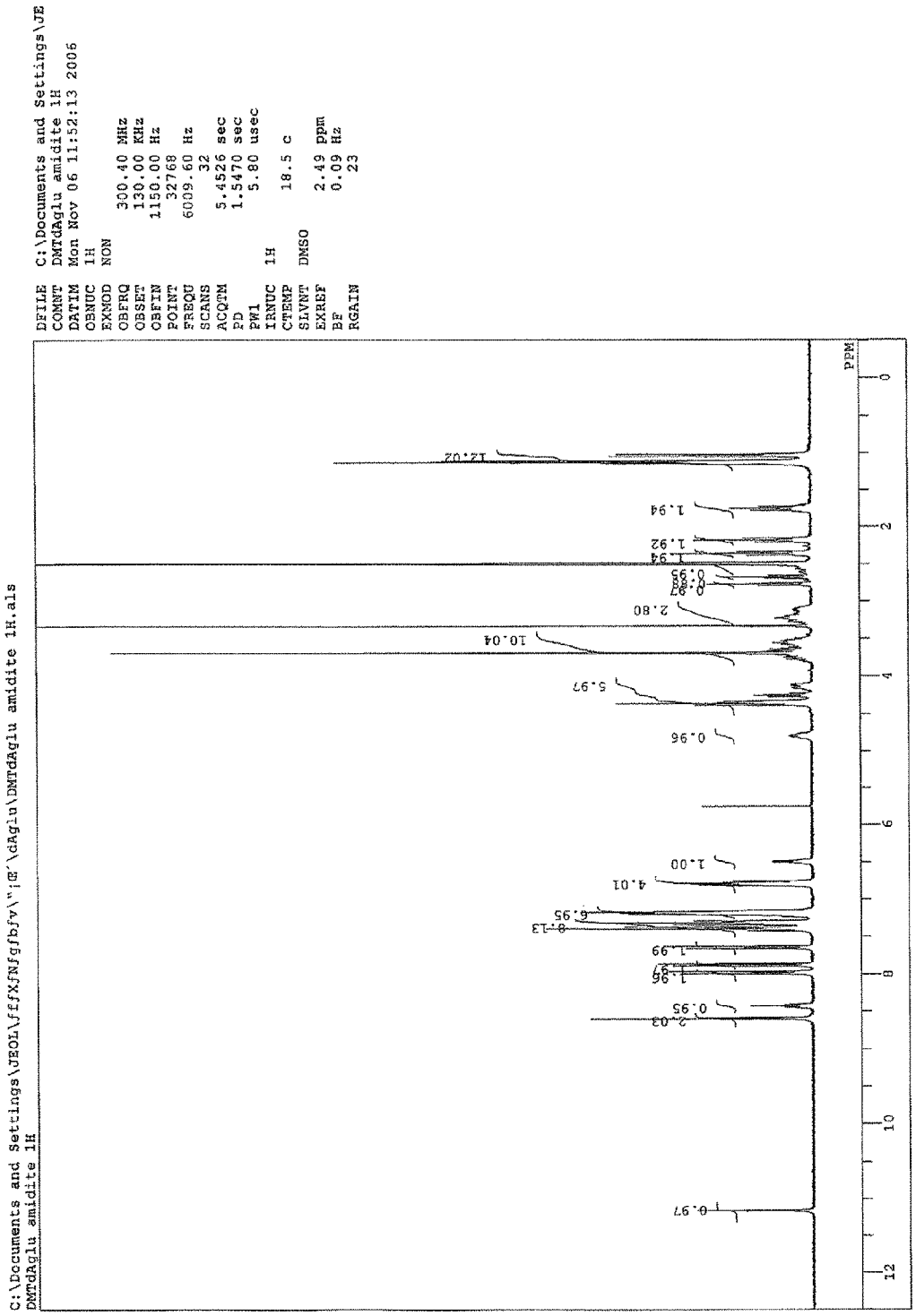
FIG. 16 is a schematic illustration of $^1$H-NMR spectrum of compound $IX_{Glu}$ of Example 1.
Figure 17:
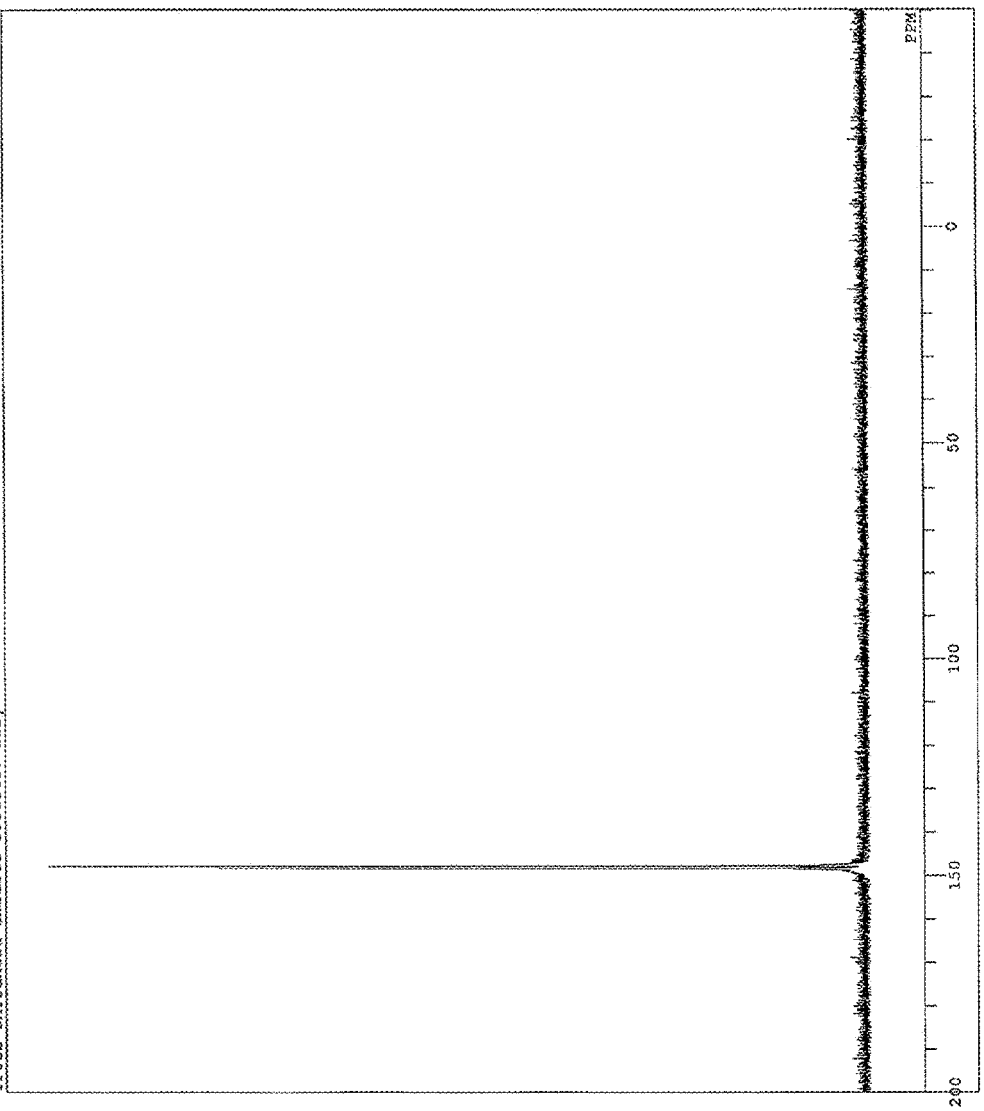
FIG. 17 is a schematic illustration of $^{31}$P-NMR spectrum of compound $IX_{Glu}$ of Example 1.
Figure 18:
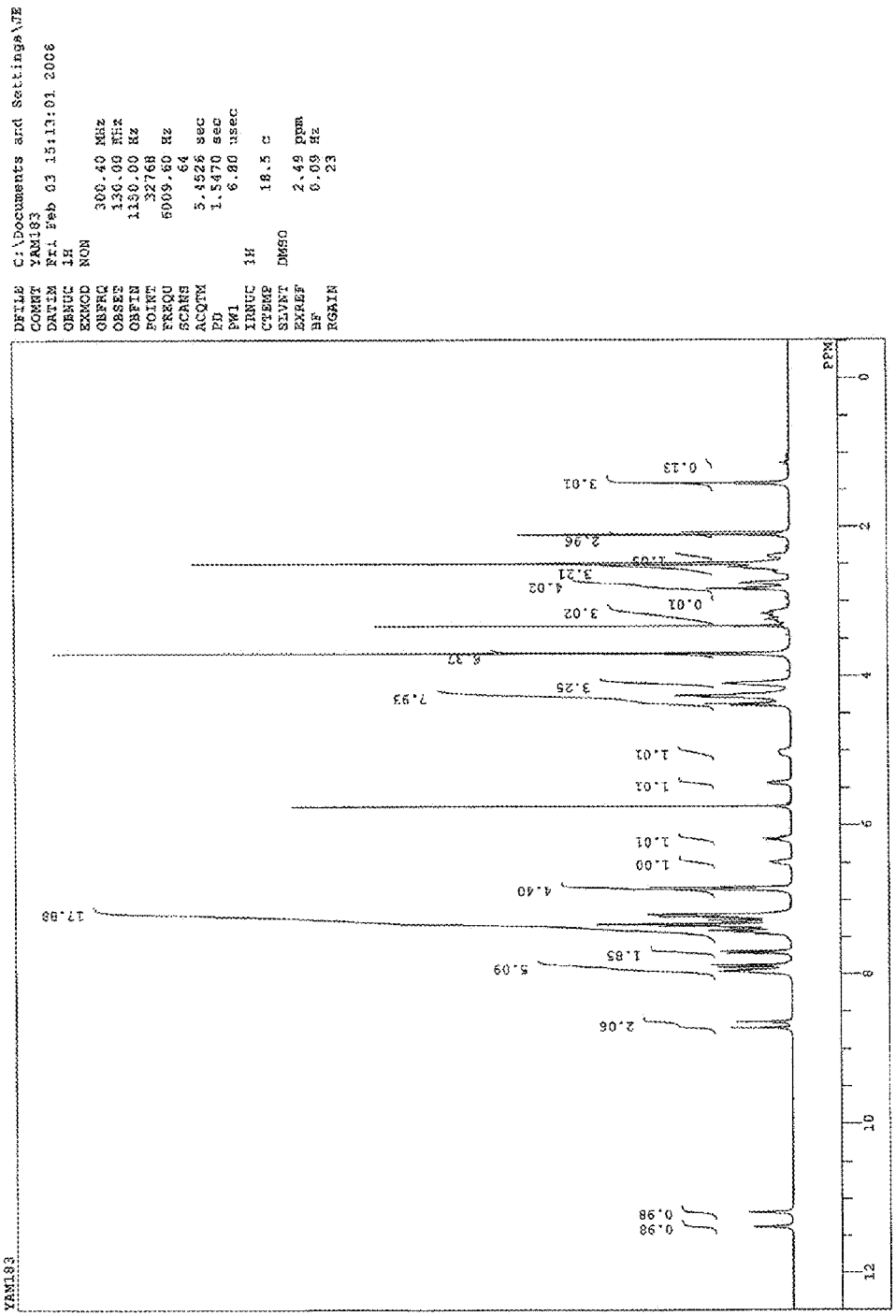
FIG. 18 is a schematic illustration of $^1$H-NMR spectrum of compound $X_{Lys}$ of Example 1.
Figure 19:
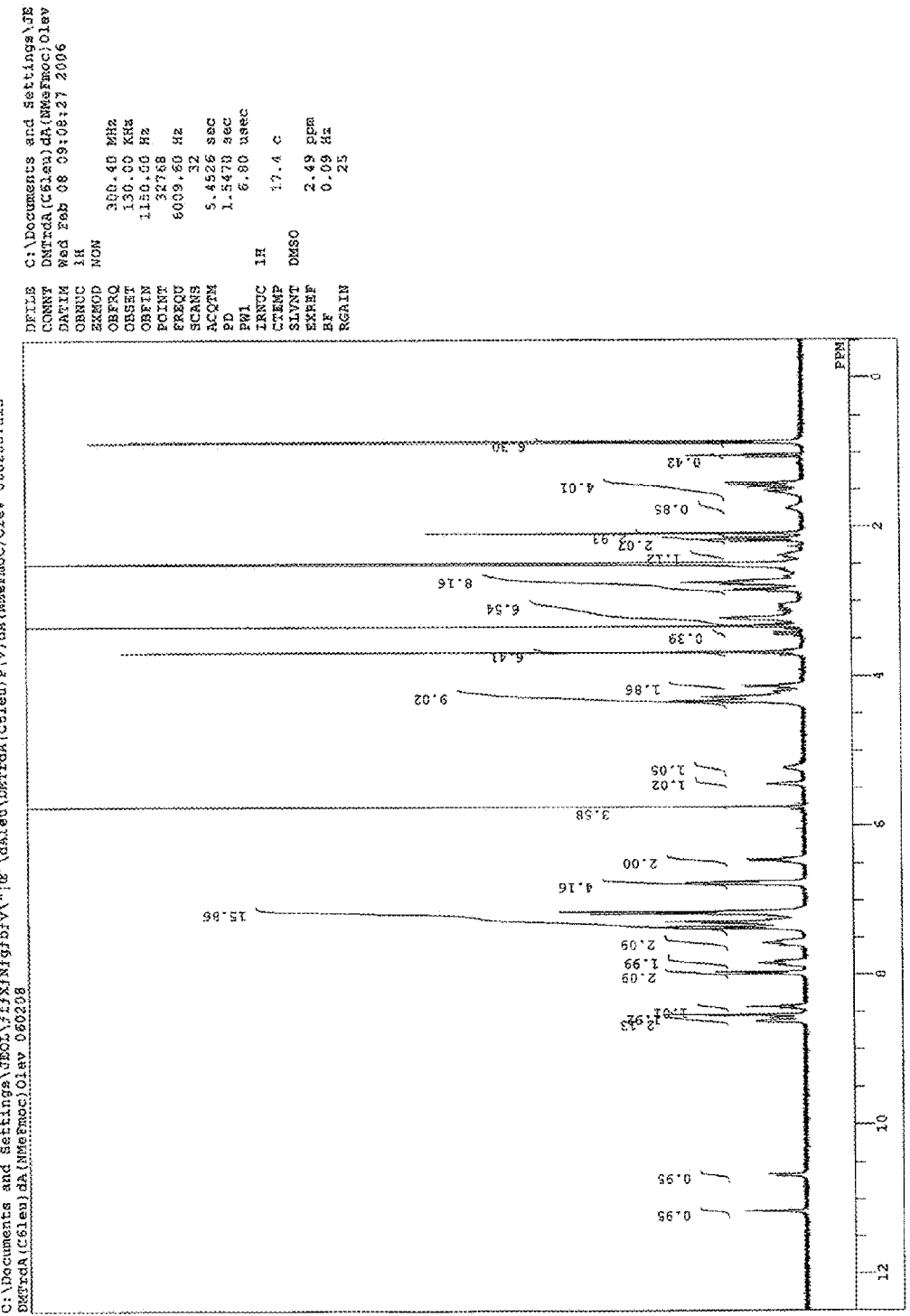
FIG. 19 is a schematic illustration of $^1$H-NMR spectrum of compound $X_{Leu}$ of Example 1.
Figure 20:
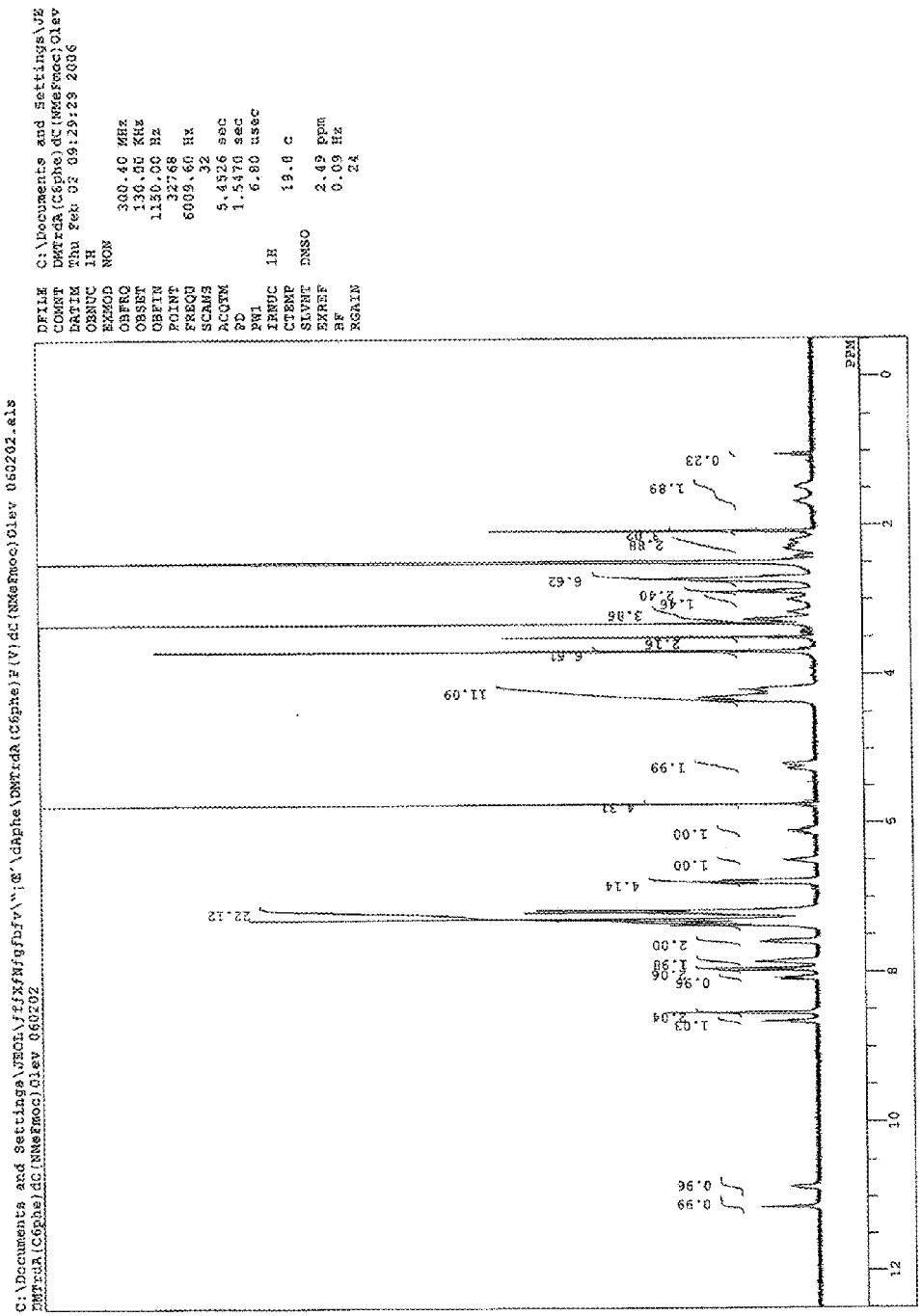
FIG. 20 is a schematic illustration of $^1$H-NMR spectrum of compound $X_{Phe}$ of Example 1.
Figure 21:
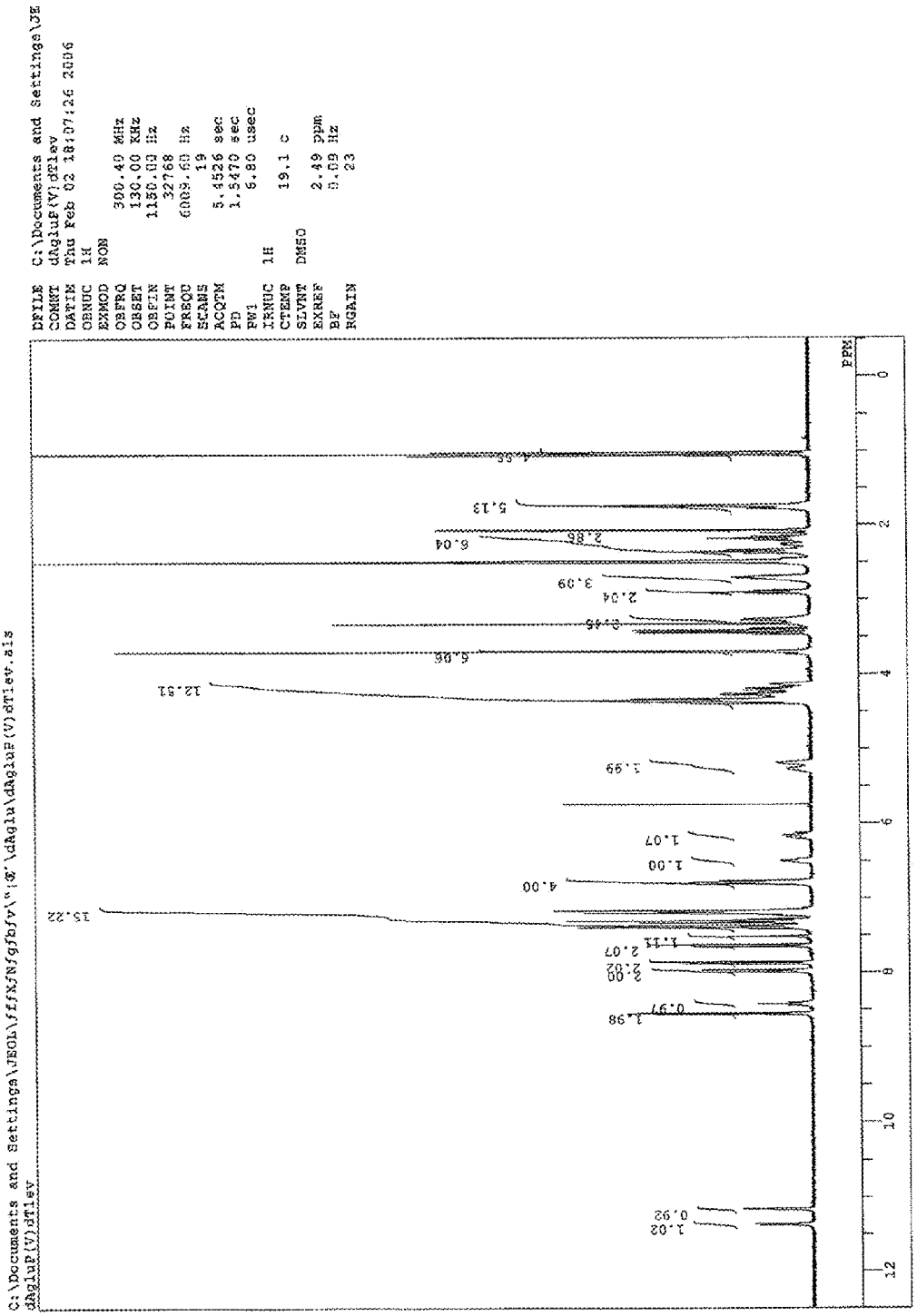
FIG. 21 is a schematic illustration of $^1$H-NMR spectrum of compound $X_{Glu}$ of Example 1.
Figure 22:
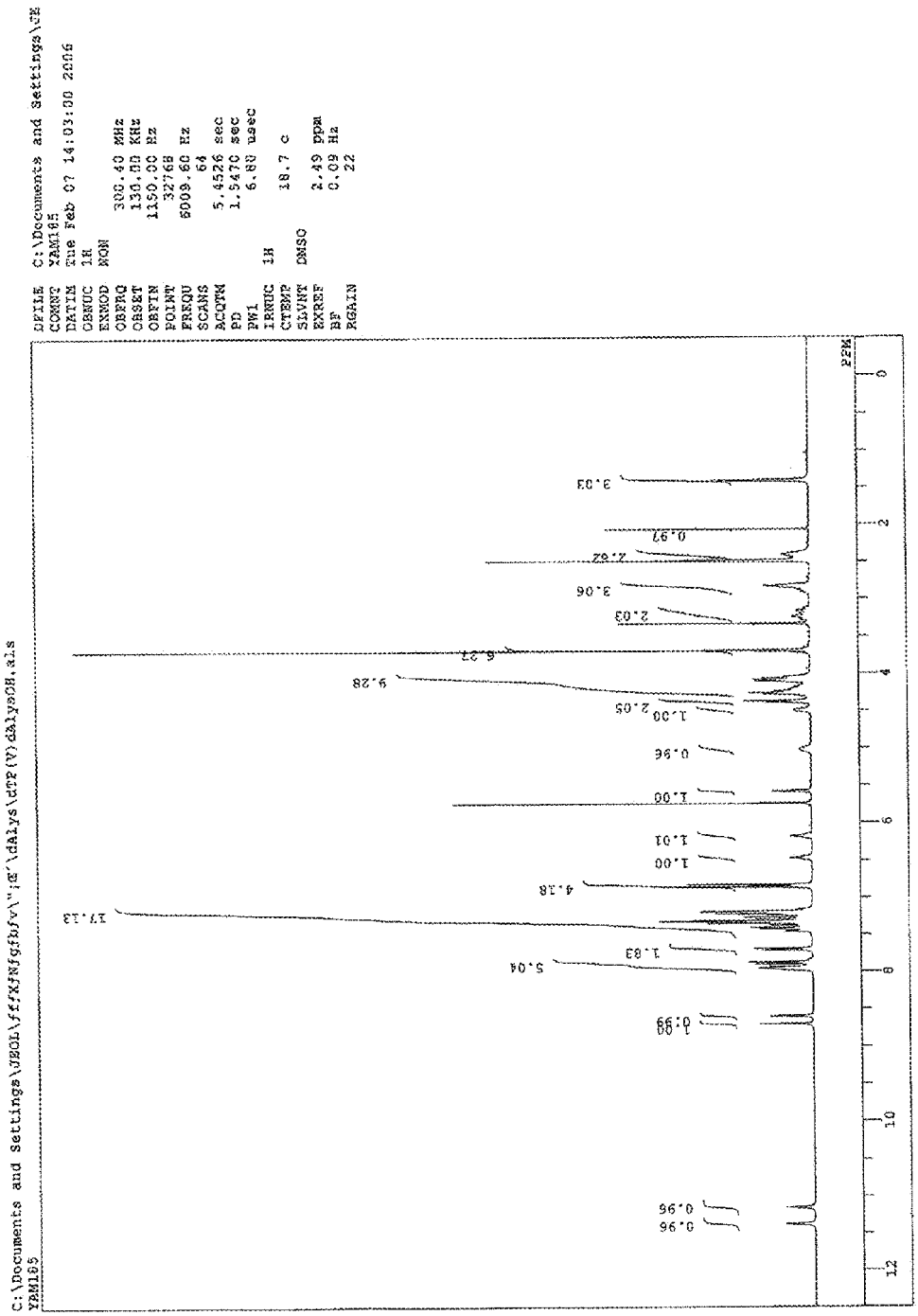
FIG. 22 is a schematic illustration of $^1$H-NMR spectrum of compound $XI_{Lys}$ of Example 1.
Figure 23:
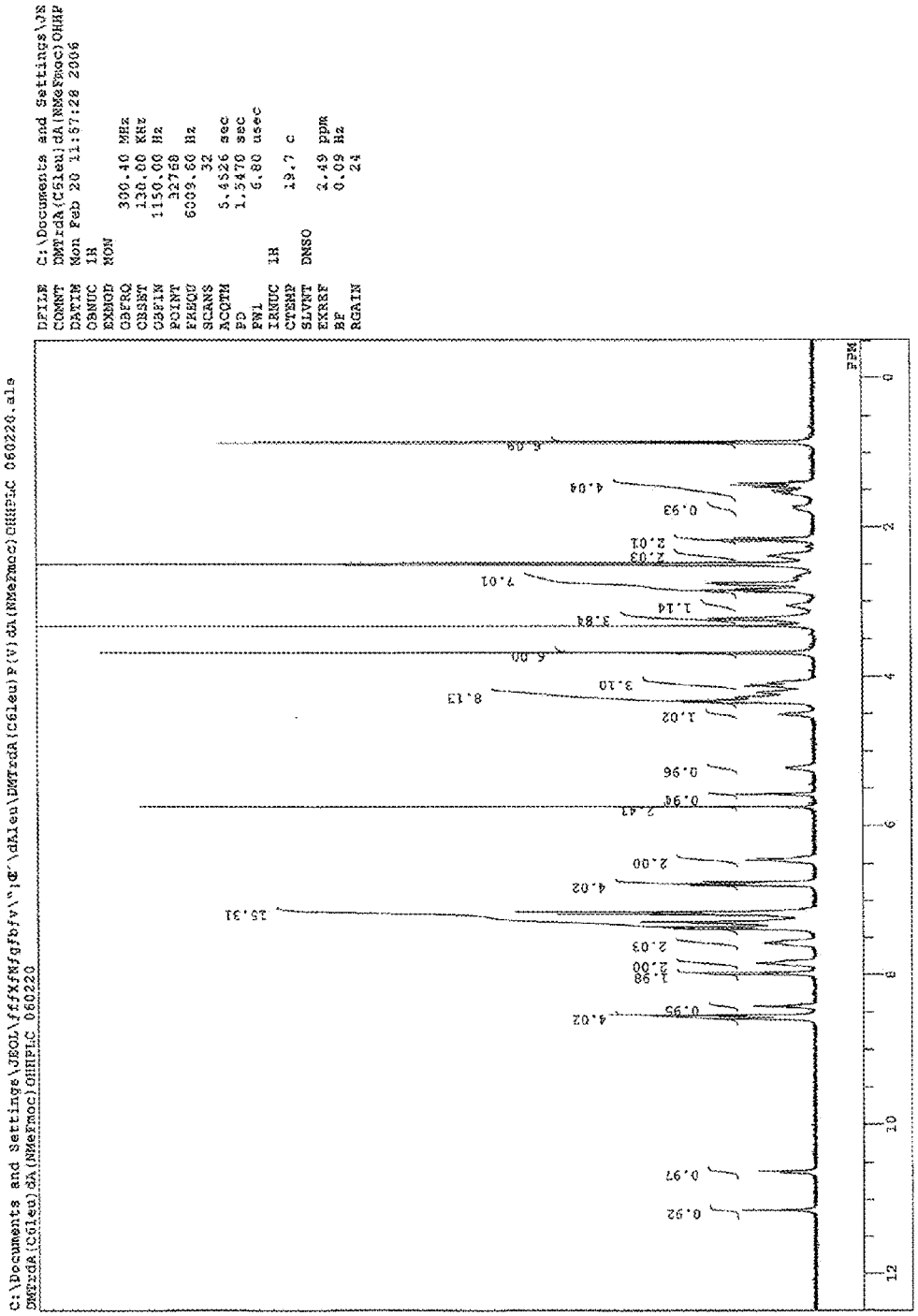
FIG. 23 is a schematic illustration of $^1$H-NMR spectrum of compound XI$_{Leu}$ of Example 1.
Figure 24:
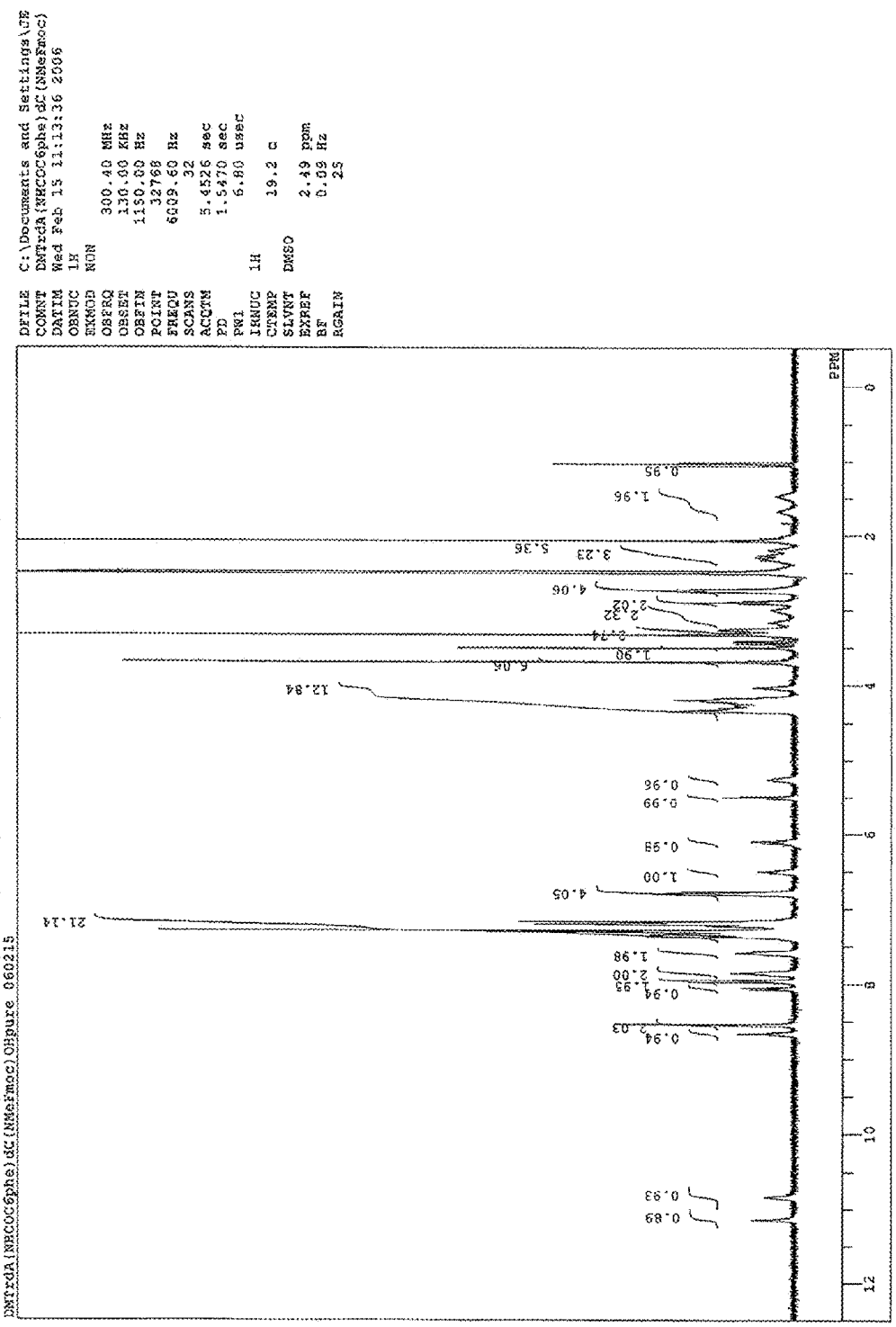
FIG. 24 is a schematic illustration of $^1$H-NMR spectrum of compound XI$_{Phe}$ of Example 1.
Figure 25:
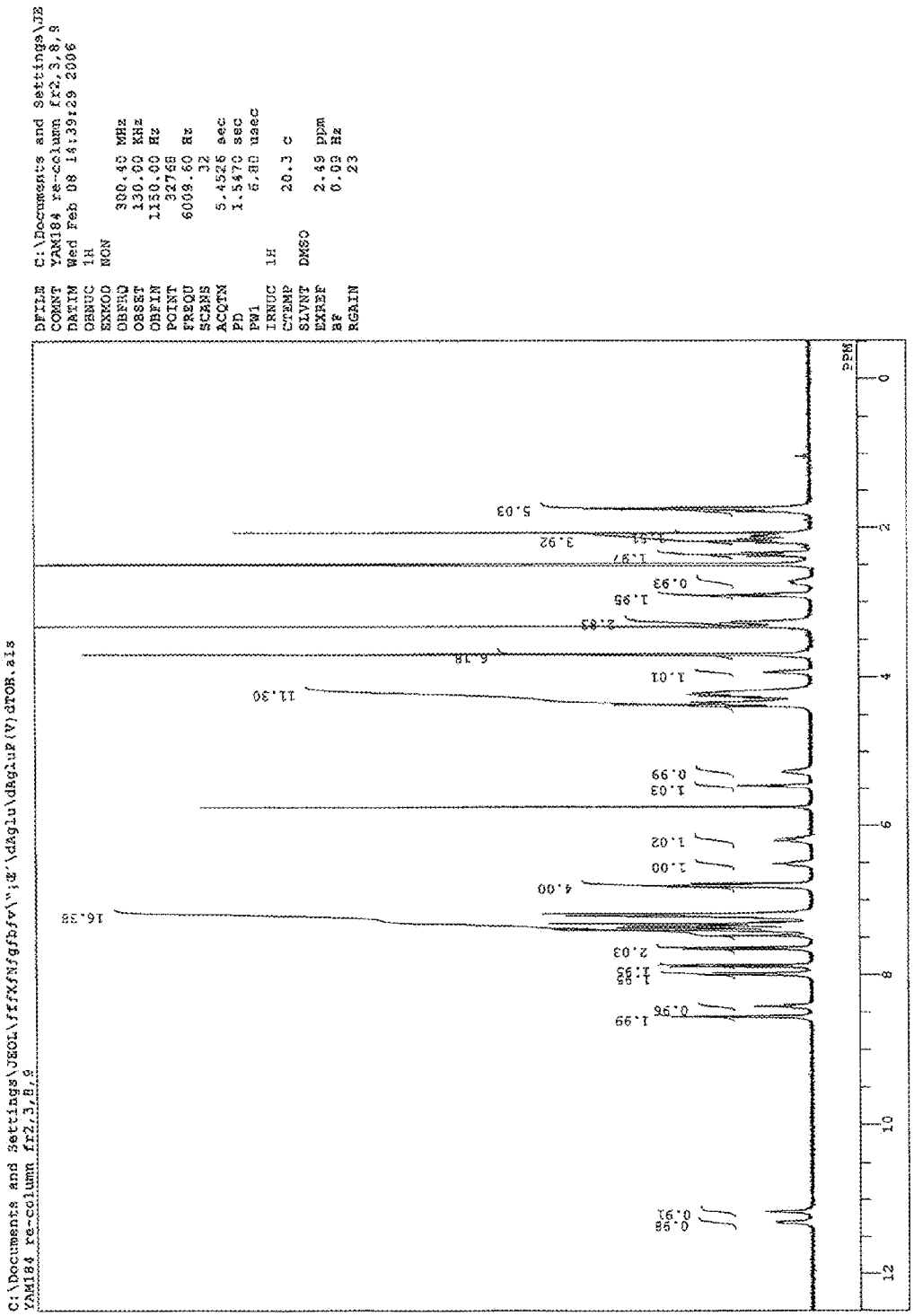
FIG. 25 is a schematic illustration of $^1$H-NMR spectrum of compound XI$_{Glu}$ of Example 1.
Figure 26:
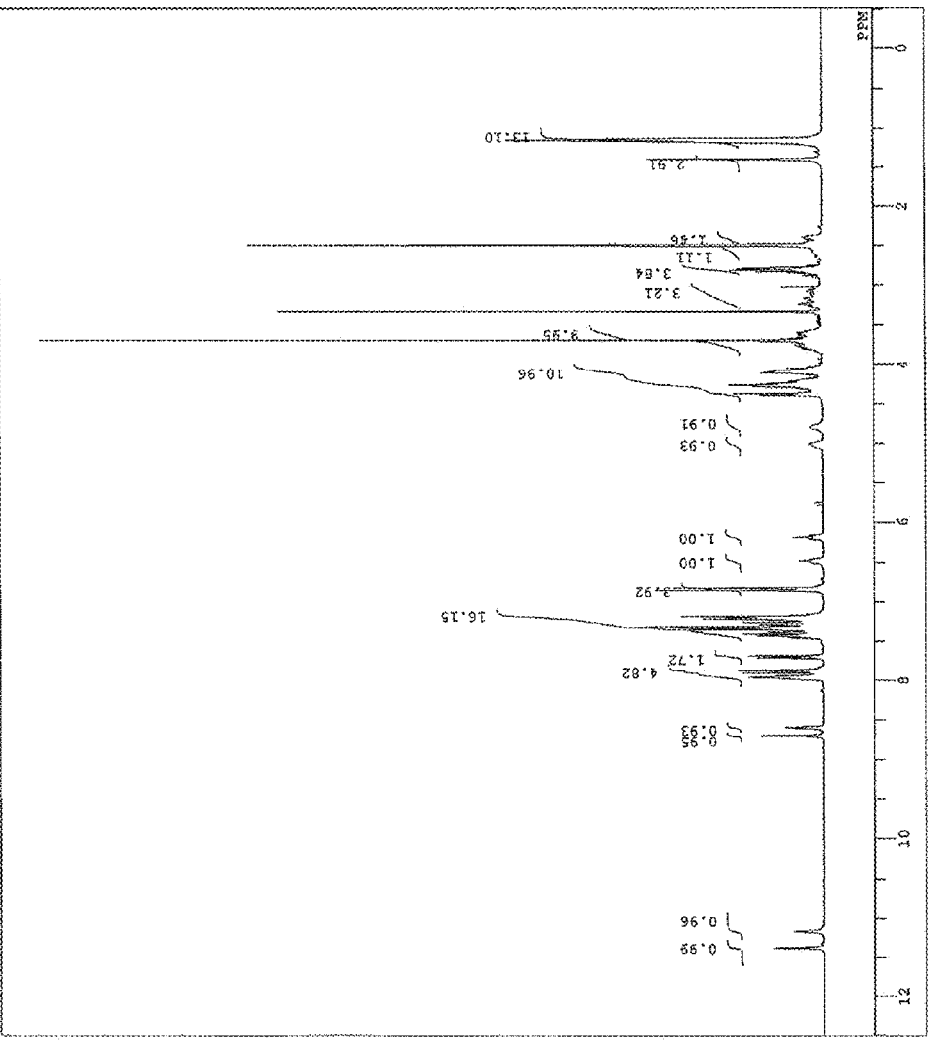
FIG. 26 is a schematic illustration of $^1$H-NMR spectrum of compound XII$_{Lys}$ of Example 1.
Figure 27:
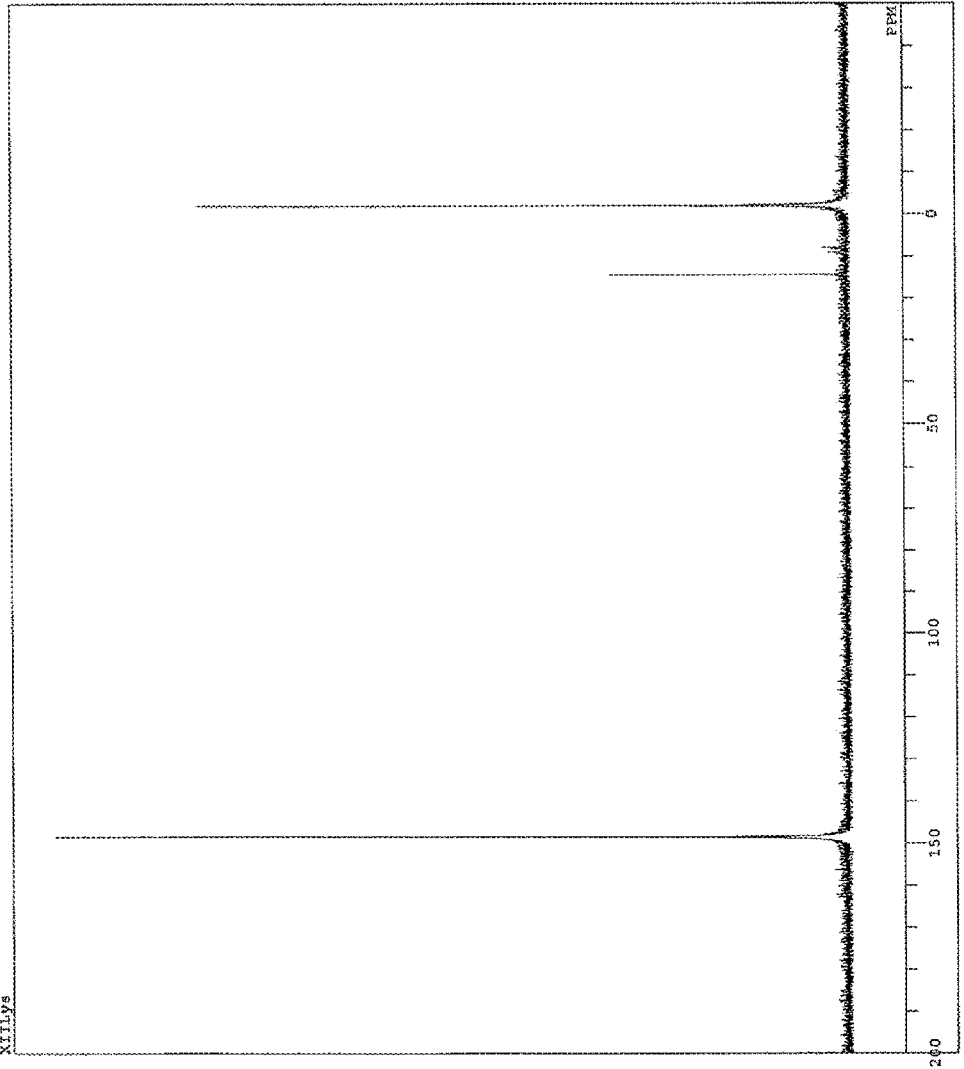
FIG. 27 is a schematic illustration of $^{31}$P-NMR spectrum of compound XII$_{Lys}$ of Example 1.
Figure 28:
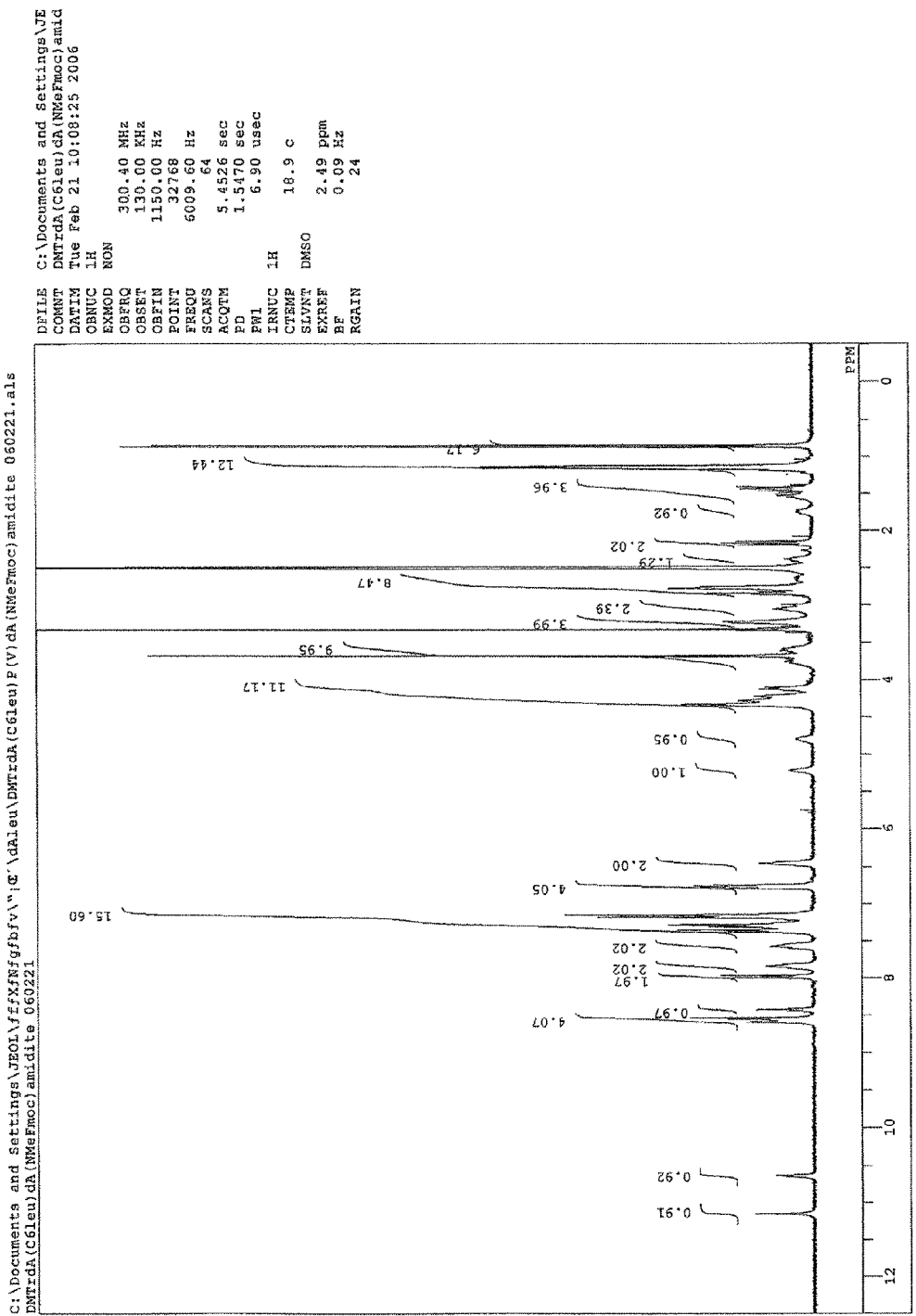
FIG. 28 is a schematic illustration of $^1$H-NMR spectrum of compound XII$_{Leu}$ of Example 1.
Figure 29:
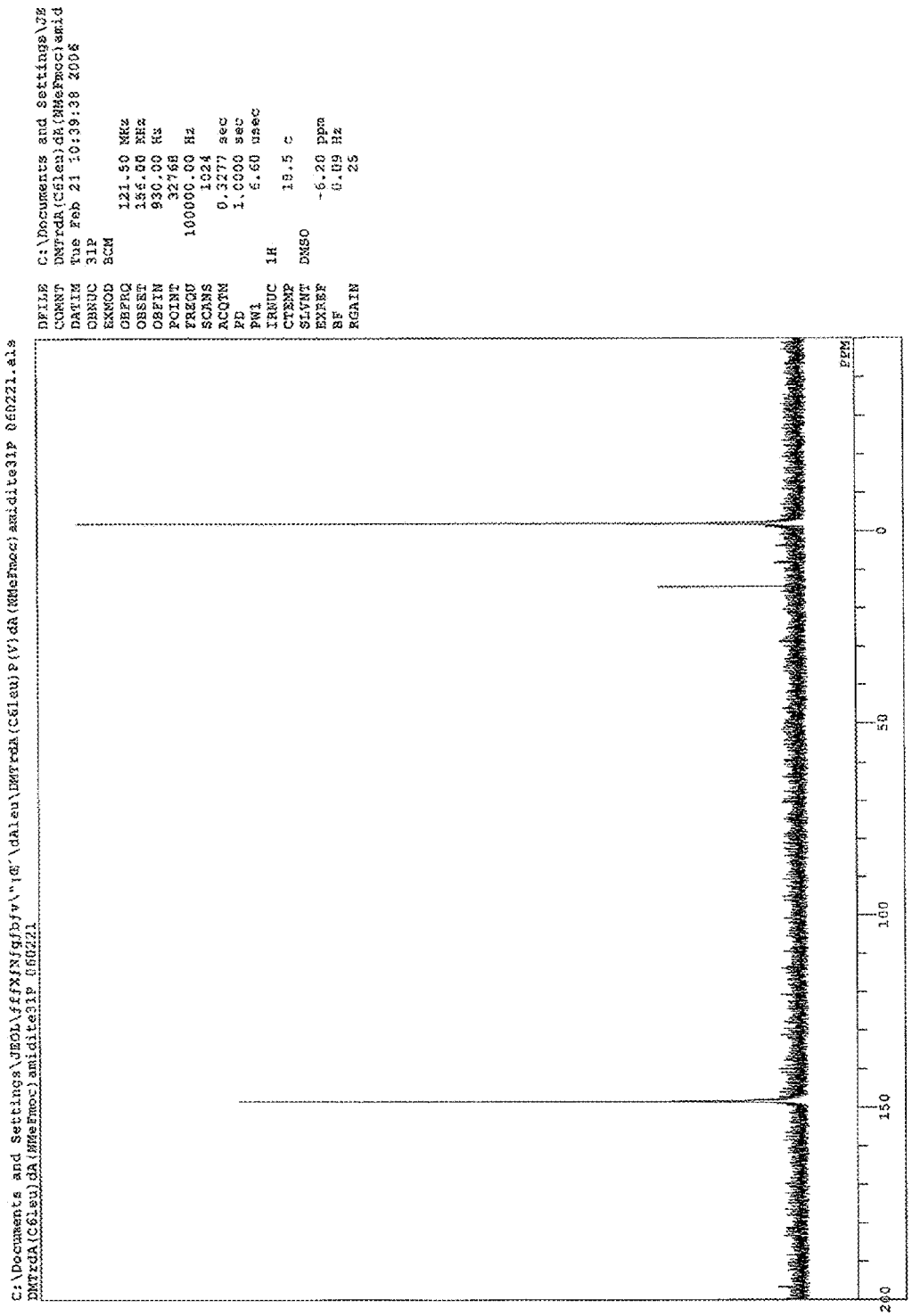
FIG. 29 is a schematic illustration of $^{31}$P-NMR spectrum of compound XII$_{Leu}$ of Example 1.
Figure 30:
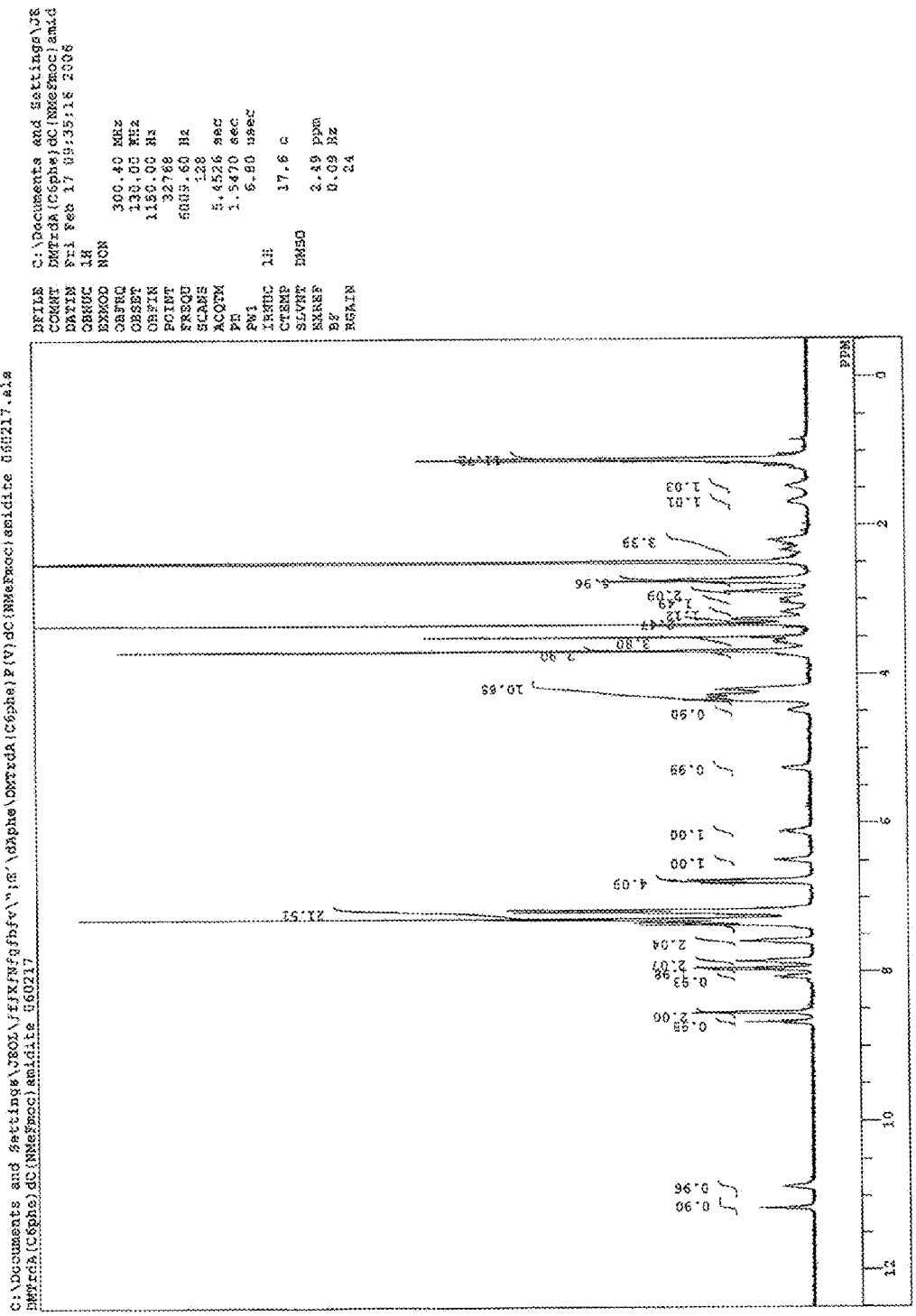
FIG. 30 is a schematic illustration of $^1$H-NMR spectrum of compound XII$_{Phe}$ of Example 1.
Figure 31:
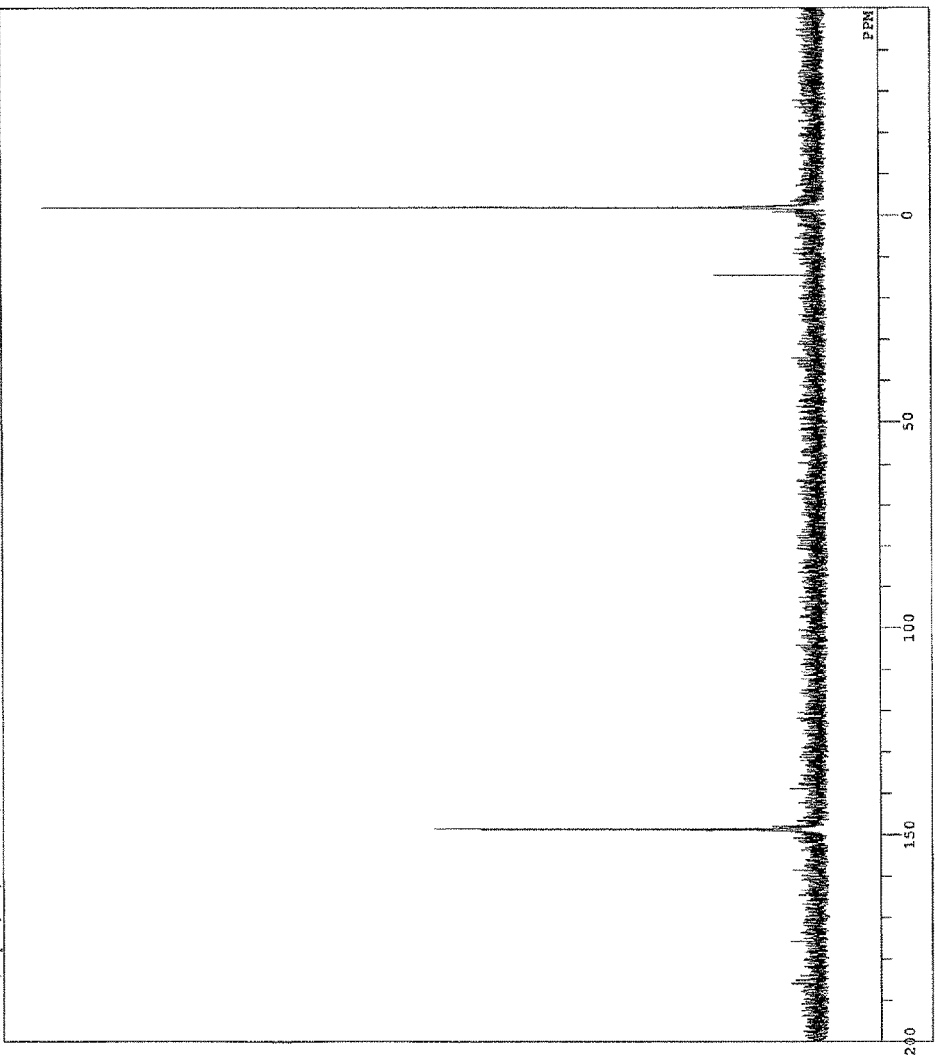
FIG. 31 is a schematic illustration of $^{31}$P-NMR spectrum of compound XII$_{Phe}$ of Example 1.
Figure 32:
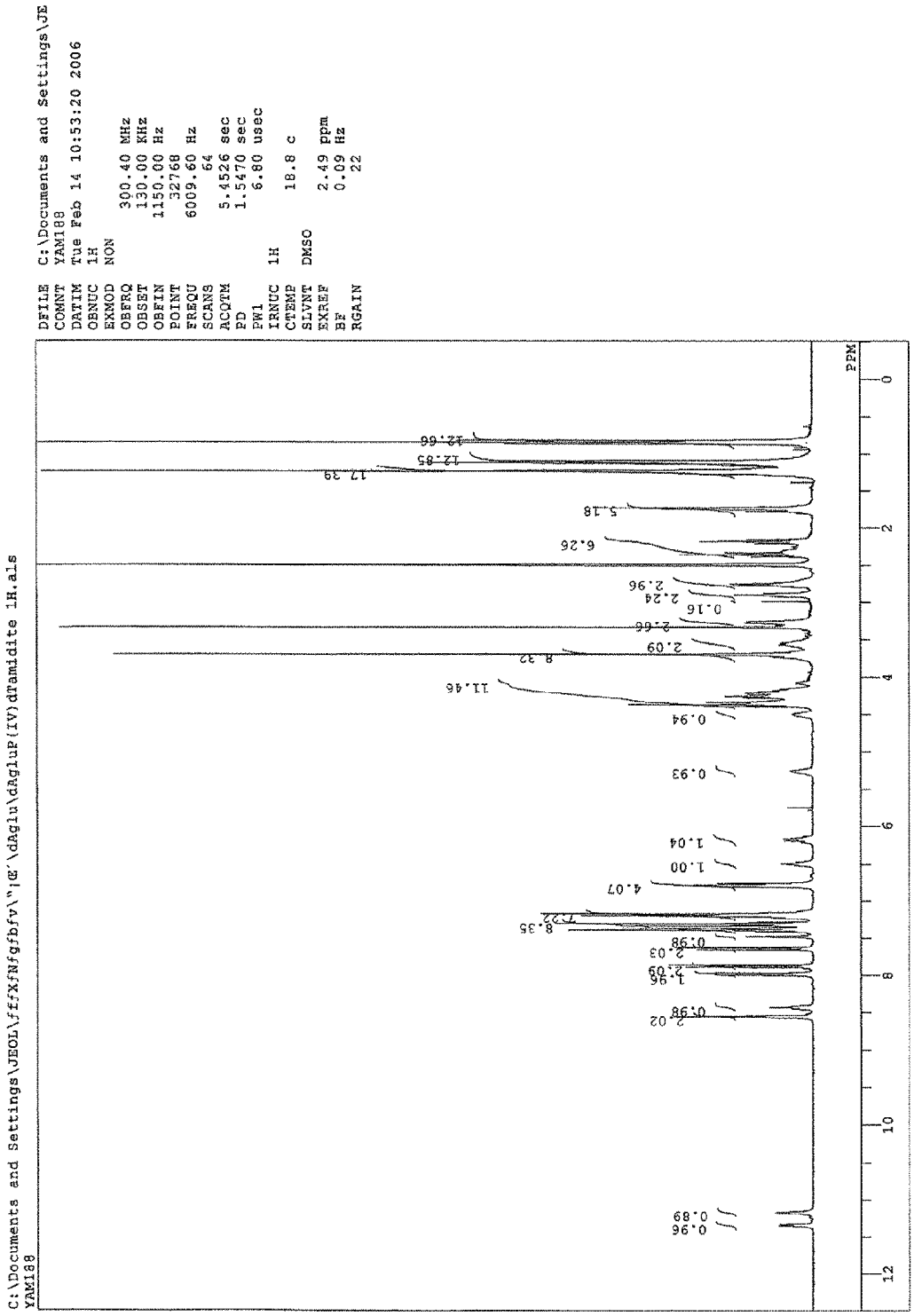
FIG. 32 is a schematic illustration of $^1$H-NMR spectrum of compound XII$_{Glu}$ of Example 1.
Figure 33:
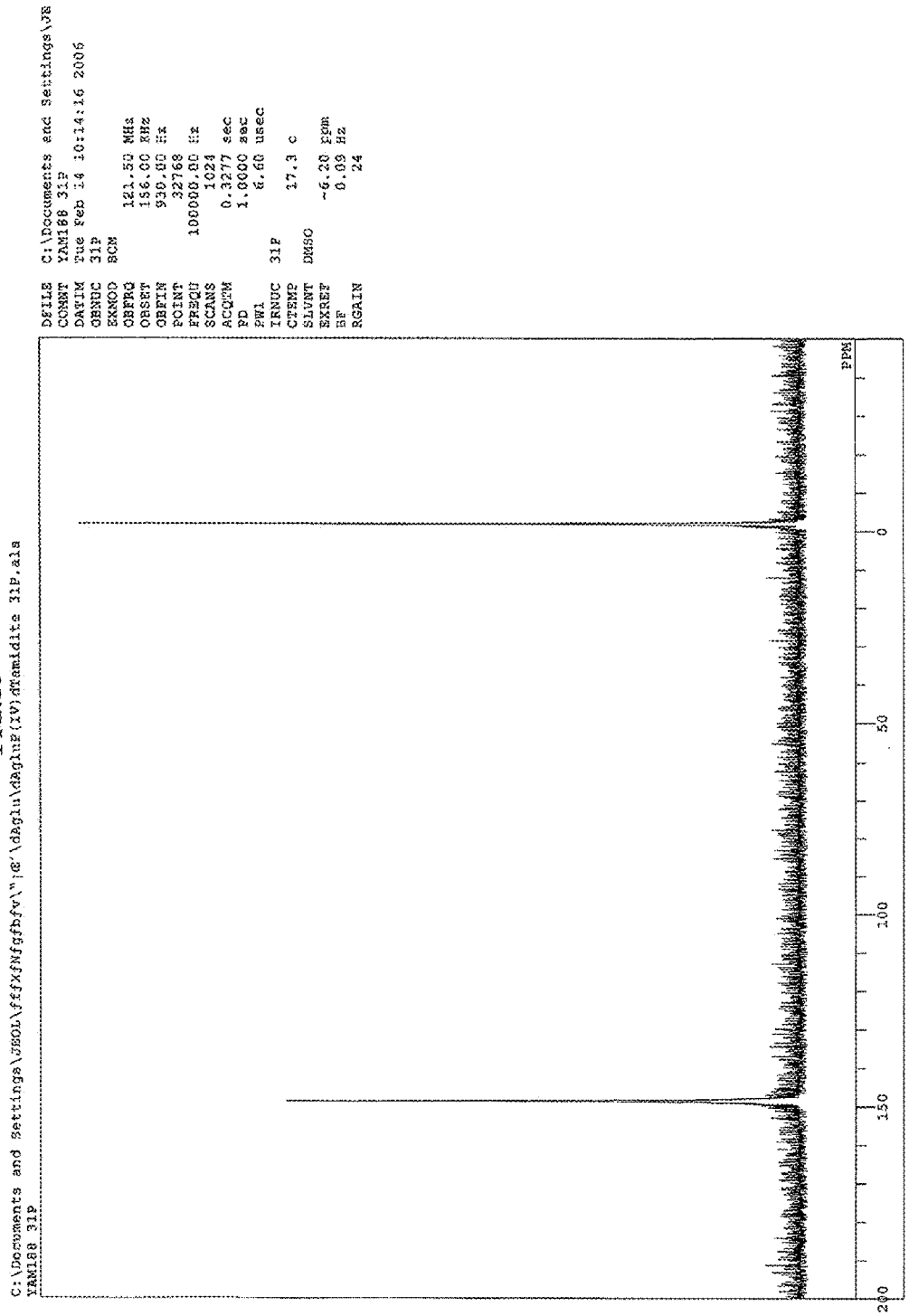
FIG. 33 is a schematic illustration of $^{31}$P-NMR spectrum of compound XII$_{Glu}$ of Example 1.
Figure 34:
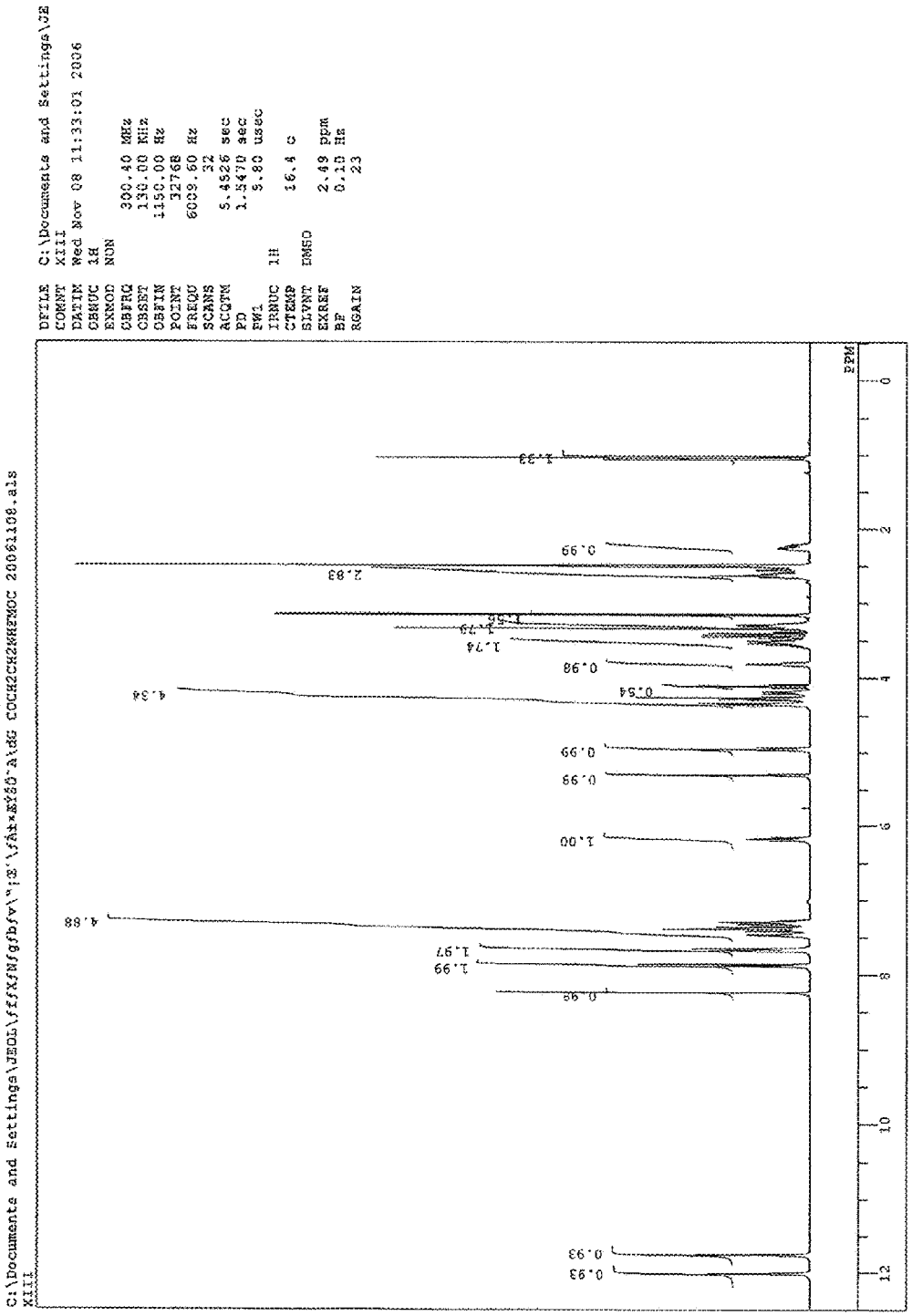
FIG. 34 is a schematic illustration of $^1$H-NMR spectrum of compound XIII of Example 1.
Figure 35:
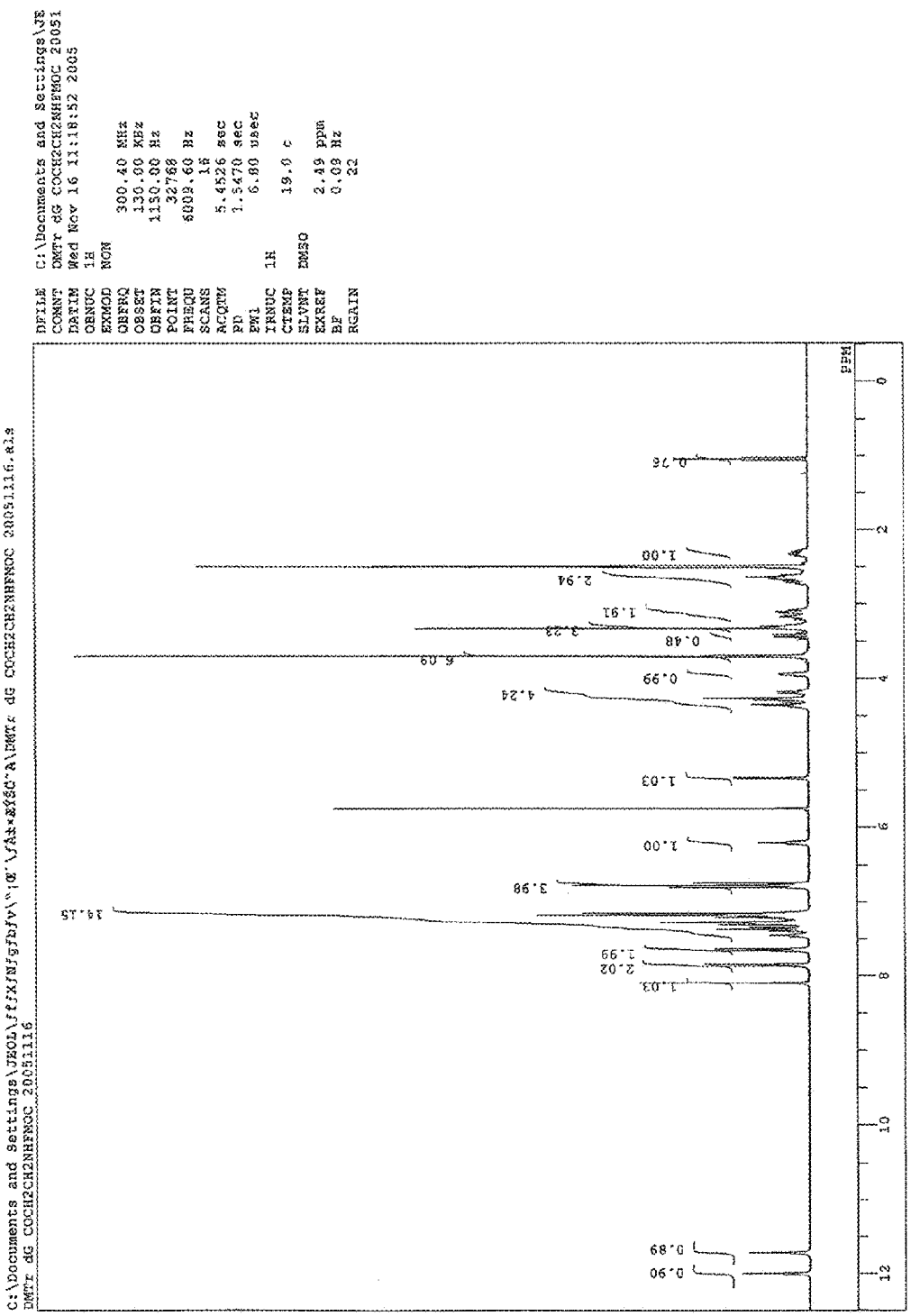
FIG. 35 is a schematic illustration of $^1$H-NMR spectrum of compound XIV of Example 1.
Figure 36:
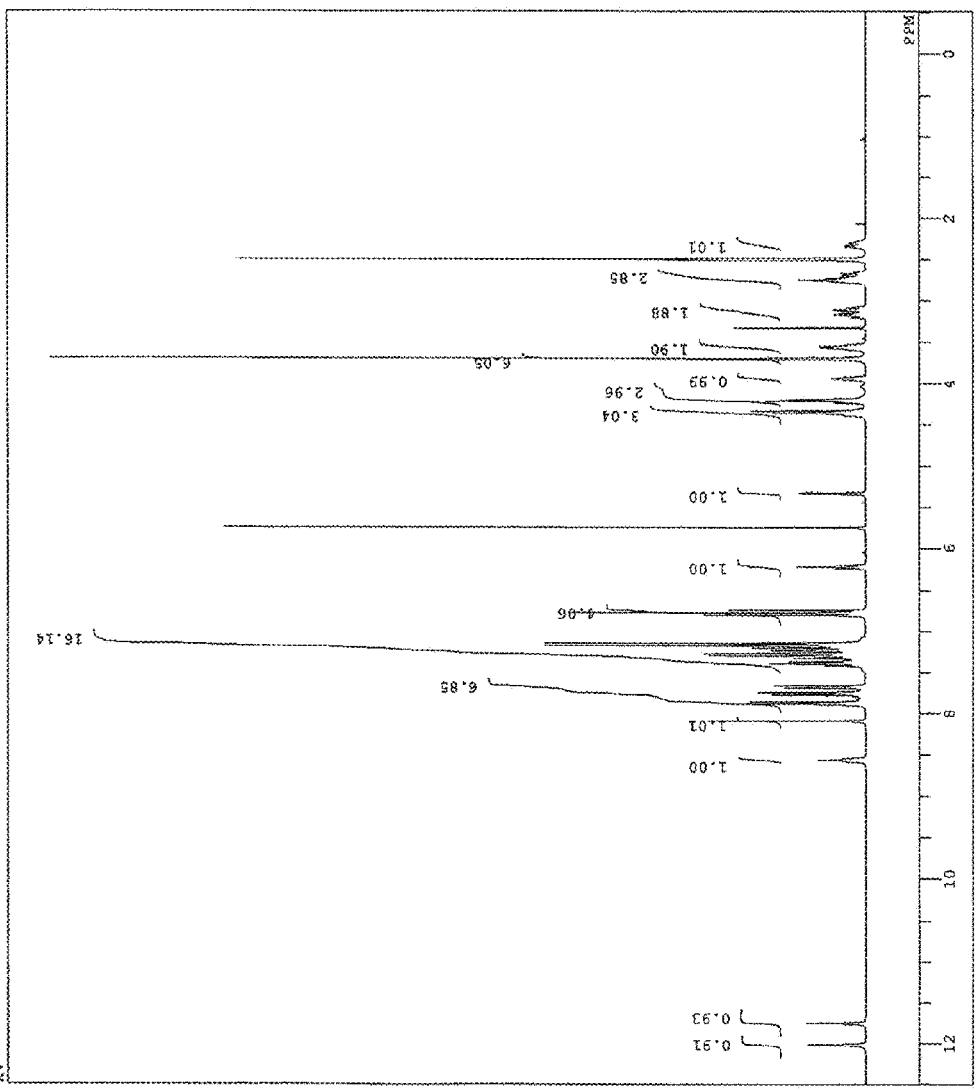
FIG. 36 is a schematic illustration of $^1$H-NMR spectrum of compound XV of Example 1.
Figure 37:
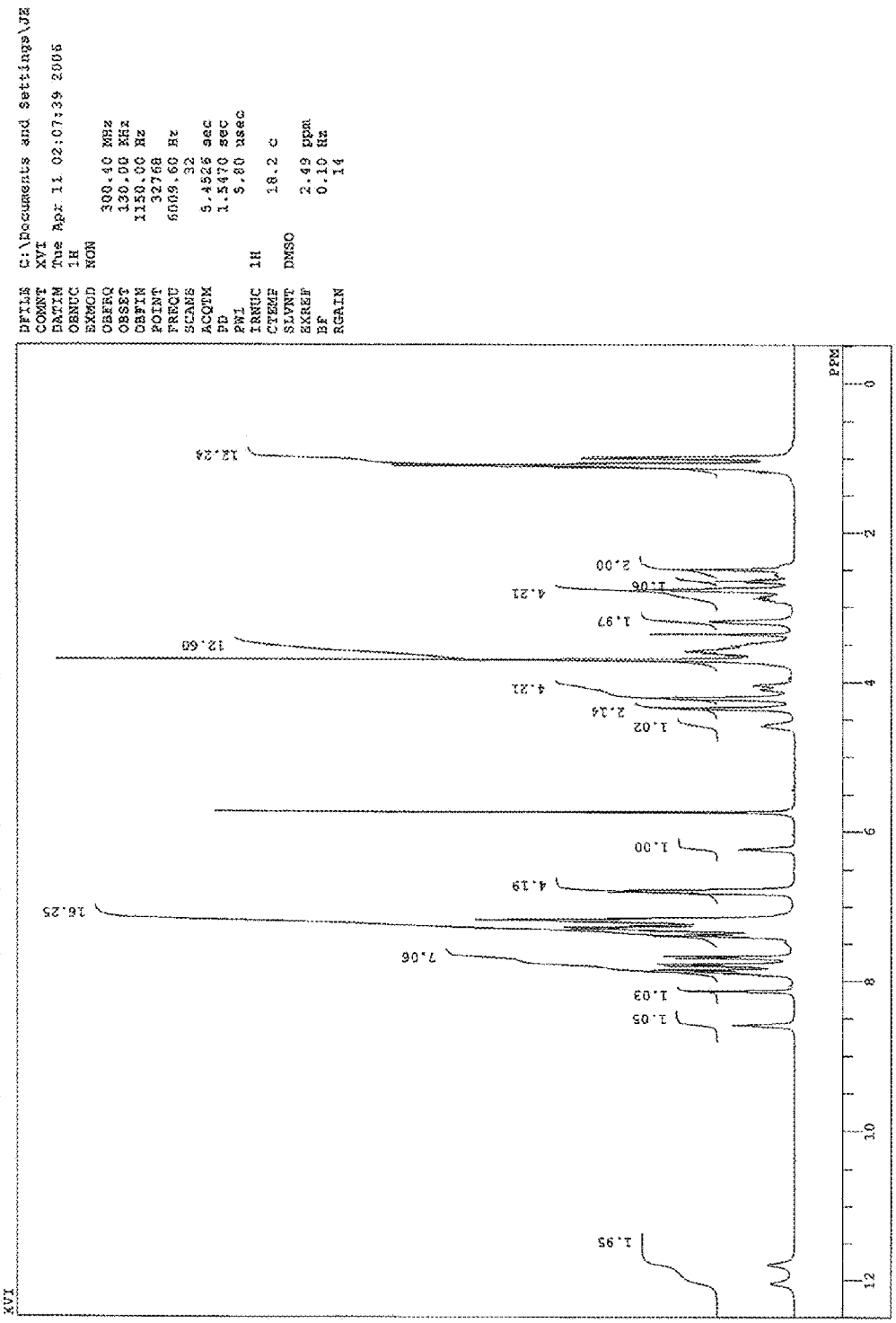
FIG. 37 is a schematic illustration of $^1$H-NMR spectrum of compound XVI of Example 1.
Figure 38:
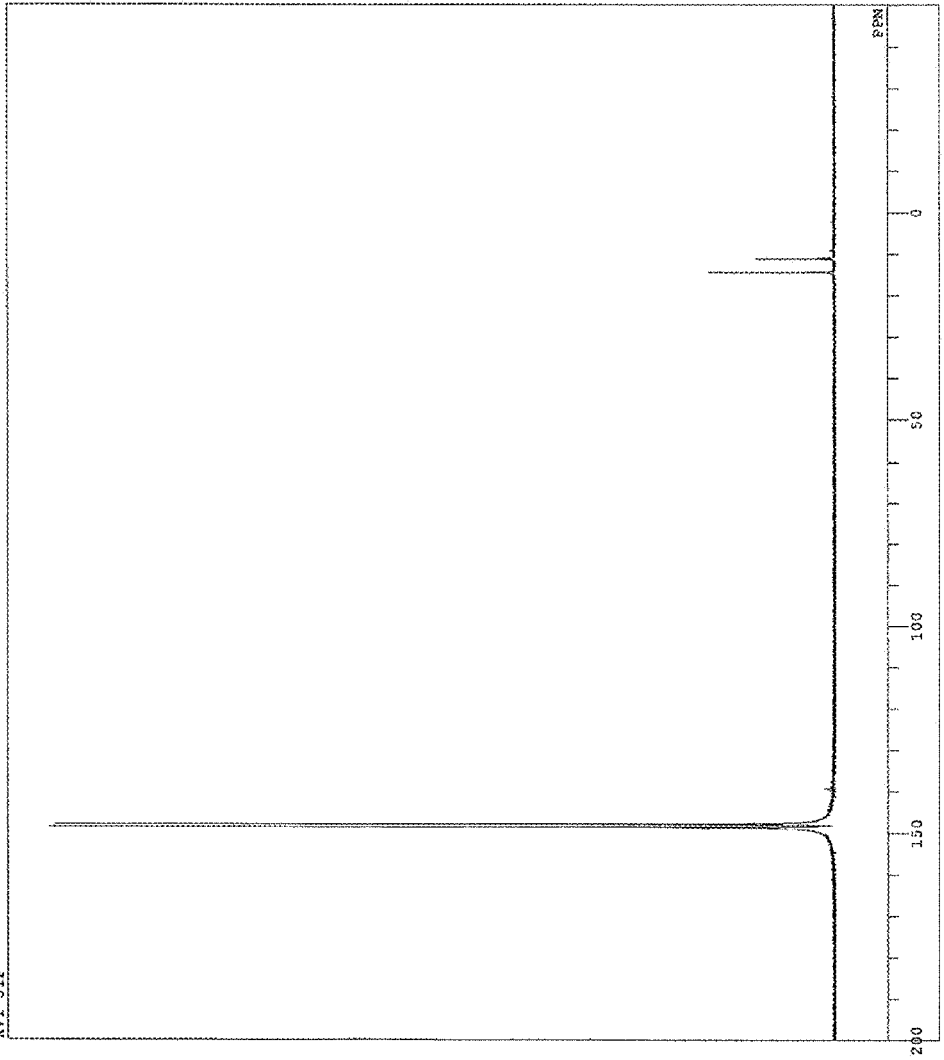
FIG. 38 is a schematic illustration of $^{31}$P-NMR spectrum of compound XVI of Example 1.
Figure 39:
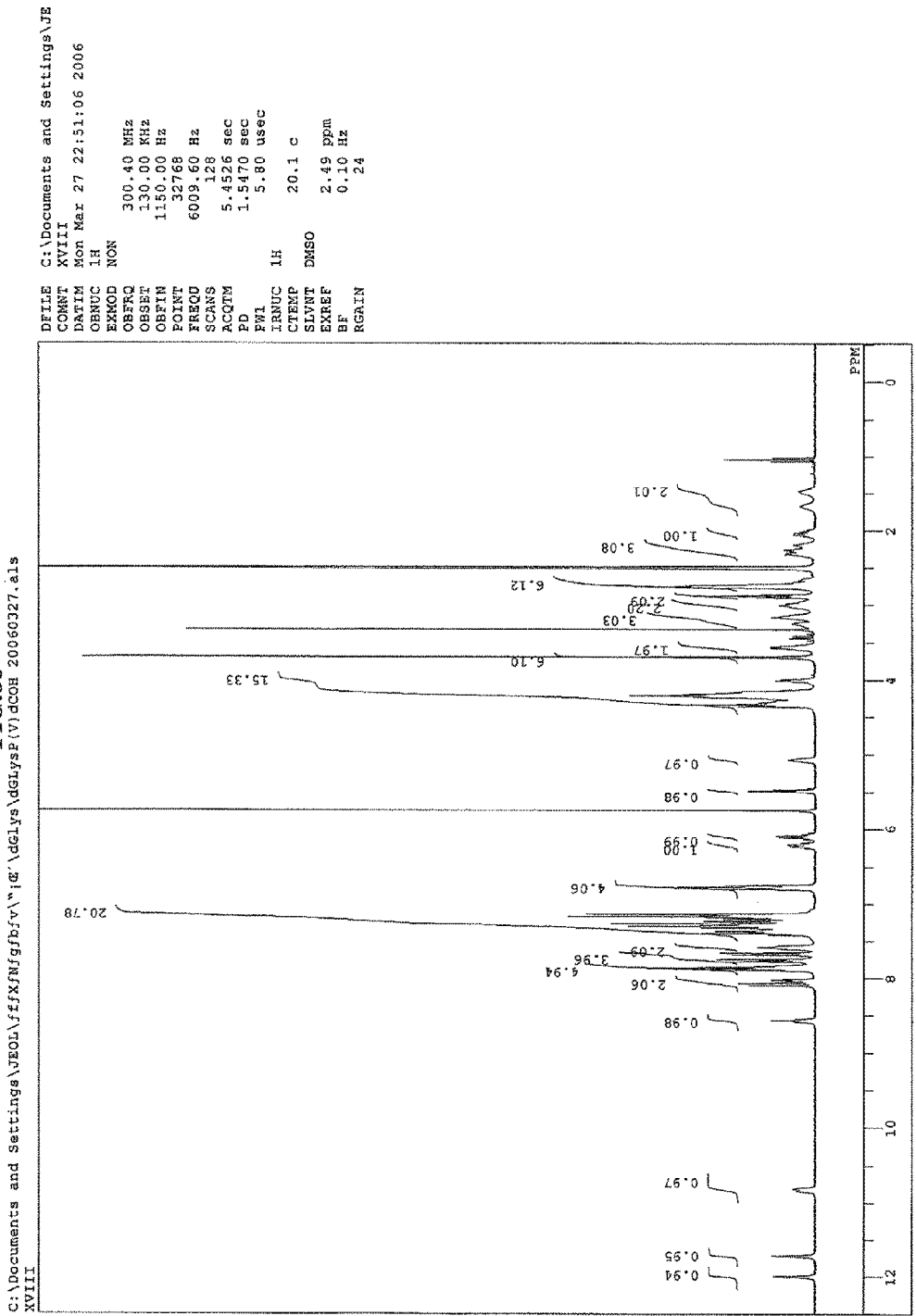
FIG. 39 is a schematic illustration of $^1$H-NMR spectrum of compound XVIII of Example 1.
Figure 40:
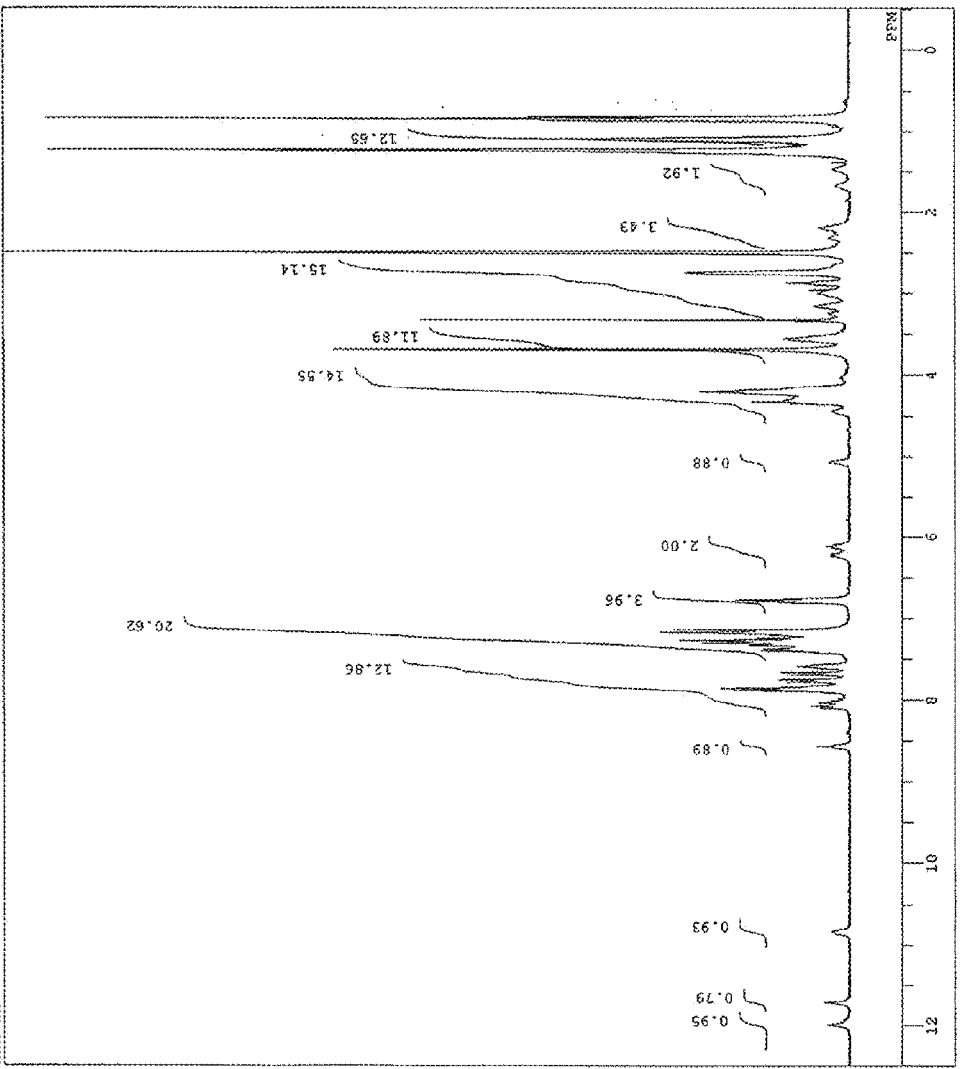
FIG. 40 is a schematic illustration of $^1$H-NMR spectrum of compound XIX of Example 1.
Figure 41:
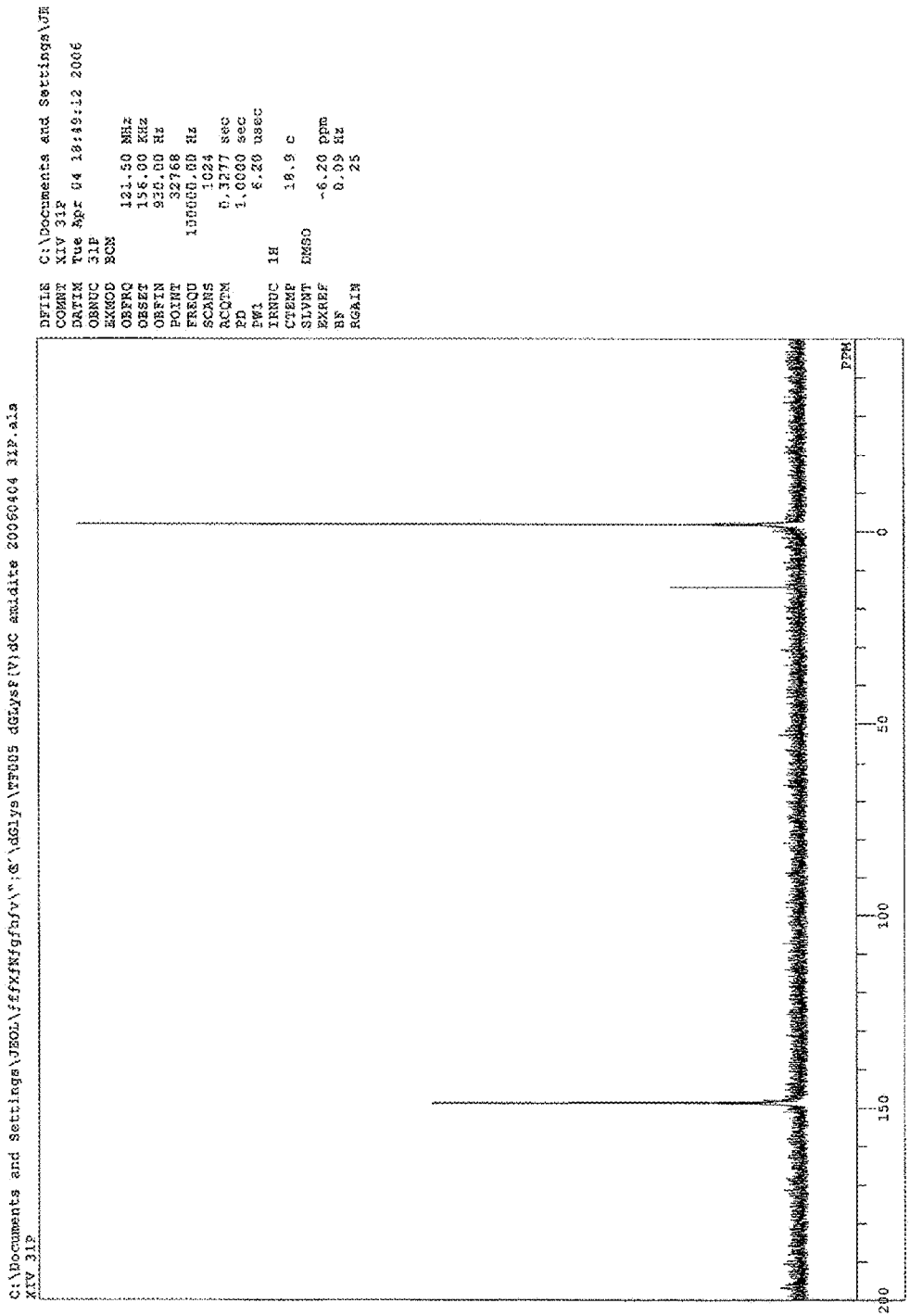
FIG. 41 is a schematic illustration of $^{31}$P-NMR spectrum of compound XIX of Example 1.

The functional molecule according to the present invention is a functional molecule that includes modified nucleotide units each having a substituent, wherein the substituent is introduced to the base so as to be removed.

<Substituent>

The substituent has an easily removable structure at an end thereof and is introduced to the base via the easily removable structure. The easily removable structure is not subjected to any particular limitations and may be appropriately selected according to the application. Preferable examples thereof include aromatic carboxylic acid structures and aliphatic carboxylic acid structures. The easily removable structure is preferably an aromatic carboxylic acid structure when the base is adenine (A) or cytosine (C), whereas it is preferably an aliphatic carboxylic acid structure when the base is guanine (G).

While the aromatic carboxylic acid structure is not subjected to any particular limitations and may be appropriately selected according to the application, specific examples include 4-(alkylcarboxylaminomethyl)benzoic acid and 4-((2-alkylcarboxylamino)ethoxy)benzoic acid. While the aliphatic carboxylic acid structure is not subjected to any particular limitations and may be appropriately selected according to the application, specific examples include N-alkylcarboxylβ-alanine and N-alkylcarboxylpiperidine carboxylic acid.

So long as the substituent is introduced to the base via the easily removable structure as pointed out above, it is not subjected to any particular limitations otherwise and may be selected appropriately according to the application. Examples of other such structures include naturally occurring amino acids and non-naturally occurring amino acids, metal complexes, fluorescent dyes, oxidation-reduction dyes, spin-labeling bodies, a hydrogen atom, alkyl groups having 1 to 10 carbon atoms and groups expressed by formulas (1) through (10) shown below.

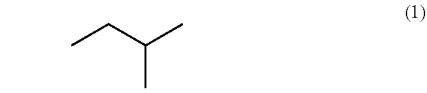

(1)

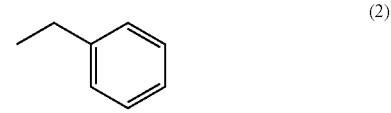

(2)

(3)

(4)

(5)

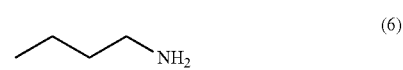

(6)

(7)

(8)

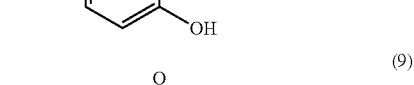

(9)

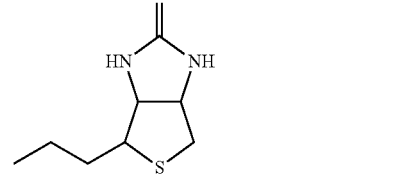

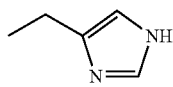 (10)

Naturally occurring and non-naturally occurring amino acids that can be used for the purpose of the present invention are not subjected to any particularly limitations and may be selected appropriately according to the application. Examples of naturally occurring and non-naturally occurring amino acids include valine, leucine, isoleucine, alanine, arginine, glutamine, lysine, asparagic acid, glutamic acid, proline, cysteine, threonine, methionine, histidine, phenylalanine, tyrosine, tryptophan, asparagine, glycine and serine.

Metal complexes that can be used for the purpose of the present invention are not subjected to any particularly limitations so long as ligands are coordinated to metal ions and may be selected appropriately according to the application. Examples of metal complexes include Ru bipyridyl complexes, ferrocene complexes and nickel imidazole complexes.

Fluorescent dyes that can be used for the purpose of the present invention are not subjected to any particularly limitations and may be selected appropriately according to the application. Examples of fluorescent dyes include fluoroscein dyes, rhodamine dyes, eosin dyes and NBD dyes.

Oxidation-reduction dyes that can be used for the purpose of the present invention are not subjected to any particularly limitations and may be selected appropriately according to the application. Examples of oxidation-reduction dyes include leuco dyes such as leucoaniline and leucoanthocyanin.

Spin labeling bodies that can be used for the purpose of the present invention are not subjected to any particularly limitations and may be selected appropriately according to the application. Examples of spin labeling bodies include iron N-(dithiocarboxy)sarcosine and TEMPO (tetramethylpiperidine) derivatives.

Alkyl groups having 1 to 10 carbon atoms that can be used for the purpose of the present invention are not subjected to any particularly limitations and may be selected appropriately according to the application. Examples of alkyl groups having 1 to 10 carbon atoms include methyl group, ethyl group, propyl group, isopropyl group, butyl group, isobutyl group, tert-butyl group, pentyl group, neopentyl group, hexyl group, cyclohexyl group, octyl group, nonyl group and decyl group.

Any of the above listed substituents may be substituted further.

<Base>

Bases that can be used for the purpose of the present invention are not subjected to any particular limitations and may be selected appropriately according to the application. Examples of bases include adenine (A), cytosine (C), guanine (G), thymine (T) and uracil (U). The position where the substituent is introduced to the base is not subjected to any particular limitations and may be selected appropriately according to the application, although the sixth position of adenine base, the sixth position of cytosine base and the second position of guanine base are preferable.

<Removal of Substituent>

The removal method for eliminating the substituent is not subjected to any particular limitations so long as the substituent is removably introduced to the base. Examples of removal method include a method involving an ammonia treatment, a method involving an alkali treatment using an alkali such as NaOH, a method involving a treatment using hydrofluoric acid and fluoride, a method involving a treatment using hydrazine and a method involving irradiation of light, of which the method involving an ammonia treatment is preferable.

The ammonia concentration in the ammonia treatment is not subjected to any particular limitations and may be selected appropriately according to the application. However, the concentration is preferably between 1% and 30%, more preferably between 10% and 30%, most preferably between 20% and 30%. The temperature of the treatment process by ammonia is not subjected to any particular limitations and may be selected appropriately according to the application. However, the temperature is preferably between 0° C. and 80° C., preferably between 25° C. and 60° C., most preferably between 50° C. and 55° C. The duration of the treatment process by ammonia is not subjected to any particular limitations and may be selected appropriately according to the application. However, the duration is preferably between 15 minutes and 24 hours, more preferably between 1 hour and 16 hours, most preferably between 4 hours and 8 hours.

While the substituent can be removed by means of a removal process as described above, it is preferable that the substituent be not removed by any of the deprotection processes that will be described later (e.g., a deprotection process by means of a bulky base in an aprotic solvent, more specifically treatment with DBU (1,8-diazabicyclo[5.4.0]-7-undecene) in acetonitrile). If the substituent that is indispensable for coupling the functional molecule to the target substance is removed and by a deprotection process as described above, it results in loss of substituents needed for coupling with the target; therefore, the functional molecule may no longer be coupled to the target.

<Manufacture of Functional Molecule>

A functional molecule can suitably be manufactured using a functional molecule synthesizing amidite according to the present invention. The method for manufacturing a functional molecule will be described under the heading of (functional molecule synthesizing amidite) hereinafter.

<Structure of Functional Molecule>

The functional molecule according to the present invention is composed of a plurality of nucleotide units, some of which are modified nucleotide units each having a substituent removably introduced to the base, as described above.

The number of nucleotide units that form a functional molecule according to the present invention is not subjected to any particular limitations and may be selected appropriately according to the application. However, the number of nucleotide units is preferably between 10 and 200, more preferably between 20 and 100, most preferably between 30 and 80. The proportion of such substituent-containing modified nucleotide units in the functional molecule according to the present invention is not subjected to any particular limitations and may be selected appropriately according to the application. The functional molecule according to the present invention may have an analogous DNA sequence or an analogous RNA sequence, which may be single strand or double stranded.

<Effects>

Since a substituent that participates in coupling to a target substance is removably introduced to the base of a functional molecule according to the present invention, the functional molecule can be made to have a structure similar to that of naturally occurring nucleic acid by eliminating the substituent from the base typically by means of ammonia treatment. Then, as a result, the functional molecule according to the present invention can be amplified with ease by PCR. Note that, throughout the specification, a functional molecule having a substituent and a functional molecule in which substituents have been removed (hence has a structure similar to that of naturally occurring nucleic acid) both refer to a "functional molecule" and are used interchangeably depending on the context.

When a known functional molecule includes two or more different modified nucleotide units having different substituents in its structure, the properties of each of the substituents have to be considered when determine PCR conditions and hence it is very difficult to determine optimal conditions of PCR amplification. On the other hand, when a functional molecule according to present invention includes two or more different modified nucleotide units having different substituents in its structure, all the substituents can be removed by single ammonia treatment, so that the functional molecule has a structure similar to that of naturally occurring nucleic acid. Thus, optimal PCR conditions can be determined with ease.

(Functional Molecule Synthesizing Amidite)

The functional molecule synthesizing amidite according to the present invention is used for the manufacture of the functional molecule according to the present invention and is expressed by General Formula (I) below. It is characterized in that substituent Y is removably introduced to base X.

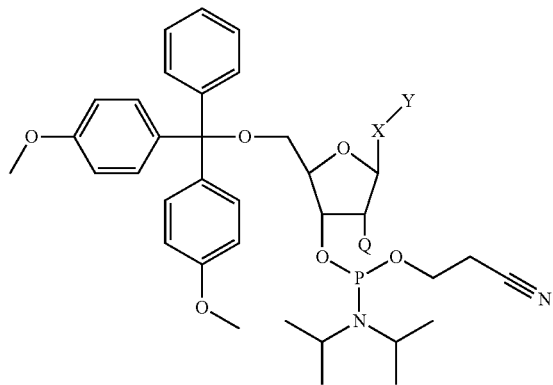

General Formula (I)

where X represents a base, Y represents a substituent and Q represents one of hydrogen atom and hydroxyl group.

The terms "substituent," "base" and "removal (eliminable)" respectively have the same meanings as those described under the heading of Functional Molecule.

Alternatively, the functional molecule synthesizing amidite according to the present invention may be expressed by General Formula (II) below, where substituent Y is further protected by protection group Z for the purpose of preventing an unnecessary reaction of the substituent Y upon synthesis of the functional molecule.

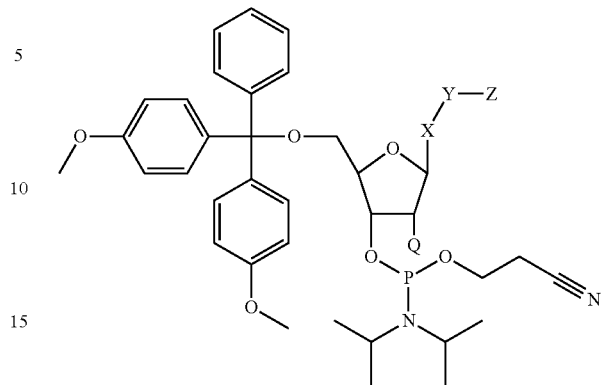

General Formula (II)

where X represents a base, Y represents a substituent, Z represents a protection group and Q represents one of hydrogen atom and hydroxyl group.

<Protection Group>

When the functional molecule synthesizing amidite according to the present invention has protection group Z, the protection group Z is preferably removed under conditions where the substituent Y is not removed. Examples of protection groups that can be used for the purpose of the present invention include a fluorenylmethylcarbonyl group and a β-cyanoethylcarbonyl group. So long as the protection group Z can be removed under conditions where the substituent Y is not removed, the substituent that is indispensable for coupling the functional molecule to the target substance is not lost before coupling to the target substance (at the time of deprotection in the process of manufacturing the functional molecule). Then, a functional molecule that can be coupled to a target substance can be stably manufactured.

<Deprotection>

The method for removing the protection group Z without removing the substituent Y is not subjected to any particular limitations and may be appropriately selected according to the application. Examples of method that can be used for the purpose of the present invention include a treatment method to be conducted in an aprotic solvent by means of a bulky base and a method for using a tetrabutylammonium fluoride treatment, of which the treatment method for treating in the aprotic solvent by means of a bulky base is particularly preferable. The aprotic solvent is not subjected to any particular limitations and may be appropriately selected according to the application. Examples of aprotic solvent include acetonitrile, dichloromethane, DMF (N,N'-dimethylformamide) and N-methylpyrrolidone. The bulky base is not subjected to any limitations either and may be appropriately selected according to the application. Examples of bulky base that can be used for the purpose of the present invention include DBU (1,8-diazabicyclo[5.4.0]-7-undecene), DBN (1,5-diazabicyclo[4.3.0]-5-nonene) and tetramethylguanidine. Preferably, the protection group Z can be removed by DBU in acetonitrile. The DBU concentration necessary for removing the protection group is preferably 0.5M or less, more preferably 0.1M or less, most preferably 0.01M or less. The time period for the deprotection is preferably 8 hours or less, more preferably 1 hour or less, most preferably 15 minutes or less.

<Specific Examples of Functional Molecule Synthesizing Amidite>

Specific examples of the functional molecule synthesizing amidite according to the present invention include, but not limited to, those expressed by one of structural formulas (1) through (5) shown below.

Structural Formula (1)
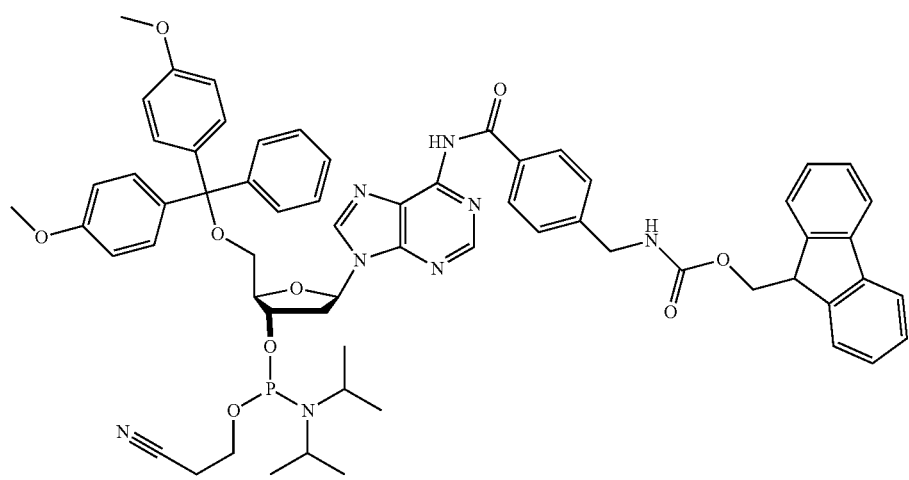
Structural Formula (2)
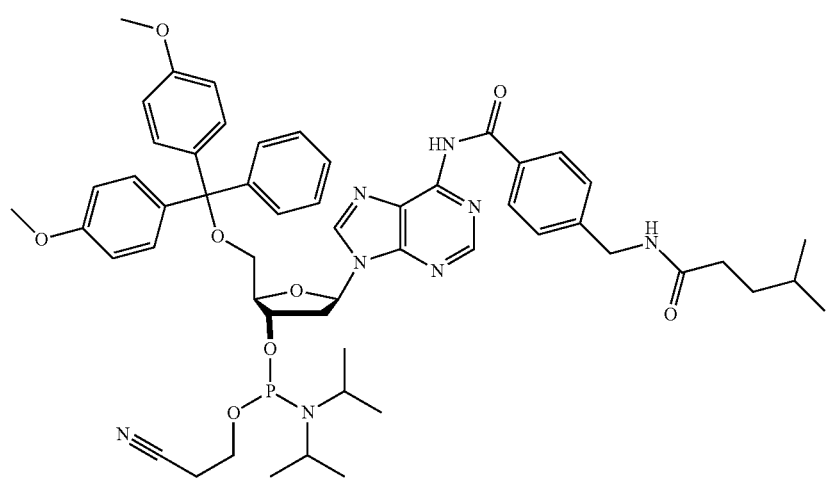
Structural Formula (3)
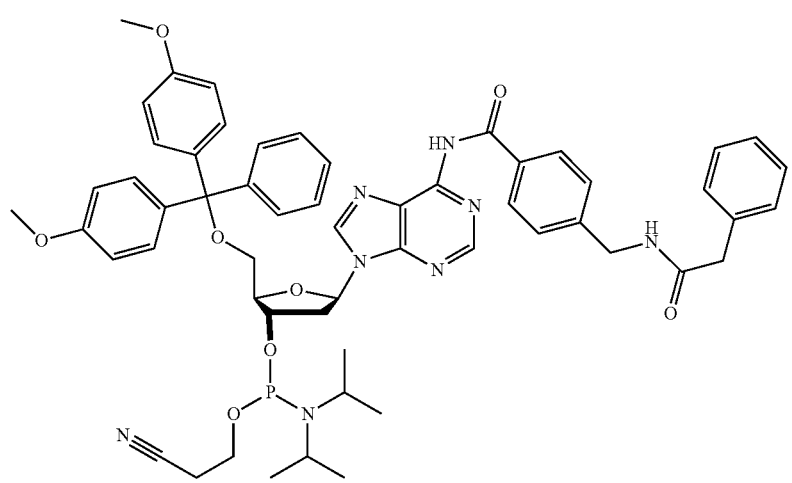

Structural Formula (4)

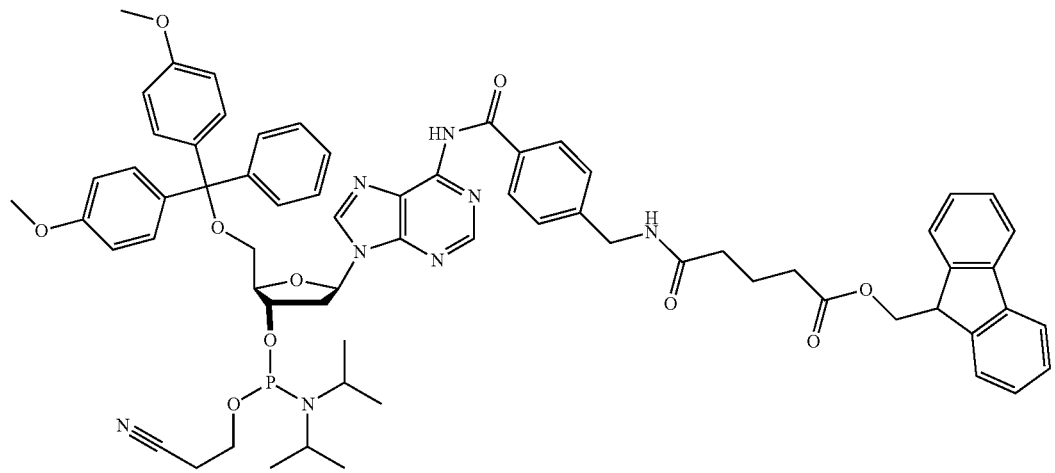

Structural Formula (5)

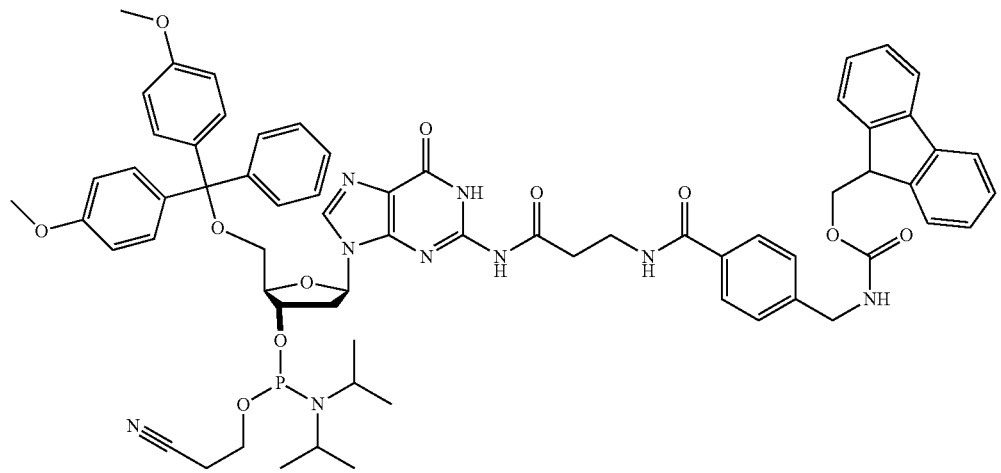

<Manufacture of Functional Molecule Synthesizing Amidite>

The method for manufacturing a functional molecule synthesizing amidite according to the present invention is not subjected to any particular limitations and may be appropriately selected according to the application. For example, it can be manufactured by any of the synthesizing methods described in Examples.

<Manufacture of Functional Molecule>

The functional molecule synthesizing amidite according to the present invention can suitably be used for manufacturing the functional molecule according to the present invention.

The method for manufacturing a functional molecule using the functional molecule synthesizing amidite according to the present invention is not subjected to any particular limitations and may be appropriately selected according to the application. A specific example of the manufacturing method is to use monomers of a functional molecule synthesizing amidite by means of diester method, triester method, phosphoroamidite method, H-phosphonate method or thiophosphite method for the preparation of oligomers such as dimers or trimers for the functional molecule synthesizing amidite, followed by polymerization of the oligomers. The method for polymerizing the oligomers for the purpose of the present invention is not subjected to any particular limitations and may be appropriately selected according to the application. A specific example is using a DNA synthesizer (DNA automatic synthesizer).

Specific examples of oligomers for the functional molecule synthesizing amidite according to the present invention include, but not limited to, those expressed by one of structural formulas (6) through (10) shown below.

Structural Formula (6)
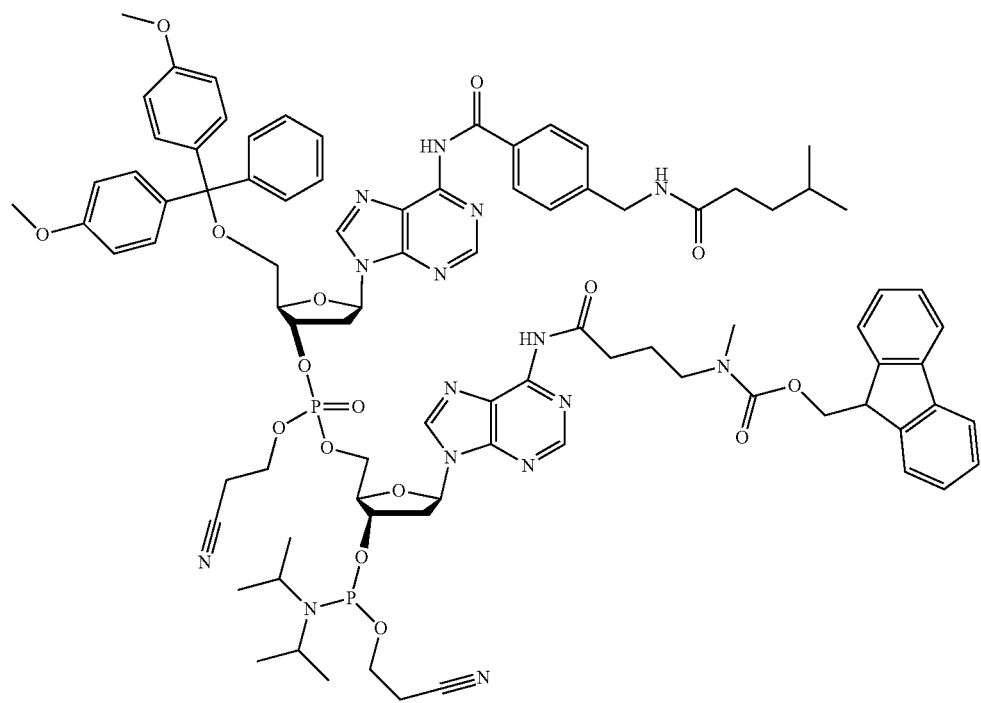
Structural Formula (7)
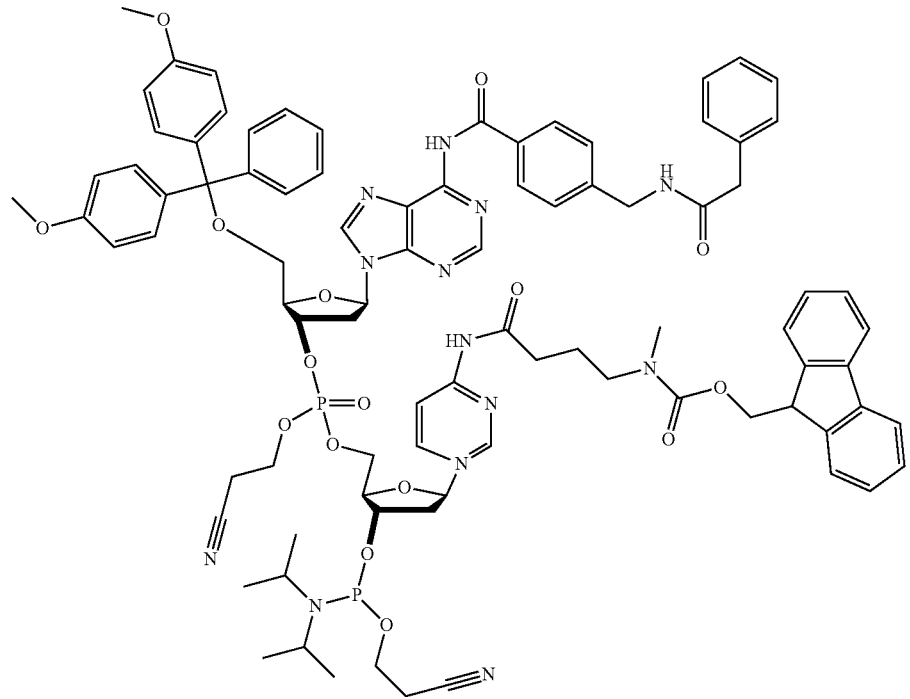

Structural Formula (8)
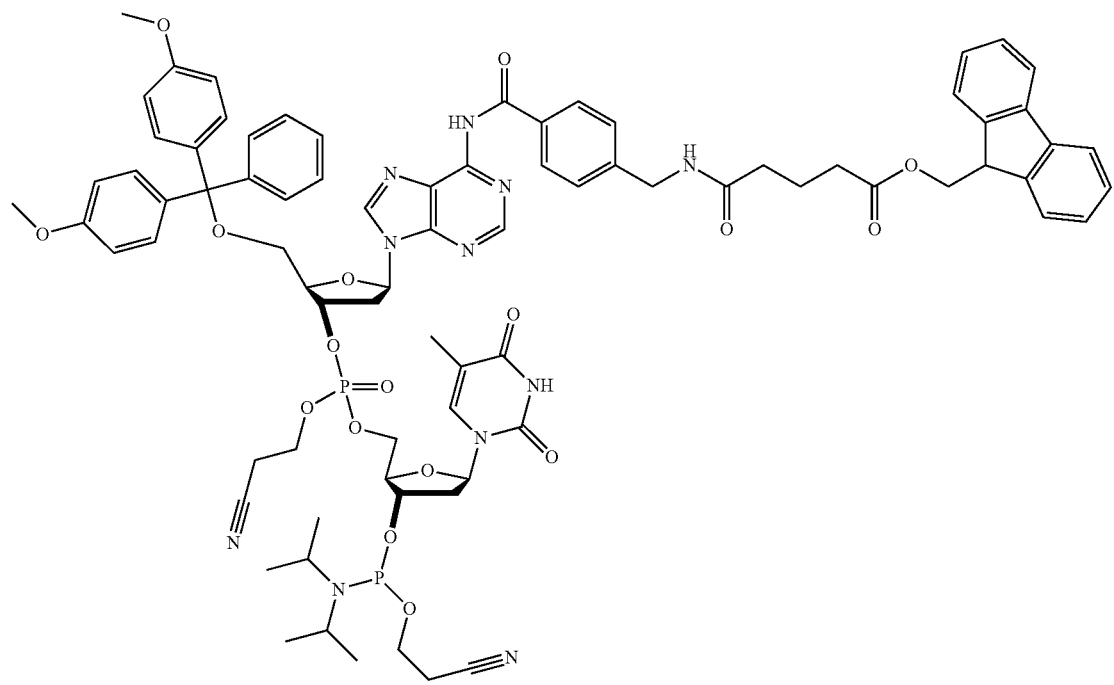
Structural Formula (9)
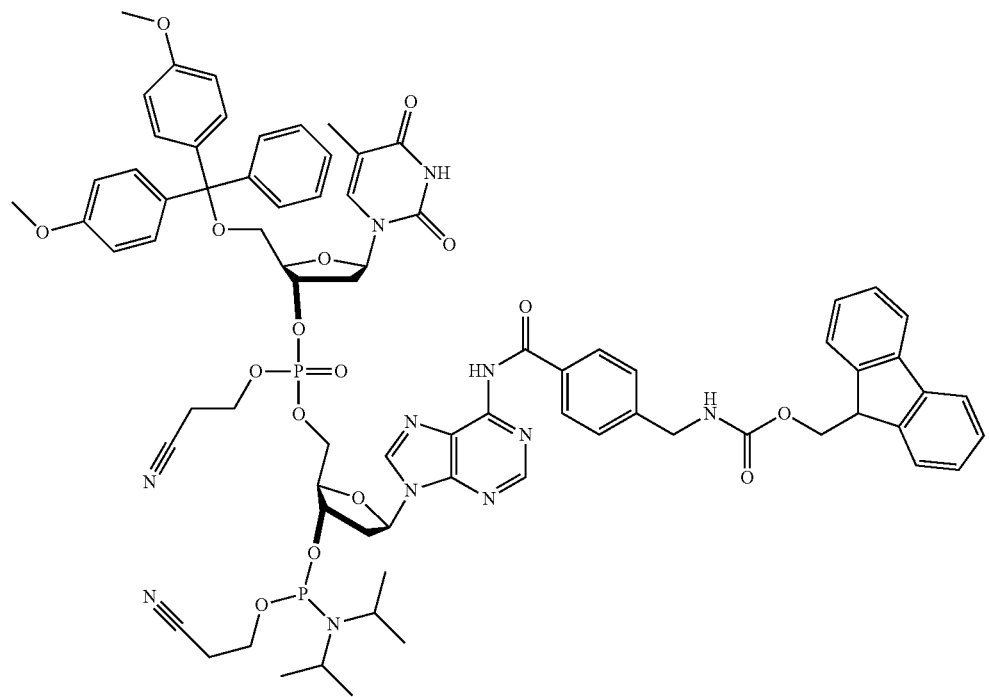

Structural Formula (10)

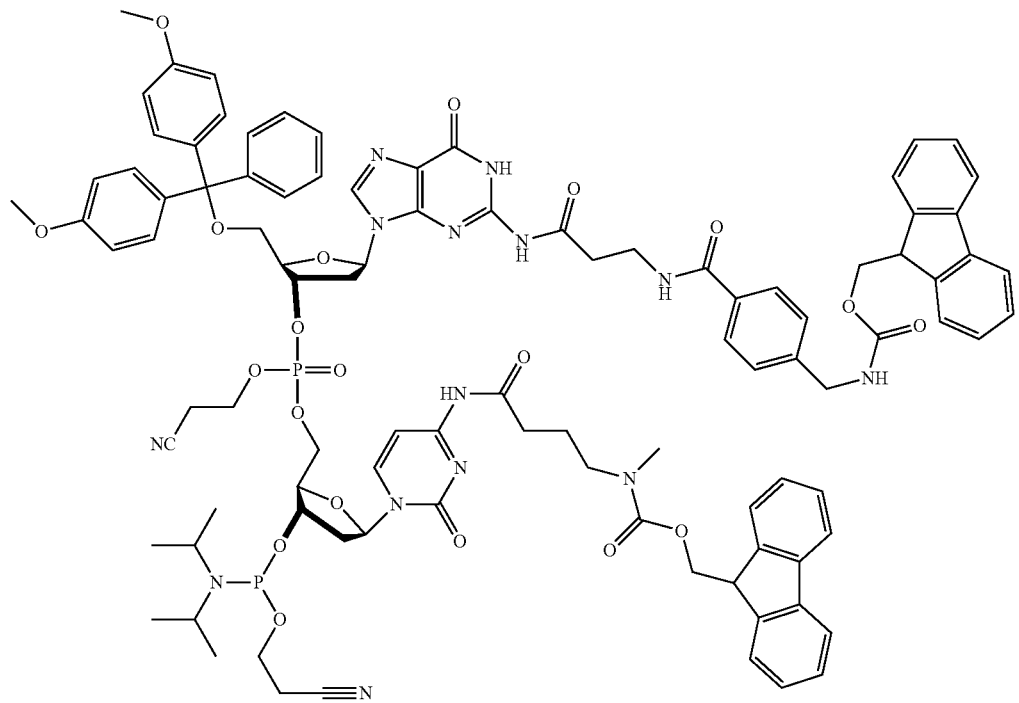

Upon manufacturing of the functional molecule according to the present invention, the protection group added to the functional molecule synthesizing amidite that is used for synthesizing the functional molecule is preferably removed after synthesizing the functional molecule by polymerization. Preferably, the deprotection is conducted under mild condition where the substituent is not removed as described above. As the protection group Z is removable under conditions where the substituent Y is not removed, the substituent that is indispensable for coupling the functional molecule to the target substance is not lost before the coupling to the target substance (at the time of manufacturing the functional molecule). Then, a functional molecule that can be coupled to a target substance can be stably manufactured.

The manufacture of the functional molecule according to the present invention is not subjected to any particular limitations and any additional amidite may be used according to the application so long as the functional molecule synthesizing amidite according to the present invention is used at least in a part of the manufacturing process. The additional amidite that can be used for the purpose of the present invention is not subjected to any particular limitations and may be appropriately selected according to the application. However, as described above, amidites whose protection group can be removed under mild conditions where the substituent of the functional molecule synthesizing amidite is not removed are preferably employed. Examples of such additional amidites include nucleic acid analogue synthesizing amidites described in Japanese Patent Application No. 2007-00576 (e.g., IIIa, IIIg and IIIc shown in Examples, which will be described hereinafter).

<Effects>

The functional molecule synthesizing amidite according to the present invention has a structure that allows the substituent to be easily removed from the base by ammonia treatment or the like. Therefore, when a functional molecule is synthesized by using such an amidite, the substituent can be removed after the functional molecule is coupled to a target substance. Thus, the present invention can provide a functional molecule for which PCR amplification can be realized with ease.

Additionally, since the substituent of a functional molecule synthesizing amidite according to the present invention is protected by a protection group and the protection group can be removed under mild conditions where the substituent is not removed, the substituent that is indispensable for coupling the functional molecule to the target substance is not lost before coupling to the target substance (at the time of deprotection in the process of manufacturing the functional molecule). Then, a functional molecule that can be coupled to a target substance can be stably manufactured.

(Target Substance Analysis Method)

The target substance analysis method according to the present invention has a random pool preparation step of synthesizing functional molecules (according to the present invention) by means of functional molecule synthesizing amidites for the preparation of a random pool of the functional molecules, a screening step of screening a functional molecule having affinity for a target substance from the random pool and an amplification step of amplifying the functional molecule having affinity for a target substance, further has one or more additionally steps if necessary, wherein the method further includes a removal step of removing the substituents of the functional molecule having affinity for the target substance.

"A random pool preparation step", "a screening step" and "an amplification step" and "one or more additional steps" as used herein for a target substance analysis method according to the present invention can be conducted appropriately by referring to, for example, International Publication No. WO/2003/078623. More specifically, they are conducted in a manner as described below.

<Random Pool Preparation Step>

The random pool preparation step that the target substance analysis method according to the present invention has is a step of synthesizing functional molecules from functional molecule synthesizing amidites for the preparation of a random pool of the functional molecules.

The terms "functional molecule synthesizing amidite," "functional molecule" and "method for synthesizing a functional molecule from functional molecule synthesizing amidite (method for manufacturing a functional molecule)" respectively have the same meanings as those described under the heading of functional molecule and the heading of functional molecule synthesizing amidite. The functional molecules-containing reaction products thus obtained as a result of synthesis of functional molecule can be used as a random pool of functional molecules without purification and isolation.

In the random pool preparation step, the protection group of the functional molecule synthesizing amidite is preferably removed after synthesizing a functional molecule. Then, deprotection is preferably realized under mild conditions where the substituent of the functional molecule synthesizing amidite is not removed as pointed out earlier. As the protection group Z is removed under such conditions, the substituent that is indispensable for coupling the functional molecule to the target substance is not lost before the coupling to the target substance (at the time of manufacturing the functional molecule). Then, the functional molecule that can be coupled to the target substance can be stably manufactured.

The method for removing the protection group is not subjected to any particular limitations and may be appropriately selected according to the types of the protection group and substituent. Examples of deprotection method include a treatment method to be conducted in an aprotic solvent by means of a bulky base and a method for using a tetrabutylammonium fluoride treatment. A single method may be used or alternatively two or more methods may be used in combination. Of the above-listed examples, the treatment method for treating in the aprotic solvent by means of bulky base is particularly preferable.

The "aprotic solvent," "bulky base" and "treatment method to be conducted in the aprotic solvent by means of bulky base" are not subjected to any particular limitations and may be appropriately selected according to the application. The meanings of the above expressions are the same as those described above under the heading of functional molecule synthesizing amidite.

<Screening Step>

The screening step is a step of screening a functional molecule having affinity for a desired target substance from the random pool the functional molecules manufactured in the random pool preparation step. The screening method is not subjected to any particular limitations and may be appropriately selected from the known methods according to the application. Examples of screening method include affinity chromatography, filter coupling, liquid/liquid division, filtration, gel shift assay and density-gradient centrifugation. These screening methods may be used singly or in combination. Of the above listed examples, affinity chromatography is particularly preferable.

The target substance is not subjected to any particular limitations and may be appropriately selected according to the application. Appropriate examples of target substance that can be used for the purpose of the present invention include proteins, lipoproteins, glycoproteins, polypeptides, lipids, polysaccharides, lipopolysaccharides, nucleic acids, hormones, endocrine disruptors, cells, viruses, drugs and composites thereof.

<Removal Step>

The removal step is a characteristic step of a target substance analysis method according to the present invention that is conducted before the amplification step, which will be described hereinafter. Substituents are removed from a functional molecule screened out in the screening step. By removing substituents before the amplification step, the functional molecule becomes to have a structure similar to that of naturally occurring nucleic acid, allowing it to be readily amplified by PCR or the like.

The method of removing substituents is not subjected to any particular limitations and may be appropriately selected according to the types of substituents and the like. Examples of the removal method include treatment by ammonia, treatment by alkali such as NaOH, treatment by hydrofluoric acid and fluoride, treatment by hydrazine, and treatment by irradiation of light, of which treatment by ammonia is preferable. A single treatment may be used or alternatively two or more treatments may be used in combination.

The "treatment by ammonium" is not subjected to any particular limitations and may be appropriately selected according to the application. The description of the treatment by ammonia given under the heading of functional molecule is applicable.

As a result of substituent removal, a substituent of some other type may be bonded to the position of removal. However, such a group may be left there so long as it does not interfere with the progress of PCR or the like and the functional molecule can be amplified.

—Combination of Deprotection Method for Removing Protection Group and Substituent Removal Method—

The combination of a deprotection method to be used in the random pool preparation step and a removal method to be used in the removal step is not subjected to any particular limitations and may be appropriately selected according to the structure of the functional molecule synthesizing amidite to be used and so on so long as the deprotection method can remove the protection group without eliminating substituents and the removal method can eliminate remaining substituents, and may be selected appropriately. Examples of such combination include a combination of a deprotection method that is a treatment method to be conducted in a aprotic solvent by means of a bulky base (e.g., DBU treatment in acetonitrile) and a removal method that is a method involving an ammonia treatment, a combination of a deprotection method that is a method for using a tetrabutylammonium fluoride treatment and a removal method that is a method involving irradiation of light.

The same method can be employed for the deprotection method and removal method when the deprotection process can be conducted under mild conditions where the substituent is not removed for instance by adjusting the temperature, the time and other reaction conditions.

<Amplification Step>

The amplification step is a step of amplifying the functional molecule for the purpose of sequencing the functional molecules screened in the screening step. The amplification conditions such as those of PCR can be determined very easily because the substituents of the functional molecule have been removed in the previous removal step. Thus the functional molecule has a structure similar to that of naturally occurring nucleic acid.

Therefore, the amplification method is not subjected to any particular limitations so long as it can increase the number of oligonucleotides of the object functional molecule and may be selected from the known methods of the technical field. Examples of amplification method include PCR (polymerase chain reaction), LCR (ligase chain reaction) method, 3SR (self-sustained sequence replication), SDA (strand displacement amplification), RT-PCR, ICAN method, and LAMP method. These methods may be used singly or in combination.

The method for sequencing the functional molecule is not subjected to any particular limitations and may be selected from methods known in the art. Examples of sequencing methods include the use of a DNA sequencer (automatic DNA sequencer) involving the use of any of the gene cloning method, chain terminator method, Sanger method and dideoxy method. These methods may be used singly or in combination.

<Additional Step>

The additional step that can be used for the purpose of the present invention is not subjected to any particular limitations and may be selected appropriately according to the application. A translation step may be used as an additional step.

The translation step is a step where the base sequence of the functional molecule that is determined in the amplification step is translated in order to identify the structure of the functional molecule having affinity for the target substance. Such translation can be realized typically by referring to International Publication No. WO/2003/078623.

For example, the identity of the substituent introduced to an oligomer, which may be a dimer, trimer or the like, of the functional molecule synthesizing amidite is defined in advance typically using a correspondence table that shows the correspondence of the base sequences of oligomers and the types of substituents. Thereafter, the functional molecule obtained by polymerizing the oligomer is coupled to the target substance and the functional molecule showing affinity for the target substance is screened. Subsequently, the substituents are removed from the functional molecule, followed by PCR amplification and sequencing (for determining the base sequence). Then, from the sequencing results, the types of the substituents introduced to the functional molecule can be confirmed by referring to the correspondence table. Thereby, replication of the functional molecule having affinity for the target substance can be made possible.

<Effects>

Since the target substance analysis method according to the present invention has a removal step of removing substituents of a functional molecule having affinity for the target substance before the amplification step, the functional molecule is similar in structure to naturally occurring nucleic acid in the amplification step; therefore, the functional molecule can be amplified with ease typically by PCR and its base sequence can be checked, confirmed and analyzed.

Additionally, the target substance analysis method according to the present invention removes the protection group of the functional molecule synthesizing amidite under the conditions where the substituent is not removed, preferably in the random pool preparation step. Therefore, the substituent that participates in the coupling to the target substance stably remains under the condition of being exposed to the surface of the functional molecule in the screening step. Thus, the functional molecule can be stably coupled to the target substance.

Thus, with the target substance analysis method according to the present invention, the protection group and substituent are removed in two separate stages (1st stage: removal of protection group in the random pool step, 2nd stage: removal of substituent in the removal step) so that the target substance can be analyzed stably and efficiently as a whole.

<Applications>

The functional molecule, functional molecule synthesizing amidite and target substance analysis method according to the present invention can find suitable applications in various fields including drugs, drug delivery and biosensors, as well as in controlling of gene expression level, overcoming diseases caused by abnormal genes, elucidation of the function of a protein translated from gene and development of reaction catalysts. For example, it may be possible to provide a multifunctional medicine and a substance that operates for high-precision drug delivery by identifying a molecule having affinity for a protein that participates in a specific metabolic system. It may be possible to control the expression levels of a series of genes by identifying a molecule having affinity for a specific DNA sequence in order to elucidate the interactions of gene products. Furthermore, it may be possible to efficiently advance a multi-state reaction that produces unstable intermediary reaction products by identifying a molecule having affinity for a molecule mimicking a reaction intermediate.

EXAMPLES

Now, the present invention will be described further by way of Examples, although the examples shown below by no means limit the scope of the present invention.

Example 1

Synthesis of Functional Molecule Synthesizing Amidite

Functional molecule synthesizing amidites according to the present invention ($IX_{Lys}$ (structural formula (1)), $IX_{Leu}$ (structural formula (2)), $IX_{Phe}$ (structural formula (3)), $IX_{Glu}$ (structural formula (4)), and XVI (structural formula (5)) and amidite dimers ($XII_{Leu}$ (structural formula (6)), $XII_{Phe}$ (structural formula (7)), $XII_{Glu}$ (structural formula (8)), $XII_{Lys}$ (structural formula (9)) and XIX (structural formula (10))) prepared by using the functional molecule synthesizing amidites were synthesized in a manner shown below.

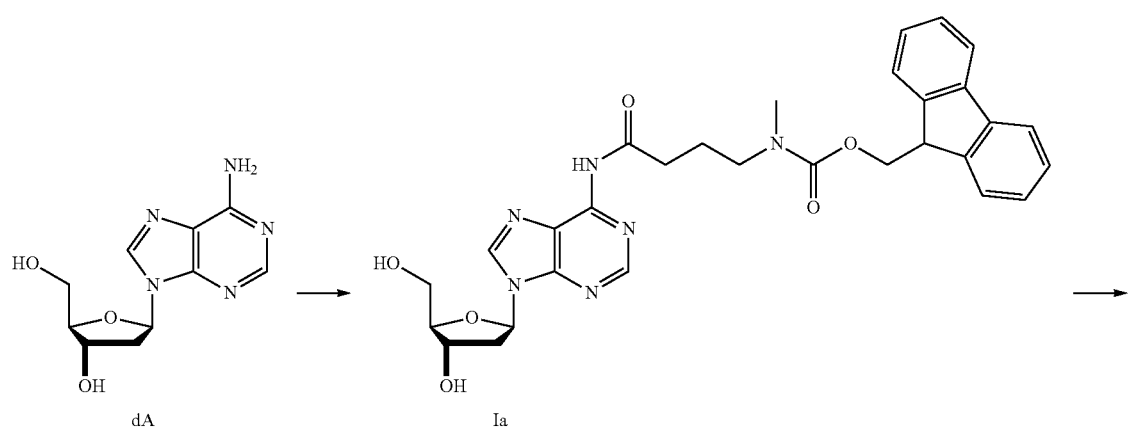

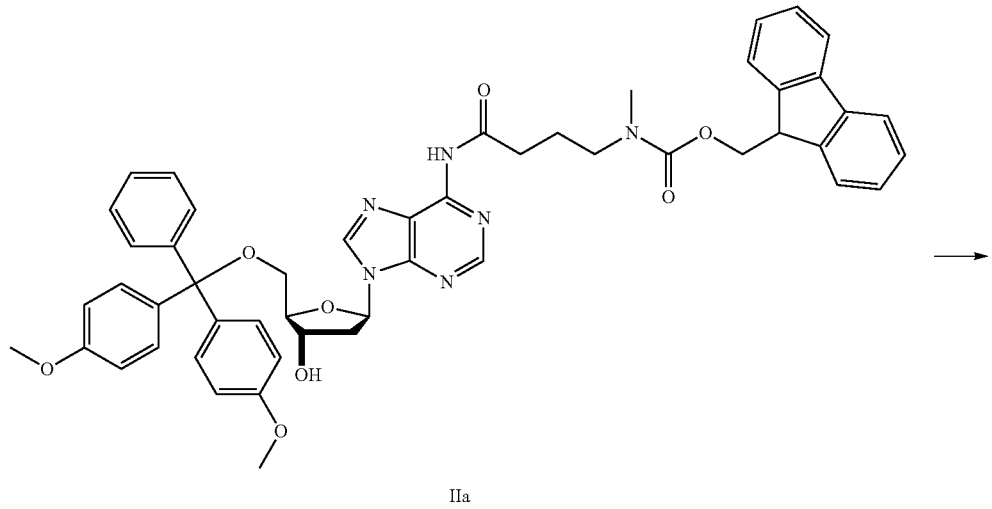
IIa
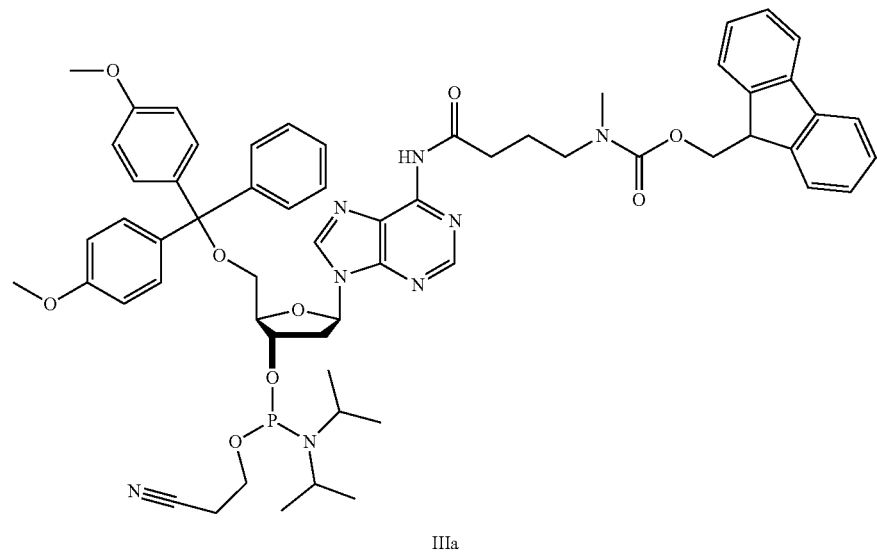
IIIa
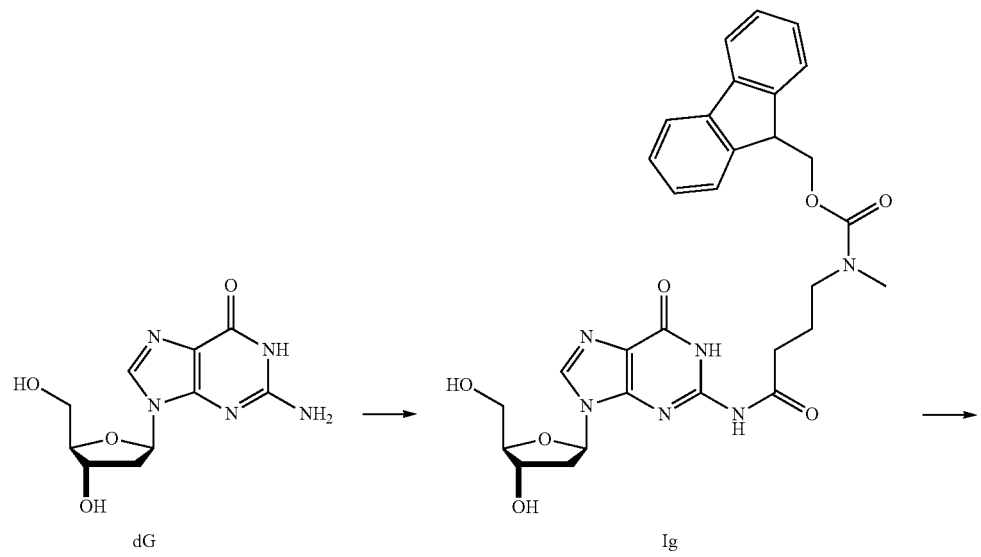
dG → Ig

-continued
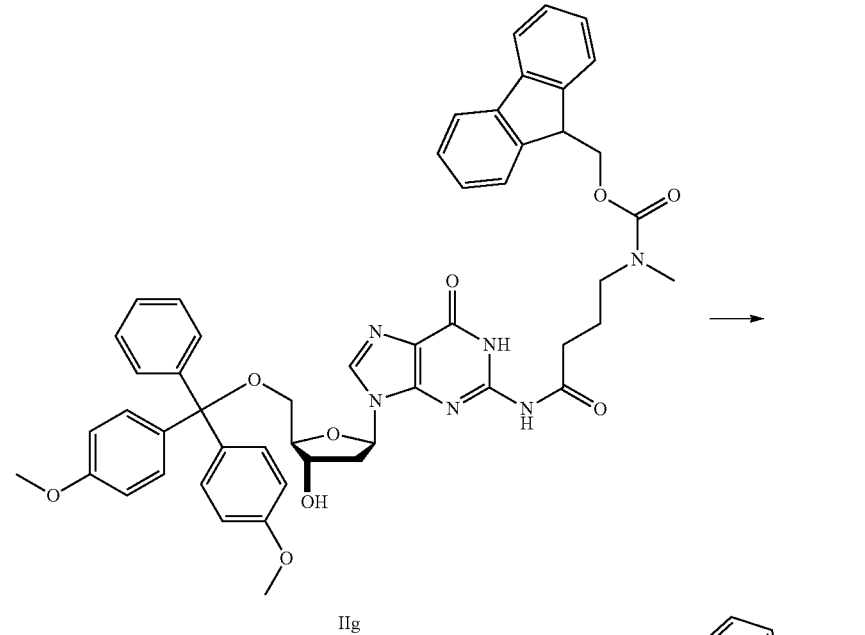
IIg
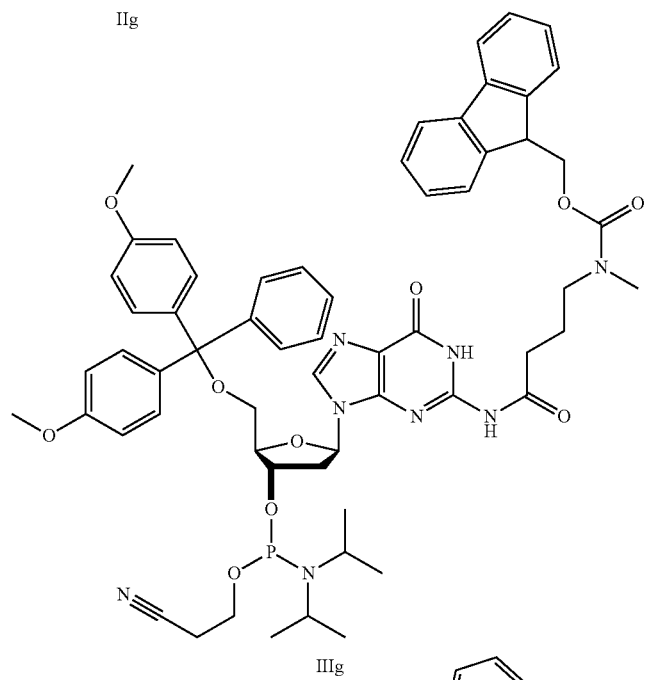
IIIg
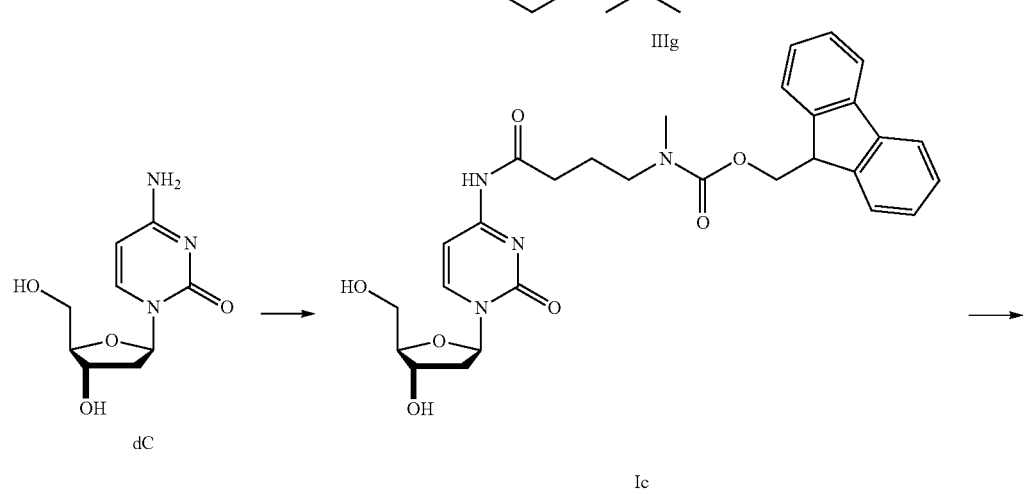
dC Ic

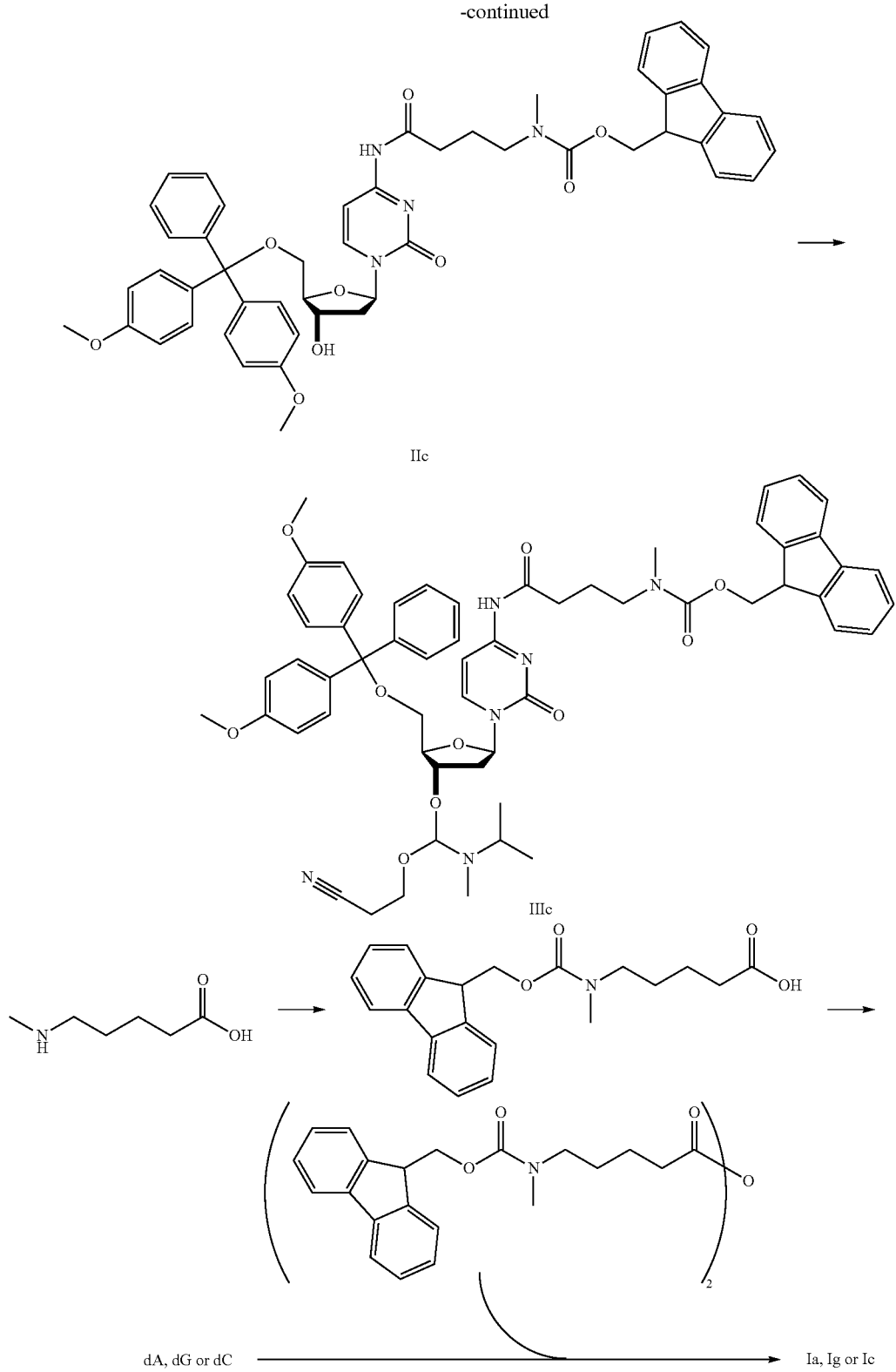

<Synthesis of Ia, Ig and Ic>

7.68 g (50 mmol) of N-methylaminobutyrate hydrochloride was dissolved in 50 mL of water and 4.20 g (50 mmol) of NaHCO₃ was added thereto and agitated for 10 minutes. Then, 13.49 g (40 mmol) of 9-fluorenylmethyl succinimidyl carbonate, 100 mL of acetonitrile and 0.14 g (0.4 mmol) tetrabutylammonium hydrogen sulfate were added to the solution and agitated at room temperature for 2 days. After concentrating the solution under reduced pressure, it was diluted by methylene chloride and washed with water. The methylene chloride solution was then concentrated under reduced pressure and subjected to azeotropy by means of dehydrated acetonitrile and then by means of dehydrated methylene chloride. The residue was dissolved in 200 mL of dehydrated methylene chloride and 4.13 g (20 mmol) of N,N'-dicyclohexylcarbodiimide was added and agitated at room temperature for 2 hours. After filtering the undissolved substance, the solution was concentrated under reduced pressure to obtain residue A.

Dioxynucleoside (dA, dG or dC, 20 mmol) was suspended in dehydrated pyridine and an operation of concentrating it under reduced pressure was repeated three times. The residue was suspended in 100 mL of dehydrated pyridine and 8.45 mL (66 mmol) of trimethylchlorosilane was added thereto at 0° C. Then, the mixture solution was agitated at room temperature for 1 hour and subsequently cooled to 0° C. again before it was introduced to the residue A. The reaction mixture was agitated at room temperature for 2 hours. Then, 20 mL of water was added to the reaction mixture while the latter was being cooled with ice and the solution was agitated at room temperature overnight. The solution was diluted by methylene chloride and washed with water. The methylene chloride solution was concentrated under reduce pressure and the residue was purified by medium pressure chromatography (dichloromethane-ethanol 19:1→4:1) to obtain target products Ia, Ig and Ic in amounts of 6.91 g (60%), 9.43 g (80%) and 8.80 g (80%), respectively.

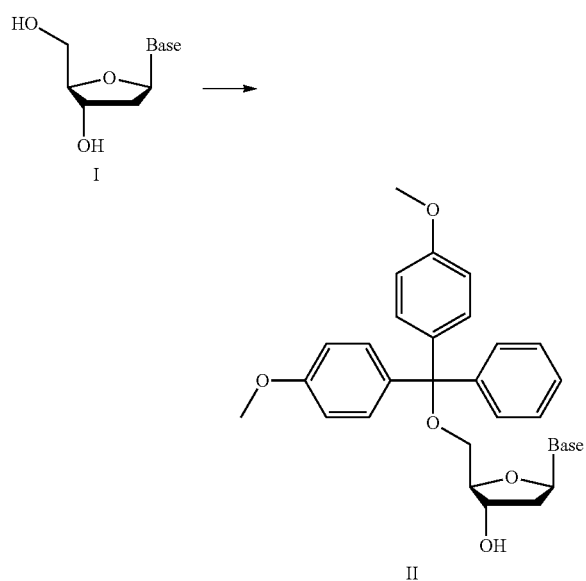

<Synthesis of IIa, IIg and IIc>

Each of Ia, Ig and Ic was dissolved in 10 mmol of dehydrated pyridine and an operation of concentrating the solution under reduced pressure was repeated three times. The residue was dissolved in 50 mL of dehydrated pyridine and 3.36 g (10.5 mmol) of 4,4'-dimethoxytritylchloride was added to the solution while being cooled with ice. The solution was agitated at room temperature for 4 hours. Subsequently, 10 mL of methanol was added and the solution was agitated for 30 minutes. Then, the solution was concentrated under reduced pressure, diluted by methylene chloride and washed with water. The methylene chloride solution was concentrated under reduced pressure and the residue was purified by medium pressure chromatography (dichloromethane-ethanol 98:2→9:1). In this way, target products IIa, IIg and IIc were obtained in amounts of 7.92 g (91%), 8.35 g (94%) and 7.64 g (90%), respectively.

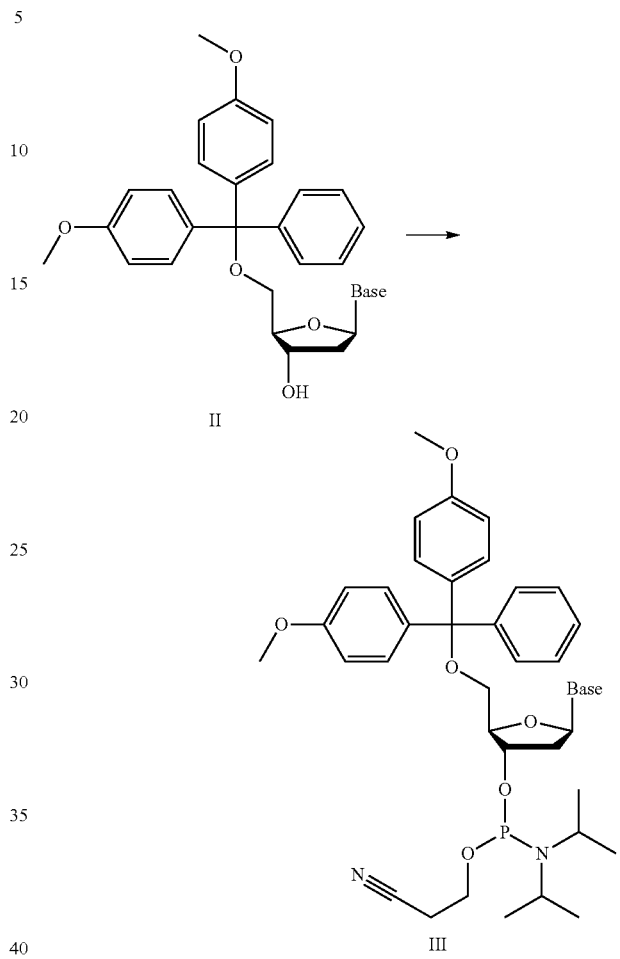

<Synthesis of IIIa, IIIg and IIIc>

Each of IIa, IIg and IIc was dissolved in 5 mmol of a mixture solution of dehydrated acetonitrile and dehydrated dichloromethane and an operation of concentrating the solution under reduced pressure was repeated three times. The residue was dissolved in 20 mL of dehydrated dichloromethane and 30.5 mg (0.25 mmol) of dimethylaminopyridine and 1.05 mL (6.0 mmol) of diisopropylethylamine were added to the solution while being cooled with ice. Then, 5 ml methylene chloride solution of 1.23 mL (5.5 mmol) of 2-cyanoethyldiisopropylchlorophosphoroamidite was added over more than 15 minutes. The mixture solution was agitated at 0° C. (IIa, IIc) or at room temperature (IIg) for 2 hours. Subsequently, 5 mL of methanol was added and the solution was agitated for 30 minutes. Then, the solution was concentrated under reduced pressure, diluted by ethyl acetate and washed with water. The ethyl acetate solution was concentrated under reduced pressure. The residue was dissolved in 25 mL of ethyl acetate and added dropwise in 500 mL of hexane at −30° C. over 15 minutes. The insoluble was removed by filtration. The filtered product was washed with cold hexane and the solvent was removed from the product under reduced pressure. In this way, target products IIIa, IIIg and IIIc were obtained in amounts of 5.22 g (97%), 5.22 g (96%) and 4.70 g (94%), respectively.

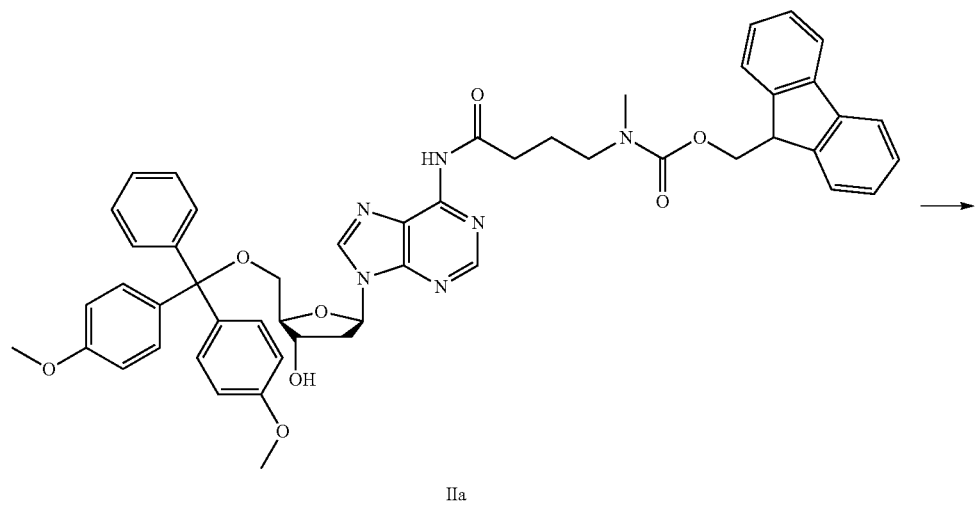
IIa
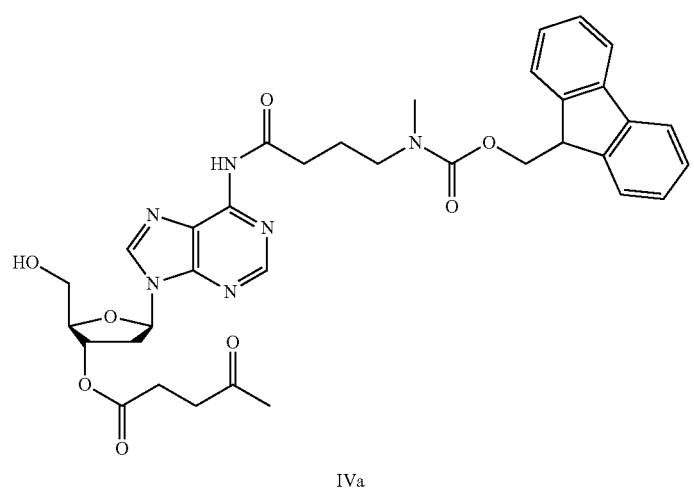
IVa
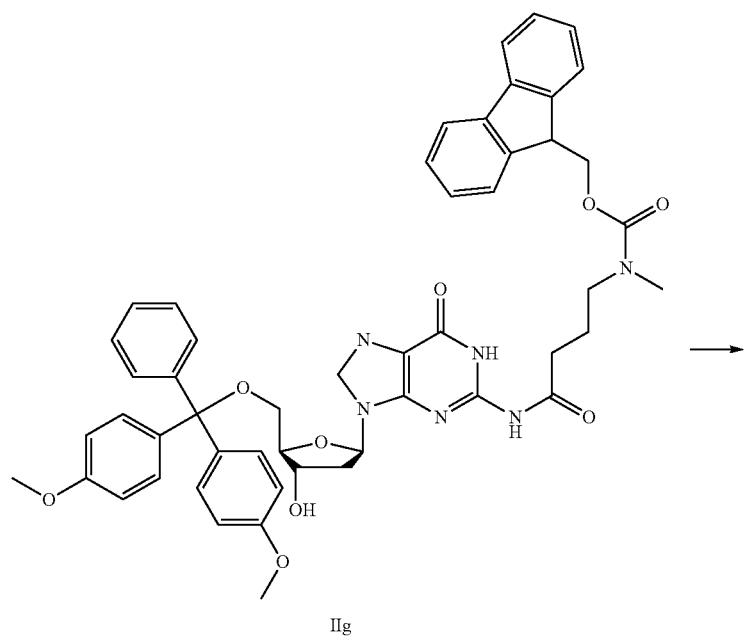
IIg

-continued
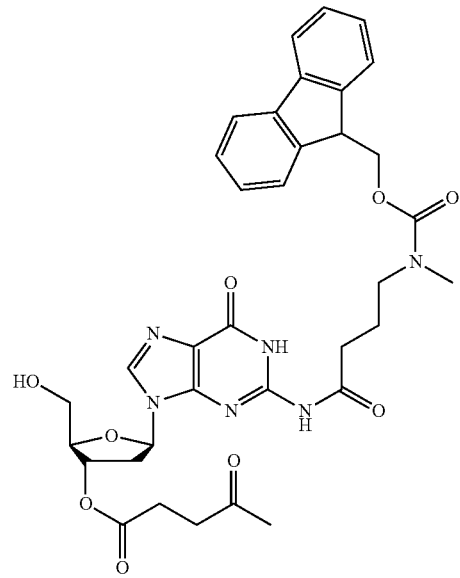
IVg
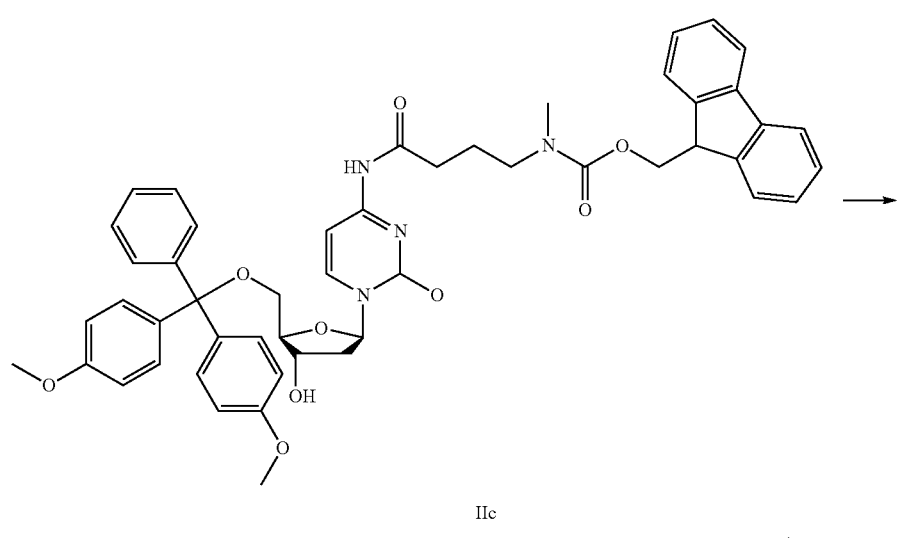
IIc
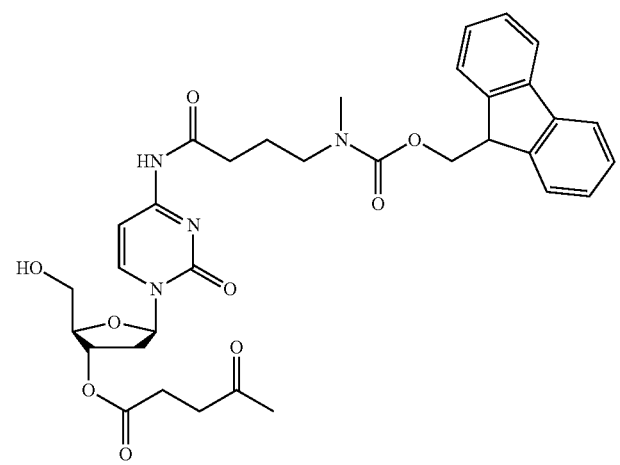
IVc

<Synthesis of IVa, IVg and IVc>

Each of IIa, IIg and IIc was dissolved in 5 mmol of dehydrated dioxane and an operation of concentrating the solution under reduced pressure was repeated three times. The residue was dissolved in 25 mL of dehydrated dioxane and 48.9 mg (0.4 mmol) of dimethylaminopyridine, 2.06 g (10 mmol) of dicyclohexylcarbodiimide and 1.02 mL (10 mmol) of levulinic acid were added to the solution at 10° C. and the mixture solution was agitated at room temperature for 2 hours. Then, 2 mL of methanol was added to the reaction solution and agitated for 30 minutes. The insoluble was removed by filtration and the filtered solution was concentrated under reduced pressure, diluted with dichloromethane and washed with water. The dichloromethane solution was concentrated under reduced pressure and the residue was suspended in 5 mL of dichloromethane. The insoluble was removed by filtration and the filtered solution was concentrated under reduced pressure. The residue was dissolved in 100 mL of dehydrated dichloromethane and 2 mL of trifluoroacetic acid was added while being cooled with ice. The mixture solution was agitated at 0° C. for 2 hours and 10 mL of dehydrated methanol and 5 mL of dehydrated pyridine were added thereto. The reaction mixture was agitated at room temperature overnight. Then, the reaction mixture was washed with water and the dichloromethane solution was concentrated under reduced pressure. The residue was purified by medium pressure chromatography (dichloromethane-ethanol 98:2→4:1). In this way, target products IVa, IVg and IVc were obtained in amounts of 3.00 g (89%), 2.96 g (86%) and 2.95 g (91%), respectively.

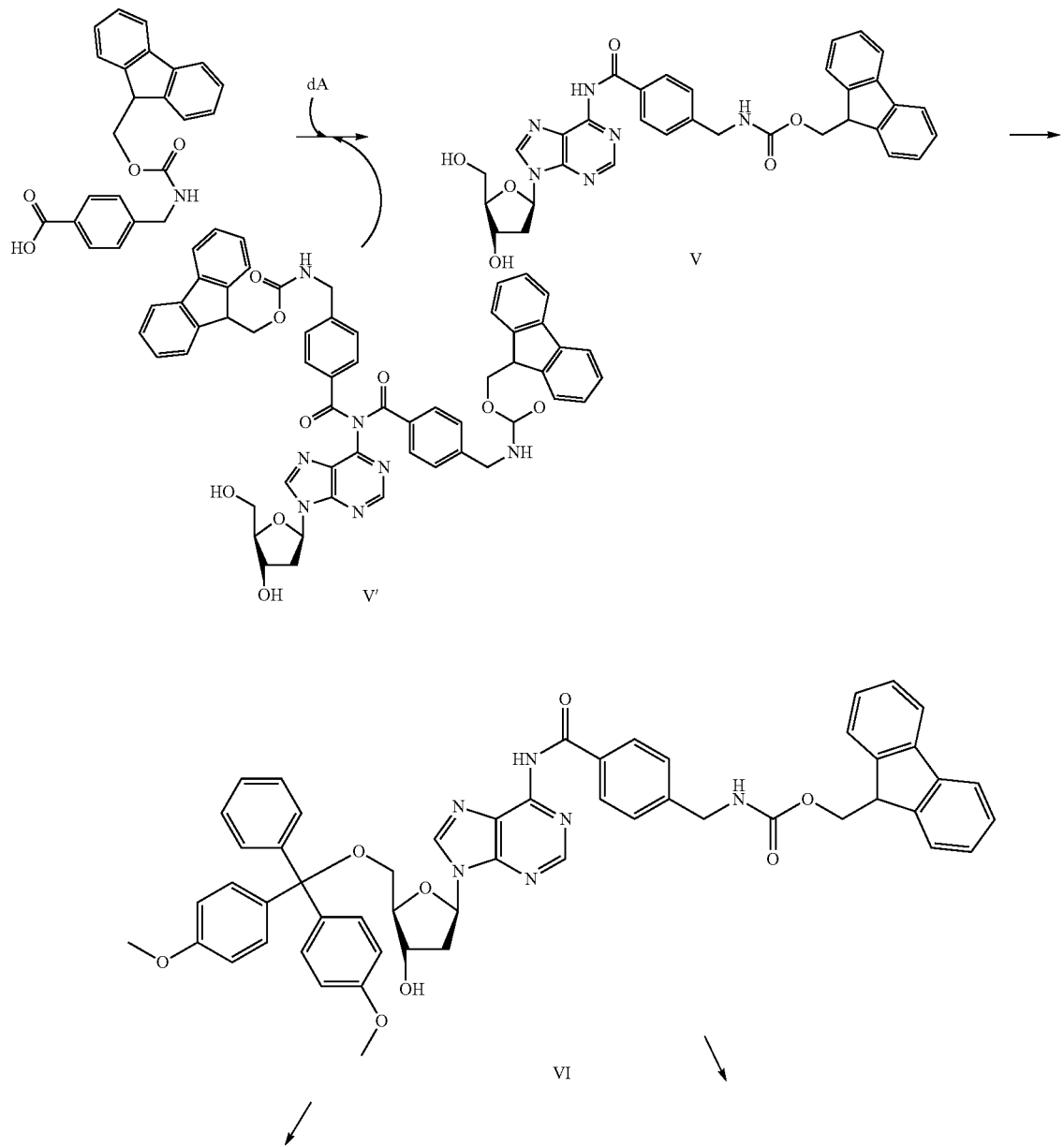

-continued

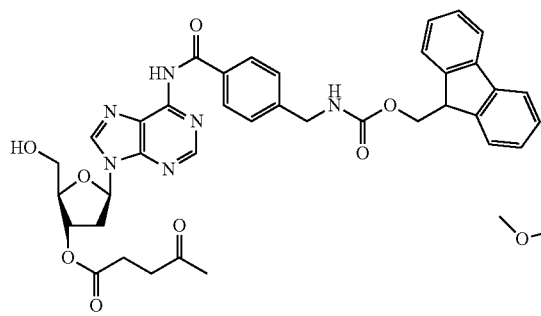

VII

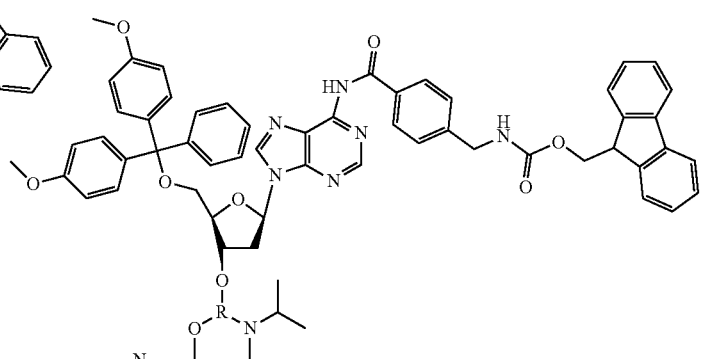

IX$_{Lys}$

<Synthesis of V>

28.0 g (75 mmol) of 4-(FMOC-aminomethyl)benzoic acid was suspended in 375 mL of dehydrated dichloromethane and 12.9 mL (150 mmol) of oxaryl chloride and 0.12 mL (1.5 mmol) of dimethylformamide were added thereto in an argon atmosphere and the mixture was agitated at room temperature for 7 hours. The reaction solution was concentrated under reduced pressure. Dehydrated toluene was added to the residue and the mixture solution was concentrated under reduced pressure to obtain residue A.

24.2 g (90 mmol) of dioxyadenosine monohydrate was dissolved in dehydrated pyridine and an operation of concentrating the suspension under reduced pressure was repeated three times. 38.0 mL (297 mmol) of trimethylchlorosilane was added at 0° C. and the mixture solution was agitated at room temperature for 1 hour and then cooled again to 0° C. before the solution was introduced to the residue A. The temperature of the reaction mixture was raised to the level of room temperature over more than 4 hours and the mixture was agitated at room temperature overnight. Then, 75 mL of water was added while being cooled with ice and the mixture solution was agitated at room temperature for 8 hours. The solution was concentrated under reduced pressure. The residue was diluted with methylene chloride and washed with water. The methylene chloride solution was concentrated under reduced pressure and the residue was purified by medium pressure chromatography (dichloromethane-ethanol 9:1→4:1) to obtain 15.5 g (34%) of target product V, or 18.2 g of target product V containing a small quantity of impurity that seemed to be substance V', with a primary yield of 74%.

<Synthesis of VI>

15.5 g (25.5 mmol) of V was dissolved in dehydrated pyridine and an operation of concentrating the solution under reduced pressure was repeated three times. The residue was dissolved in 130 mL of dehydrated pyridine and 9.09 g (26.8 mmol) of 4,4'-dimethoxytritylchloride was added to the solution while being cooled with ice. The solution was agitated at room temperature for 4 hours. Subsequently, 25 mL of methanol was added and the solution was agitated for 30 minutes. Then, the solution was concentrated under reduced pressure, diluted by ethyl acetate and washed with water. The ethyl acetate solution was concentrated under reduced pressure and the residue was purified by medium pressure chromatography (ethylacetate-ethanol 39:1→19:1). In this way, target product VI was obtained in an amount of 21.3 g (92%).

VI was also obtained by 22.4 g from V containing a small quantity of V' in a similar manner. Thus, VI was obtained with a 2-stage yield of 64%.

<Synthesis of VII>

1.82 g (2.0 mmol) of VI was dissolved in dehydrated dioxane and an operation of concentrating the solution under reduced pressure was repeated three times. The residue was dissolved in 15 mL of dehydrated dioxane and 19.5 mg (0.16 mmol) of dimethylaminopyridine, 825 mg (4.0 mmol) of dicyclohexylcarbodiimide and 0.41 mL (4.1 mmol) of levulinic acid were added to the solution at 10° C. and the mixture solution was agitated at room temperature for 2 hours. Then, 2 mL of methanol was added to the reaction solution and agitated for 30 minutes. The insoluble was removed by filtration and the filtered solution was concentrated under reduced pressure, diluted with dichloromethane and washed with water. The dichloromethane solution was concentrated under reduced pressure and the residue was suspended in 2 mL of dichloromethane. The insoluble was removed by filtration and the filtered solution was concentrated under reduced pressure. The residue was dissolved in 40 mL of dehydrated dichloromethane and 0.8 mL of trifluoroacetic acid was added while being cooled with ice. The mixture solution was agitated at 0° C. for 2 hours and 4 mL of dehydrated methanol and 2 mL of dehydrated pyridine were added thereto. The reaction mixture was agitated at room temperature overnight. Then, the reaction mixture was washed with water and the dichloromethane solution was concentrated under reduced pressure. The residue was purified by medium pressure chromatography (dichloromethane-ethanol 98:2→9:1). In this way, target product VII was obtained in an amount of 1.15 g (82%).

<Synthesis of IX$_{Lys}$>

4.54 g (5 mmol) of VI was dissolved in dehydrated acetonitrile and an operation of concentrating the solution under reduced pressure was repeated three times. The residue was dissolved in 20 mL of dehydrated dichloromethane and 30.5 mg (0.25 mmol) of dimethylaminopyridine and 1.13 mL (6.5 mmol) of diisopropylethylamine were added to the solution while being cooled with ice. Then, 5 ml methylene chloride solution of 1.34 mL (6.0 mmol) of 2-cyanoethyldiisopropylchlorophosphoroamidite was added over more than 15 minutes. The mixture solution was agitated at 0° C. for 2 hours. Subsequently, 5 mL of methanol was added and the solution was agitated for 30 minutes. Then, the solution was concentrated under reduced pressure, diluted by dichloromethane and washed with water. The dichloromethane solution was concentrated under reduced pressure. The residue was dissolved in 60 mL of ethyl acetate and added dropwise in 500 mL of hexane at −30° C. The insoluble was removed by filtration. The filtered product was washed with cold hexane and the solvent was removed from the product under reduced pressure. In this way, target product IX$_{Lys}$ was obtained in an amount of 5.23 g (94%).

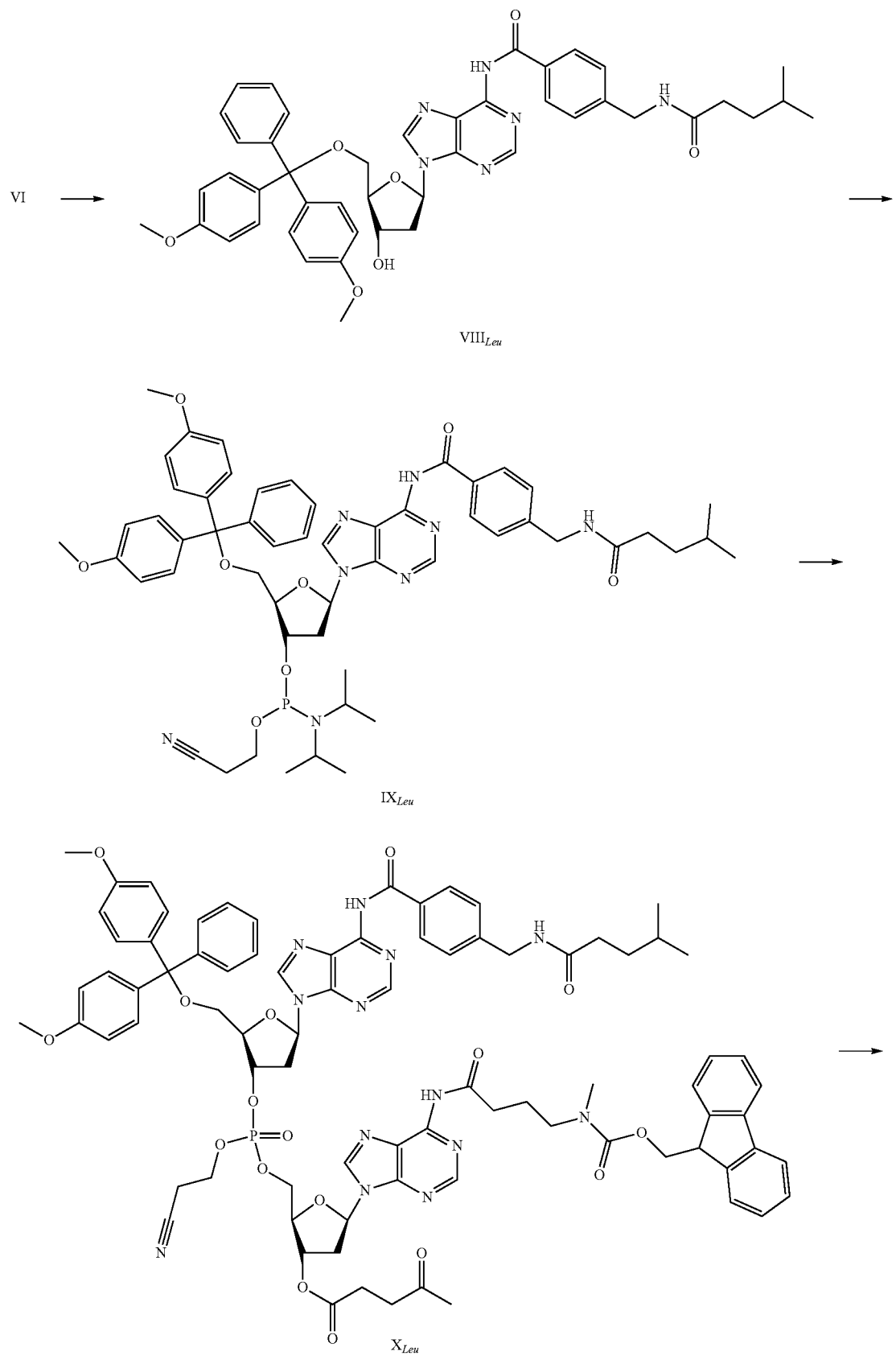

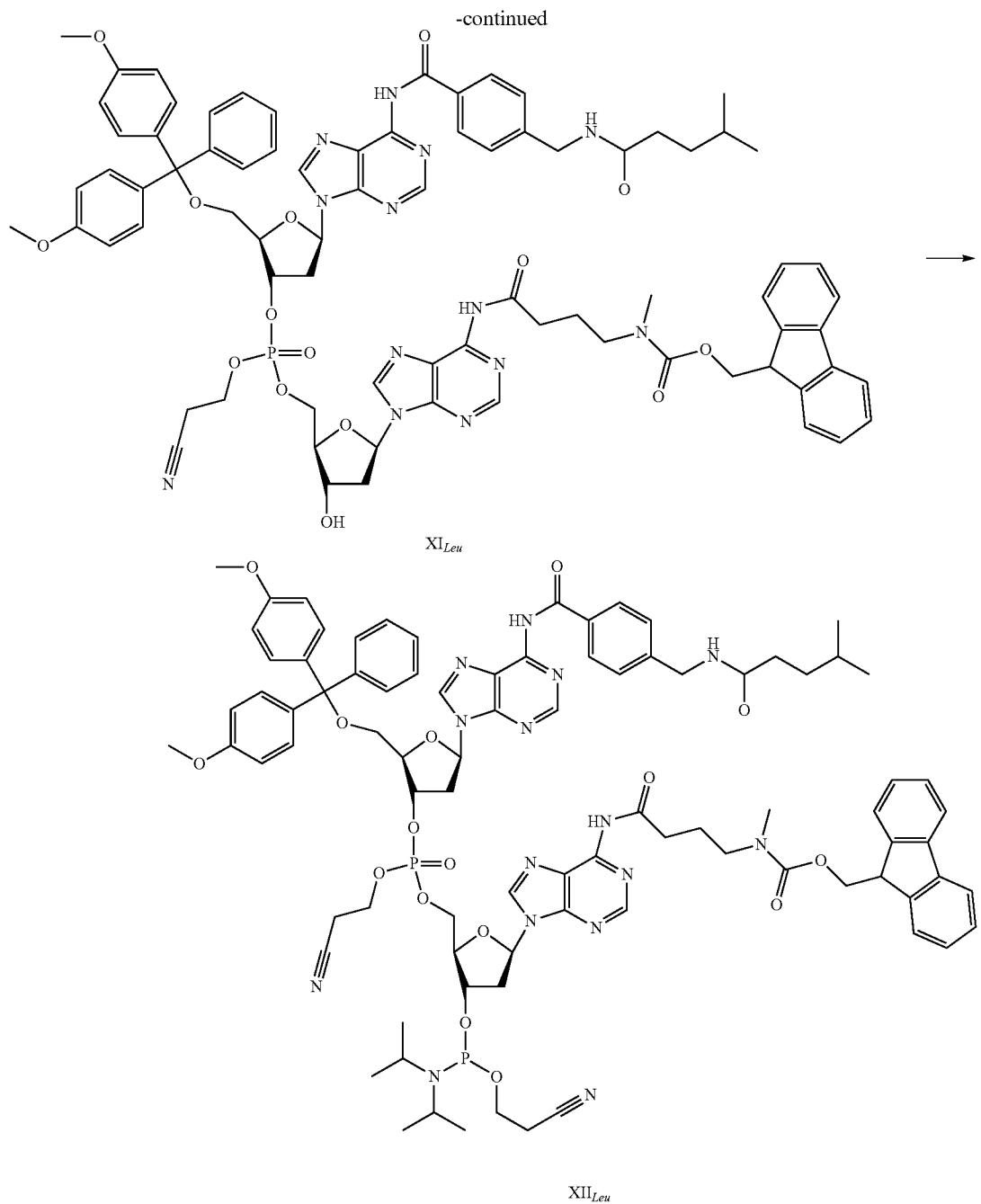

<Synthesis of VIII$_{Leu}$>

8.20 g (9.12 mmol) of VI was dissolved in 46 mL of dehydrated dichloromethane and 1.63 mL (10.9 mmol) of diazabicycloundecene was added to the solution while being cooled with ice. The solution was then agitated at room temperature for 3 hours to obtain reaction mixture A.

1.38 mL (10.9 mmol) of 4-methylvaleric acid was dissolved in 33 mL of dehydrated dichloromethane and 1.39 g (12.0 mmol) of N-hydroxysuccinic acid imide was added to the solution. Then, 2.37 g (11.5 mmol) of dicyclohexylcarbodiimide was also added to the solution while being cooled with ice and the solution was agitated at room temperature for 2 hours. The insoluble was removed by filtration and the filtered solution was added to the reaction mixture A. The reaction mixture was then agitated at room temperature for 4 hours. Subsequently, 5 mL of methanol was added to the solution, which was then agitated for 30 minutes. The reaction solution was diluted by dichloromethane and washed with water. The dichloromethane solution was concentrated under reduced pressure and the residue was purified by medium pressure chromatography (dichloromethane-ethanol 49:1→17:3). In this way, target product VIII$_{Leu}$ was obtained in an amount of 5.03 g (70%).

<Synthesis of IX$_{Leu}$>

3.92 g (5 mmol) of VIII$_{Leu}$ was dissolved in dehydrated acetonitrile and an operation of concentrating the solution under reduced pressure was repeated three times. The residue was dissolved in 20 mL of dehydrated dichloromethane and 30.5 mg (0.25 mmol) of dimethylaminopyridine and 1.13 mL (6.5 mmol) of diisopropylethylamine were added to the solution while being cooled with ice. Then, 5 ml methylene chloride solution of 1.34 mL (6.0 mmol) of 2-cyanoethyldiisopropylchlorophosphoroamidite was added over more than 15 minutes. The mixture solution was agitated at 0° C. for 2 hours. Subsequently, 5 mL of methanol was added and the solution was agitated for 30 minutes. Then, the solution was concentrated under reduced pressure, diluted by dichloromethane and washed with water. The dichloromethane solution was concentrated under reduced pressure. The residue was dissolved in 60 mL of ethyl acetate and added dropwise in 500 mL of hexane at −30° C. The insoluble was removed by filtration. The filtered product was washed with cold hexane and the solvent was removed from the product under reduced pressure. In this way, target product $IX_{Leu}$ was obtained in an amount of 4.74 g (97%).

<Synthesis of $X_{Leu}$>

4.19 g (4.25 mmol) of $IX_{Leu}$ was dissolved in dehydrated acetonitrile and an operation of concentrating the solution under reduced pressure was repeated three times. The residue was dissolved in 21 mL of dehydrated acetonitrile to obtain solution A. 2.86 g (4.25 mmol) of IVa was dissolved into dehydrated acetonitrile and an operation of concentrating the solution under pressure was repeated three times. The residue was dissolved into 21 mL of dehydrated acetonitrile and added to the solution A. 1.49 g (21.3 mmol) of tetrazole was added to the reaction mixture and the mixture was agitated at room temperature for 1 hour. Subsequently, 2.1 mL of methanol was added to the mixture solution, which was then agitated for 30 minutes, diluted by dichloromethane and washed with water. The dichloromethane solution was concentrated under reduced pressure. The residue was dissolved into 89 mL of tetrahydrofuran, 26 mL of pyridine and 13 mL of water and 3.77 g (14.9 mmol) of iodine was added thereto. The mixture solution was then agitated at room temperature for 30 minutes. 380 mL of dichloromethane was added to the reaction mixture and then 9.37 g (74.3 mmol) of sodium sulfite was added thereto on ice. The mixture was agitated at room temperature for 15 minutes. Then, about 25 g of sodium sulfate was added to the reaction mixture, which was then agitated well. Subsequently, the insoluble was removed by filtration and the filtered solution was concentrated under reduced pressure. The obtained residue was purified by medium pressure chromatography (dichloromethane-ethanol 49:1→9:1). In this way, target product $X_{Leu}$ was obtained in an amount of 4.38 g (66%).

<Synthesis of $XI_{Leu}$>

4.18 g (2.66 mmol) of $X_{Leu}$ was dissolved into 27 mL of pyridine and 27 mL of a diluted solution (pyridine:acetic acid=3:2) of 1.29 mL (26.7 mmol) of hydrazine monohydrate was added thereto and the mixture solution was agitated at room temperature for 20 minutes. 26 mL of acetone was added to the solution while being cooled with ice and the solution was agitated at 0° C. for 10 minutes, diluted with dichloromethane and washed with water. The dichloromethane solution was concentrated under reduced pressure. The residue was purified by medium pressure chromatography (dichloromethane-ethanol 19:1→17:3). In this way, target product $XI_{Leu}$ was obtained in an amount of 3.05 g (79%).

<Synthesis of $XII_{Leu}$>

870 mg (0.59 mmol) of $XI_{Leu}$ was dissolved in a mixture solution of dehydrated acetonitrile and dehydrated dichloromethane and an operation of concentrating the solution under reduced pressure was repeated three times. The residue was dissolved in 6.0 mL of dehydrated dichloromethane and 3.6 mg (0.029 mmol) of dimethylaminopyridine and 139 μL (0.80 mmol) of diisopropylethylamine were added to the solution while being cooled with ice. Then, 158 mL (0.629 mmol) of 2-cyanoethyldiisopropylchlorophosphoroamidite was added. The mixture solution was agitated at 0° C. for 3 hours. Subsequently, 0.6 mL of methanol was added and the solution was agitated for 30 minutes. The reaction solution was diluted with ethyl acetate and washed with water. Then, the ethyl acetate solution was concentrated under reduced pressure. The residue was dissolved in 9 mL of ethyl acetate and added dropwise in 59 mL of hexane at −30° C. The insoluble was removed by filtration. The filtered product was washed with cold hexane and the solvent was removed from the product under reduced pressure. In this way, target product $XII_{Leu}$ was obtained in an amount of 885 mg (89%).

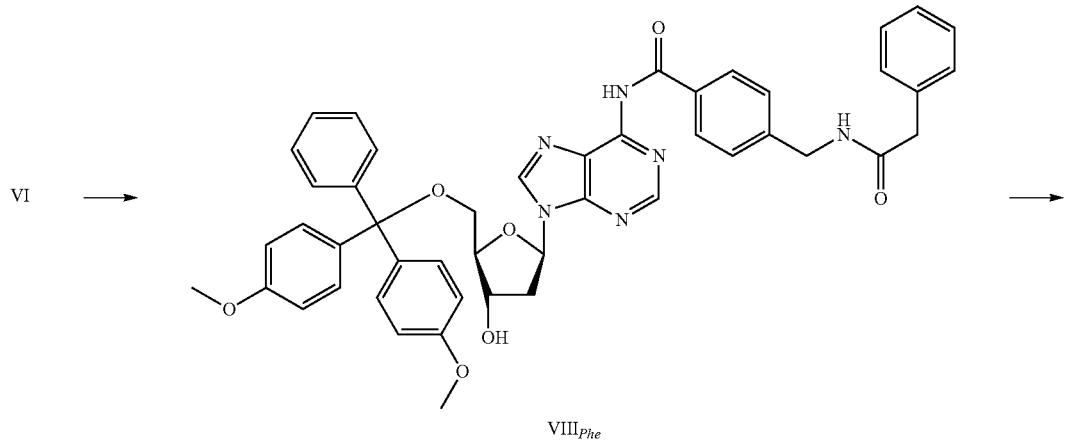

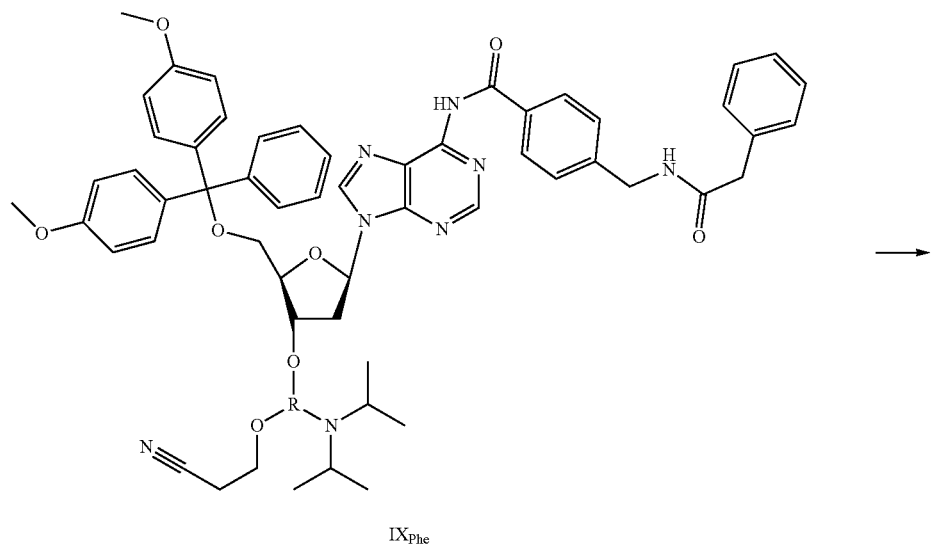
IX<sub>Phe</sub>
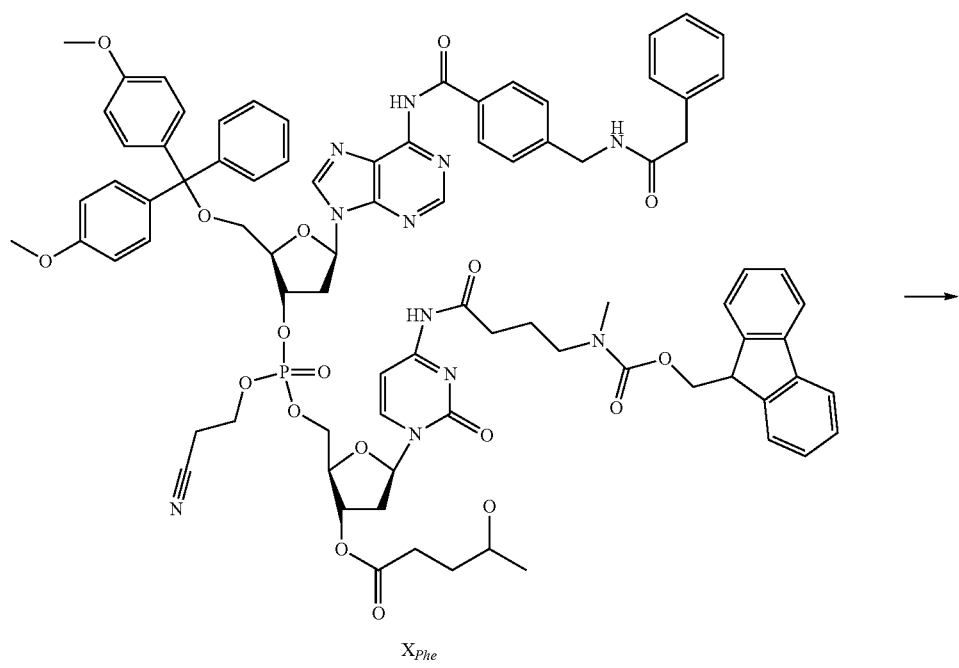
X<sub>Phe</sub>

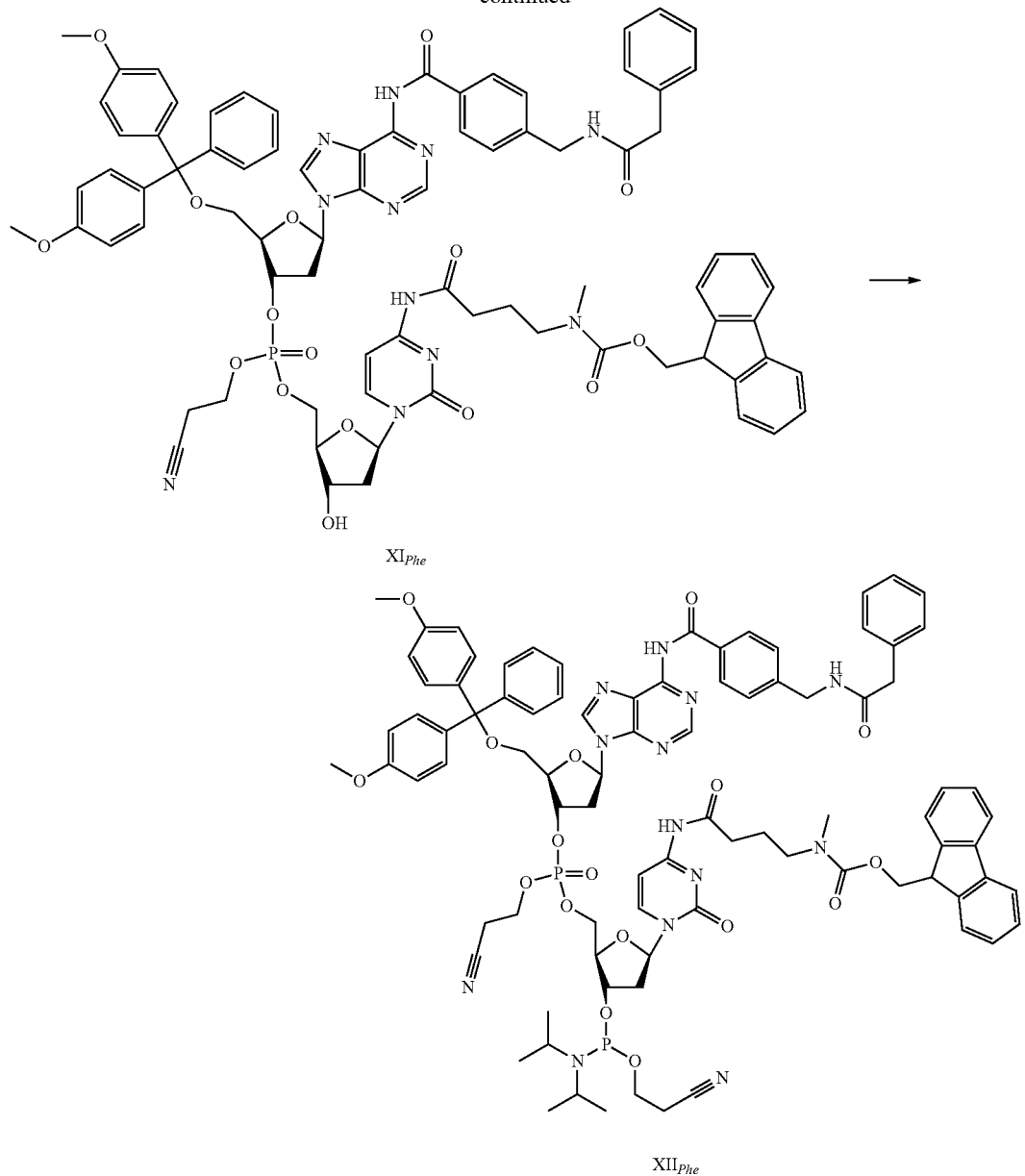

XI$_{Phe}$

XII$_{Phe}$

<Synthesis of VIII$_{Phe}$>

8.06 g (8.87 mmol) of VI was dissolved in 45 mL of dehydrated dichloromethane and 1.59 mL (10.6 mmol) of diazabicycloundecene was added to the solution while being cooled with ice. The solution was then agitated at room temperature for 3 hours to obtain reaction mixture A.

1.72 mL (12.4 mmol) of triethylamine was added to 32 mL of a dehydrated dichloromethane solution of 1.38 g (11.7 mmol) of N-hydroxysuccinic acid imide. Then, 1.41 mL (10.6 mmol) of phenylacetylchloride was also added to the solution while being cooled with ice and the solution was agitated at room temperature for 30 minutes. This solution was then added to the reaction mixture A. The reaction mixture was then agitated at room temperature for 4 hours. Subsequently, 5 mL of methanol was added to the solution, which was then agitated for 30 minutes. The reaction solution was diluted by dichloromethane and washed with water. The dichloromethane solution was concentrated under reduced pressure and the residue was purified by medium pressure chromatography (dichloromethane-ethanol 49:1→9:1). In this way, target product VIII$_{Phe}$ was obtained in an amount of 6.79 g (86%).

<Synthesis of IX$_{Phe}$>

4.83 g (6 mmol) of VIII$_{Phe}$ was dissolved in dehydrated acetonitrile and an operation of concentrating the solution under reduced pressure was repeated three times. The residue was dissolved in 48 mL of dehydrated dichloromethane and 37 mg (0.30 mmol) of dimethylaminopyridine and 1.36 mL (7.8 mmol) of diisopropylethylamine were added to the solution while being cooled with ice. Then, 12 mL of methylene chloride solution of 1.61 mL (7.2 mmol) of 2-cyanoethyldiisopropylchlorophosphoroamidite was added over more than 15 minutes. The mixture solution was agitated at 0° C. for 2 hours. Subsequently, 6 mL of methanol was added and the solution was agitated for 30 minutes. Then, the solution was concentrated under reduced pressure, diluted by dichloromethane and washed with water. The dichloromethane solution was concentrated under reduced pressure. The residue was dissolved in 60 mL of ethyl acetate and added dropwise to 600 mL of hexane at −30° C. The insoluble was removed by filtration. The filtered product was washed with cold hexane and the solvent was removed from the product under reduced pressure. In this way, target product $IX_{Phe}$ was obtained in an amount of 5.51 g (quant).

<Synthesis of $X_{Phe}$>

4.90 g (4.87 mmol) of $IX_{Phe}$ was dissolved in dehydrated acetonitrile and an operation of concentrating the solution under reduced pressure was repeated three times. The residue was dissolved in 25 mL of dehydrated acetonitrile to obtain solution A. 3.14 g (4.87 mmol) of IVc was dissolved into dehydrated acetonitrile and an operation of concentrating the solution under pressure was repeated three times. The residue was dissolved into 25 mL of dehydrated acetonitrile and added to the solution A. 1.71 g (24.3 mmol) of tetrazole was added to the reaction mixture and the mixture was agitated at room temperature for 1 hour. Subsequently, 2.5 mL of methanol was added to the mixture solution, which was then agitated for 30 minutes, diluted by dichloromethane and washed with water. The dichloromethane solution was concentrated under reduced pressure. The residue was dissolved into 102 mL of tetrahydrofuran, 30 mL of pyridine and 15 mL of water and 4.33 g (17.0 mmol) of iodine was added thereto. The mixture solution was then agitated at room temperature for 30 minutes. 440 mL of dichloromethane was added to the reaction mixture and then 10.7 g (85.2 mmol) of sodium sulfite was added thereto. The mixture was agitated at room temperature for 15 minutes. Then, about 30 g of sodium sulfate was added to the reaction mixture, which was then agitated well. Subsequently, the insoluble was removed by filtration and the filtered solution was concentrated under reduced pressure. The obtained residue was purified by medium pressure chromatography (dichloromethane-ethanol 49:1→17:3). In this way, target product $X_{Phe}$ was obtained in an amount of 5.10 g (67%).

<Synthesis of $XI_{Phe}$>

4.85 g (3.10 mmol) of $X_{Phe}$ was dissolved into 31 mL of pyridine and 31 mL of a diluted solution (pyridine:acetic acid=3:2) of 1.50 mL (26.7 mmol) of hydrazine monohydrate was added thereto on ice and the mixture solution was agitated at room temperature for 20 minutes. 30 mL of acetone was added to the solution while being cooled with ice and the solution was agitated at 0° C. for 10 minutes, diluted with dichloromethane and washed with water. The dichloromethane solution was concentrated under reduced pressure. The obtained residue was purified by medium pressure chromatography (dichloromethane-ethanol 19:1→4:1). In this way, target product $XI_{Phe}$ was obtained in an amount of 4.05 g (89%).

<Synthesis of $XII_{Phe}$>

1.00 g (0.68 mmol) of $XI_{Phe}$ was dissolved in dehydrated acetonitrile and an operation of concentrating the solution under reduced pressure was repeated three times. The residue was dissolved in 7.0 mL of dehydrated dichloromethane and 5.6 mg (0.034 mmol) of dimethylaminopyridine and 154 μL (0.88 mmol) of diisopropylethylamine were added to the solution while being cooled with ice. Then, 182 μL (0.82 mmol) of 2-cyanoethyldiisopropylchlorophosphoroamidite was added. The mixture solution was agitated at 0° C. for 3 hours. Subsequently, 0.7 mL of methanol was added and the solution was agitated for 30 minutes. The reaction solution was diluted with ethyl acetate and washed with water. Then, the ethyl acetate solution was concentrated under reduced pressure. The residue was dissolved in 10 mL of ethyl acetate:dichloromethane=4:1 and added dropwise in 68 mL of hexane at −30° C. The insoluble was removed by filtration. The filtered product was washed with cold hexane and the solvent was removed from the product under reduced pressure. In this way, target product $XII_{Phe}$ was obtained in an amount of 890 mg (78%).

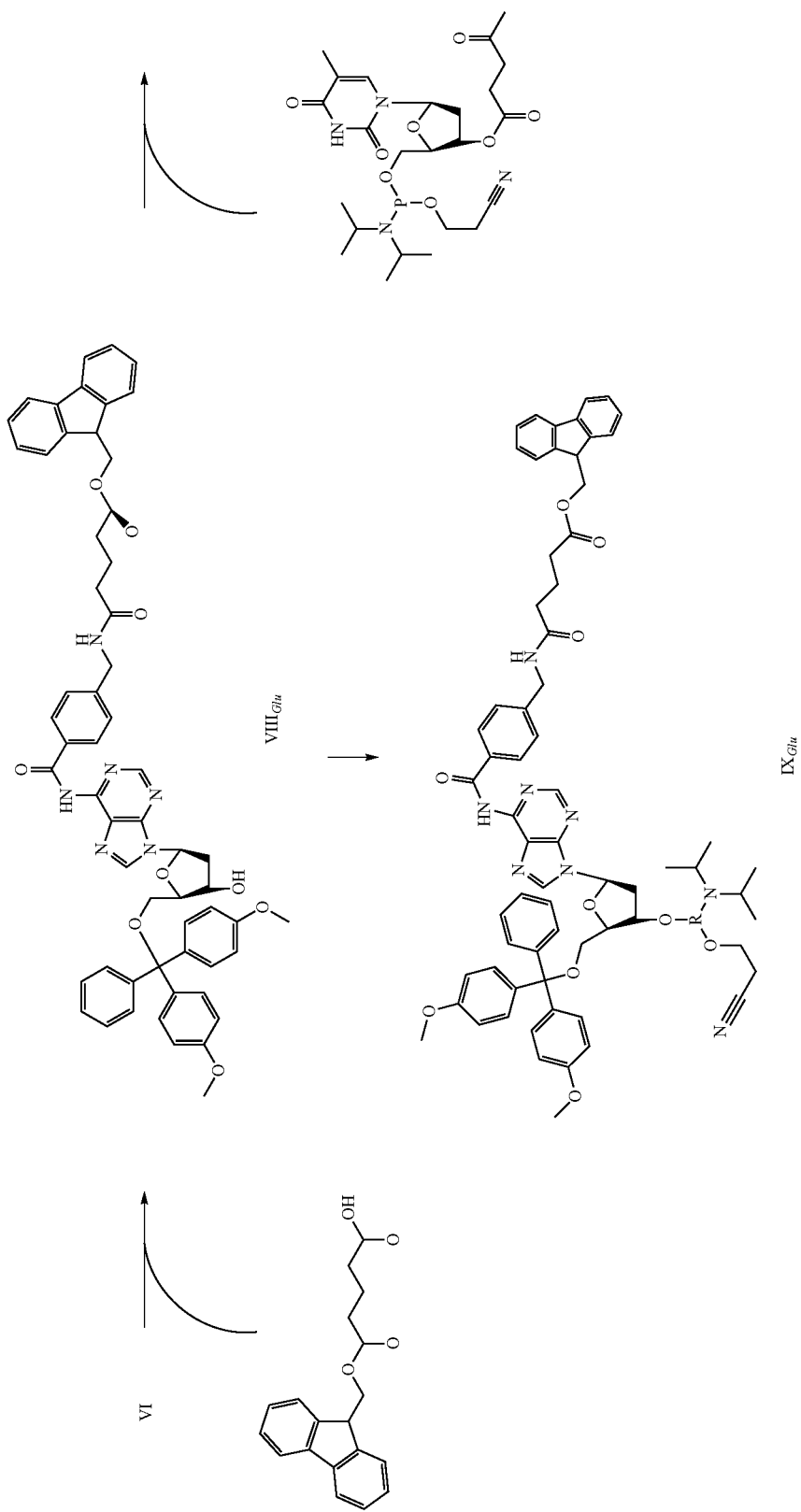

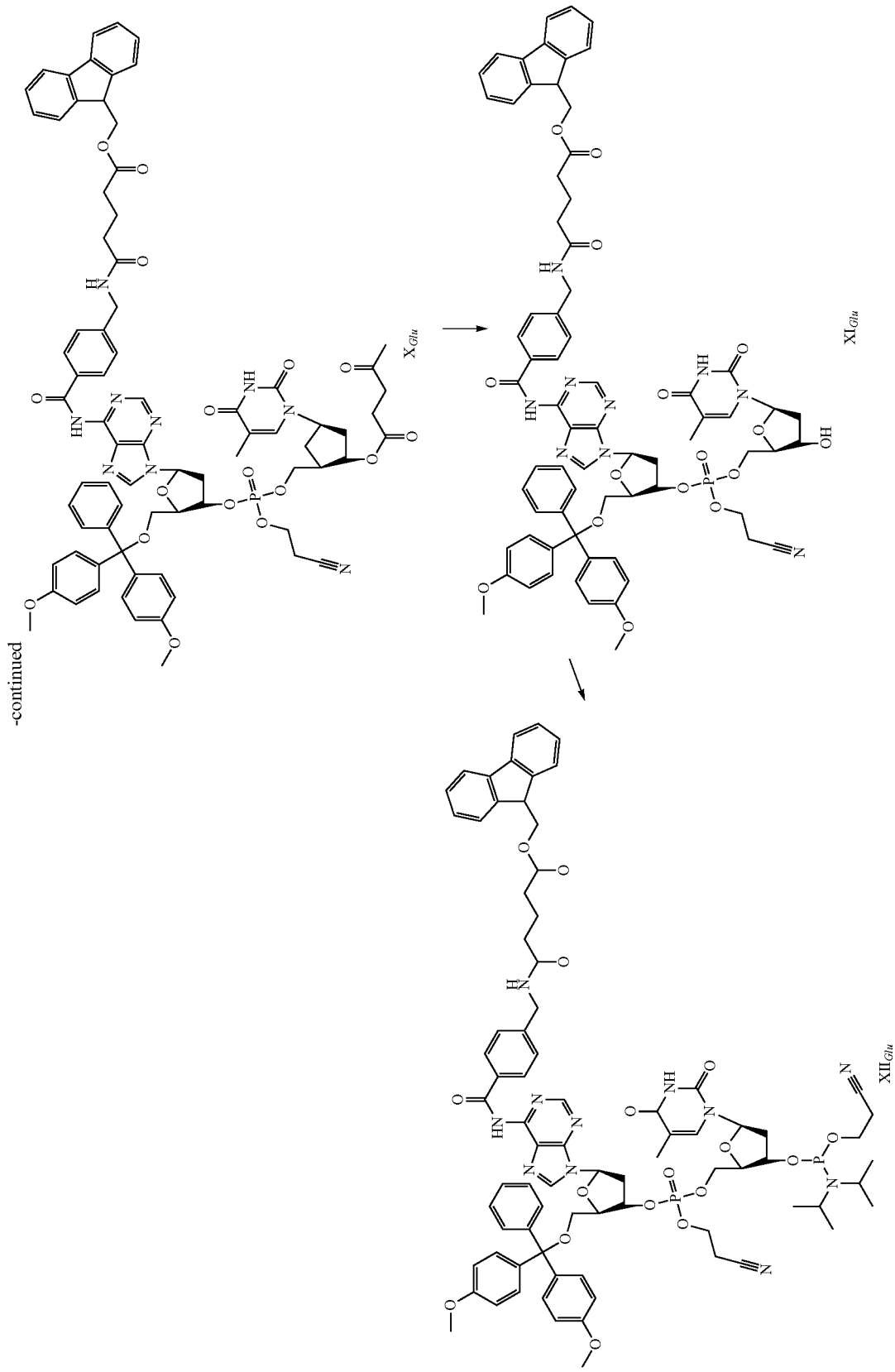

<Synthesis of VIII$_{Glu}$>

2.49 g (2.74 mmol) of VI was dissolved in 20 mL of dehydrated dichloromethane and 0.41 mL (2.74 mmol) of diazabicycloundecene was added to the solution while being cooled with ice. The solution was then agitated at room temperature for 3 hours. Then, 10 mL of diluted dichloromethane solution of 245 μL of trifluoroacetic acid and 230 μL of triethylamine was added to the reaction mixture to obtain reaction mixture A.

712 mg (3.45 mmol) of dicyclohexylcarbodiimide was added to 10 mL of a dehydrated dichloromethane solution of 1.02 g (3.29 mmol) of monofluorenyl methylglutarate and 417 mg (3.62 mmol) of N-hydroxysuccinic acid imide while being cooled with ice and the solution was agitated at room temperature for 3 hours. The insoluble was removed by filtration and the filtered solution was added to the reaction mixture A. The reaction mixture was then agitated at room temperature for 2 hours. Subsequently, 5 mL of methanol was added to the solution, which was then agitated for 30 minutes. The reaction solution was diluted by dichloromethane and washed with water. The dichloromethane solution was concentrated under reduced pressure and the residue was purified by medium pressure chromatography (dichloromethane-ethanol 49:1→9:1). In this way, target product VIII$_{Glu}$ was obtained in an amount of 1.86 g (69%).

<Synthesis of IX$_{Glu}$>

490 mg (0.5 mmol) of VIII$_{Glu}$ was dissolved in dehydrated acetonitrile and an operation of concentrating the solution under reduced pressure was repeated three times. The residue was dissolved in 10 mL of dehydrated dichloromethane and 3.1 mg (25 μmol) of dimethylaminopyridine and 128 μL (0.75 mmol) of diisopropylethylamine were added to the solution while being cooled with ice. Then, 134 μL (0.6 mmol) of 2-cyanoethyldiisopropylchlorophosphoroamidite was added. The mixture solution was agitated at room temperature for 2 hours. Subsequently, 2 mL of methanol was added and the solution was agitated for 30 minutes. The solution was concentrated under reduced pressure, diluted by dichloromethane and washed with water. The dichloromethane solution was concentrated under reduced pressure. The residue was dissolved in 4 mL of toluene and added dropwise in 50 mL of hexane at −30° C. The insoluble was removed by filtration. The filtered product was washed with cold hexane and the solvent was removed from the product under reduced pressure. In this way, target product IX$_{Glu}$ was obtained in an amount of 548 mg (93%).

<Synthesis of X$_{Glu}$>

2.91 g (2.97 mmol) of VIII$_{Glu}$ was dissolved in dehydrated acetonitrile and an operation of concentrating the solution under reduced pressure was repeated three times. The residue was dissolved in 10 mL of dehydrated dichloromethane to obtain solution A. 1.93 g (3.56 mmol) of 5'-(2-cyanoethyldiisopropylphosphoroamidyl-3'-levuloylthymidine was dissolved into dehydrated acetonitrile and an operation of concentrating the solution under pressure was repeated three times. The residue was dissolved into 15 mL of dehydrated dichloromethane and added to the solution A. 1.04 g (14.9 mmol) of tetrazole was added to the reaction mixture and the mixture was agitated at room temperature for 1 hour. Subsequently, 1.0 mL of methanol was added to the mixture solution, which was then agitated for 30 minutes, diluted by dichloromethane and washed with water. The dichloromethane solution was concentrated under reduced pressure. The residue was dissolved into 56 mL of tetrahydrofuran, 16 mL of pyridine and 8 mL of water and 2.64 g (10.4 mmol) of iodine was added thereto. The mixture solution was then agitated at room temperature for 30 minutes. 250 mL of dichloromethane was added to the reaction mixture and then 6.54 g of sodium sulfite was added thereto. The mixture was agitated at room temperature for 15 minutes. Then, about 15 g of sodium sulfate was added to the reaction mixture, which was then agitated well. Subsequently, the insoluble was removed by filtration and the filtered solution was concentrated under reduced pressure. The obtained residue was purified by medium pressure chromatography (dichloromethane-ethanol 97:3→9:1). In this way, target product X$_{Glu}$ was obtained in an amount of 3.67 g (86%).

<Synthesis of XI$_{Glu}$>

3.67 g (2.56 mmol) of X$_{Glu}$ was dissolved into 20 mL of pyridine and 30 mL of a diluted solution (pyridine:acetic acid=3:2) of 1.2 mL of hydrazine monohydrate was added thereto on ice and the mixture solution was agitated at room temperature for 10 minutes. 20 mL of acetone was added to the solution while being cooled with ice and the solution was agitated at 0° C. for 10 minutes, diluted with dichloromethane and washed with water. The dichloromethane solution was concentrated under reduced pressure. The obtained residue was purified by medium pressure chromatography (dichloromethane-ethanol 19:1→4:1). In this way, target product XI$_{Glu}$ was obtained in an amount of 2.81 g (82%).

<Synthesis of XII$_{Glu}$>

600 mg (0.45 mmol) of XI$_{Glu}$ was dissolved in dehydrated acetonitrile and an operation of concentrating the solution under reduced pressure was repeated three times. The residue was dissolved in 10 mL of dehydrated dichloromethane and 2.7 mg (0.023 mmol) of dimethylaminopyridine and 115 μL (0.67 mmol) of diisopropylethylamine were added to the solution while being cooled with ice. Then, 120 μL (0.54 mmol) of 2-cyanoethyldiisopropylchlorophosphoroamidite was added. The mixture solution was agitated at room temperature for 3 hours. Subsequently, 0.9 mL of methanol was added and the solution was agitated for 30 minutes. The reaction solution was diluted with dichloromethane and washed with water. Then, the dichloromethane solution was concentrated under reduced pressure. The residue was dissolved in 5.5 mL of dichloromethane and added dropwise in 50 mL of hexane at −30° C. The insoluble was removed by filtration. The filtered product was washed with cold hexane and the solvent was removed from the product under reduced pressure. In this way, target product XII$_{Glu}$ was obtained in an amount of 655 mg (95%).

VII →
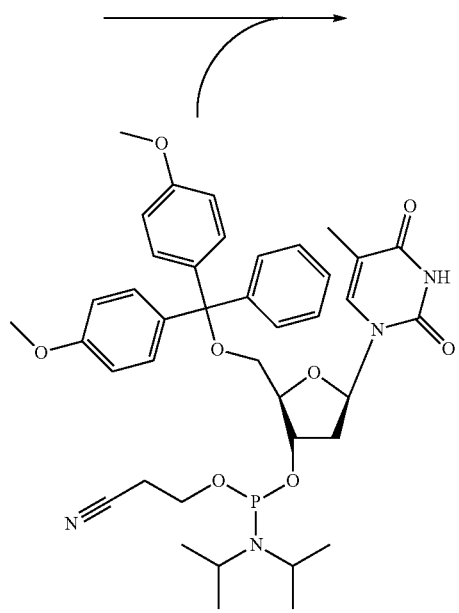
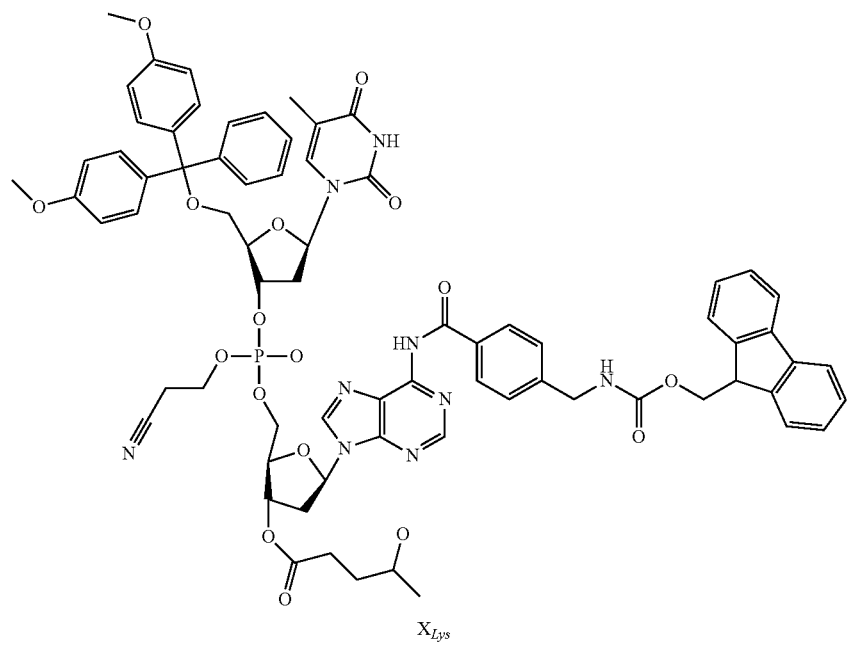

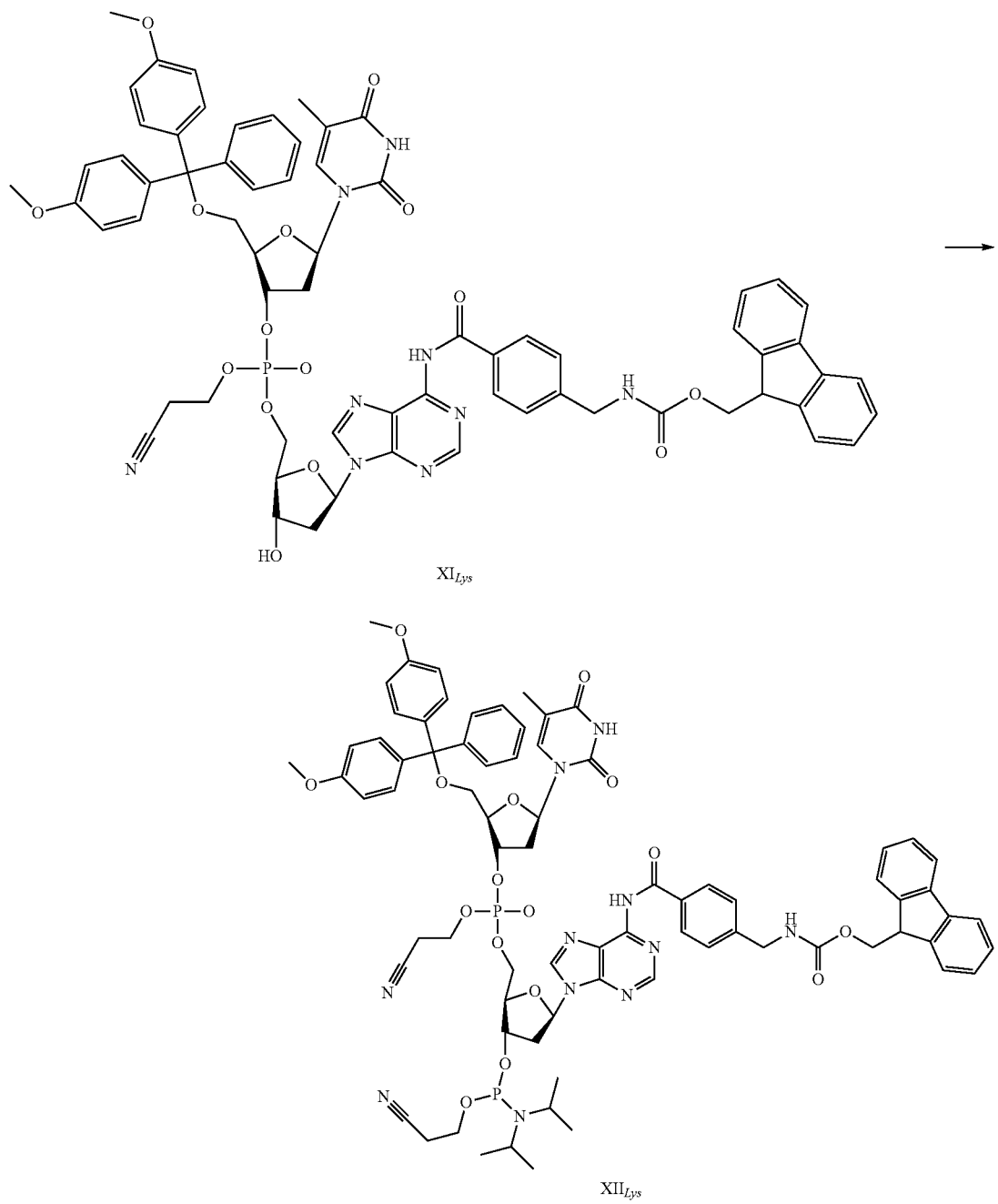

<Synthesis of X$_{Lys}$>

1.00 g (1.42 mmol) of VII was dissolved in dehydrated acetonitrile and an operation of concentrating the solution under reduced pressure was repeated three times. The residue was dissolved in 15 mL of dehydrated dichloromethane, to which 1.25 g (1.68 mmol) of 5'-(2-cyanoethyldiisopropylphosphoroamidylkhymidine was added. 497 mg (7.10 mmol) of tetrazole was added to the reaction mixture and the mixture was agitated at room temperature for 1 hour. Subsequently, 0.5 mL of methanol was added to the mixture solution, which was then agitated for 30 minutes, diluted by dichloromethane and washed with water. The dichloromethane solution was concentrated under reduced pressure. The residue was dissolved into 42 mL of tetrahydrofuran, 12 mL of pyridine and 6 mL of water and 1.26 g (4.97 mmol) of iodine was added thereto. The mixture solution was then agitated at room temperature for 30 minutes. Then, 120 mL of dichloromethane was added to the reaction mixture and 3.12 g of sodium sulfite was also added to the reaction mixture, which was then agitated at room temperature for 15 minutes. About 11 g of sodium sulfate was added to the reaction mixture, which was then agitated well. Subsequently, the insoluble was removed by filtration and the filtered solution was concentrated under reduced pressure. The obtained residue was purified by medium pressure chromatography (dichloromethane-ethanol 97:3→9:1). In this way, target product $X_{Lys}$ was obtained in an amount of 1.73 g (89%).

<Synthesis of $XI_{Lys}$>

1.72 g (1.26 mmol) of $X_{Lys}$ was dissolved into 10 mL of pyridine and 15 mL of a diluted solution (pyridine:acetic acid=3:2) of 580 μL of hydrazine monohydrate was added thereto on ice and the mixture solution was agitated at room temperature for 10 minutes. 10 mL of acetone was added to the solution while being cooled with ice and the solution was agitated at 0° C. for 10 minutes, diluted with dichloromethane and washed with water. The dichloromethane solution was concentrated under reduced pressure. The obtained residue was purified by medium pressure chromatography (dichloromethane-ethanol 19:1→9:3). In this way, target product $XI_{Lys}$ was obtained in an amount of 1.33 g (83%).

<Synthesis of $XII_{Lys}$>

1.32 g (1.04 mmol) of $XI_{Lys}$ was dissolved in dehydrated acetonitrile and an operation of concentrating the solution under reduced pressure was repeated three times. The residue was dissolved in 20 mL of dehydrated dichloromethane and 6.4 mg (0.052 mmol) of dimethylaminopyridine and 115 μL (0.67 mmol) of diisopropylethylamine were added to the solution while being cooled with ice. Then, 270 μL (1.57 mmol) of 2-cyanoethyldiisopropylchlorophosphoroamidite was added. The mixture solution was agitated at room temperature for 4 hours. Subsequently, 2.0 mL of methanol was added and the solution was agitated for 30 minutes. The reaction solution was diluted with dichloromethane and washed with water. Then, the dichloromethane solution was concentrated under reduced pressure. The residue was dissolved in 8.0 mL of ethyl acetate and added dropwise in 104 mL of hexane at −30° C. The insoluble was removed by filtration. The filtered product was washed with cold hexane and the solvent was removed from the product under reduced pressure. In this way, target product $XII_{Lys}$ was obtained in an amount of 1.16 g (76%).

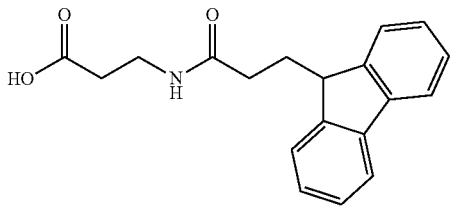

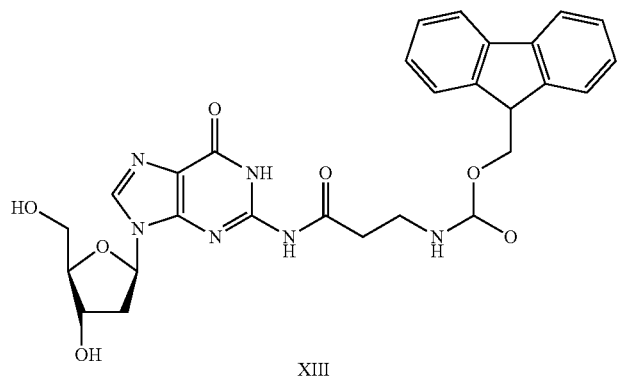

XIII

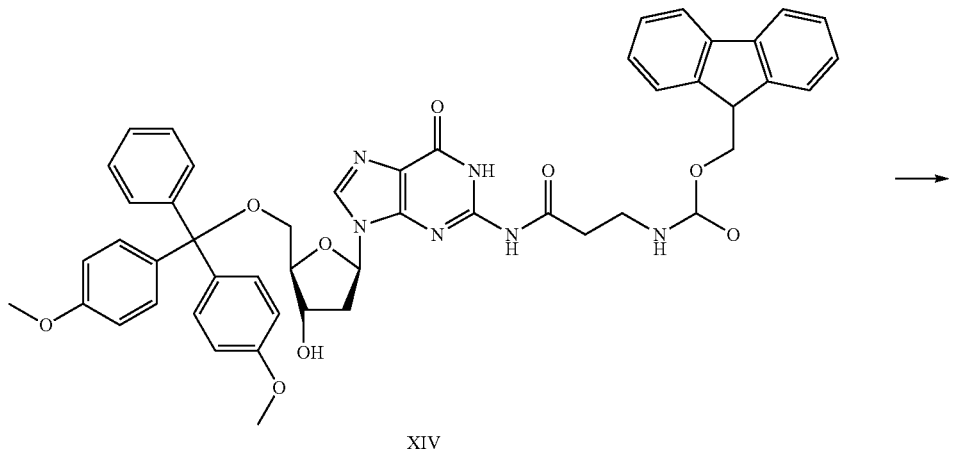

XIV

-continued
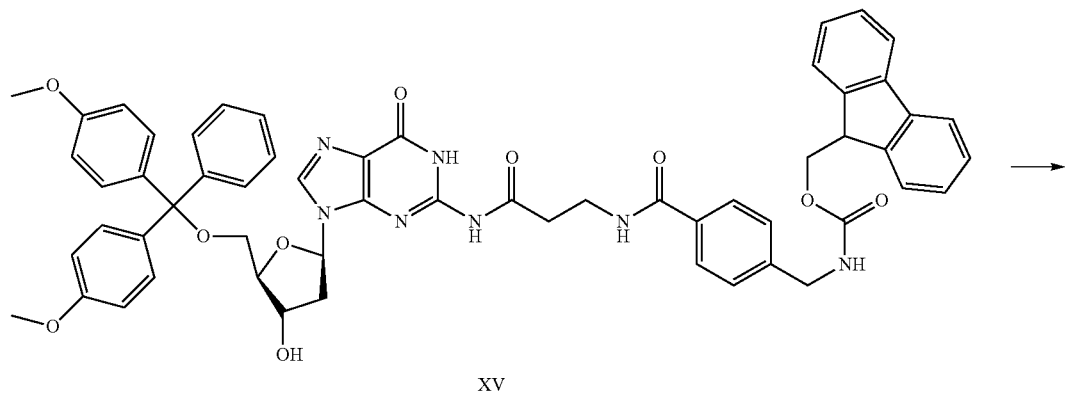
XV
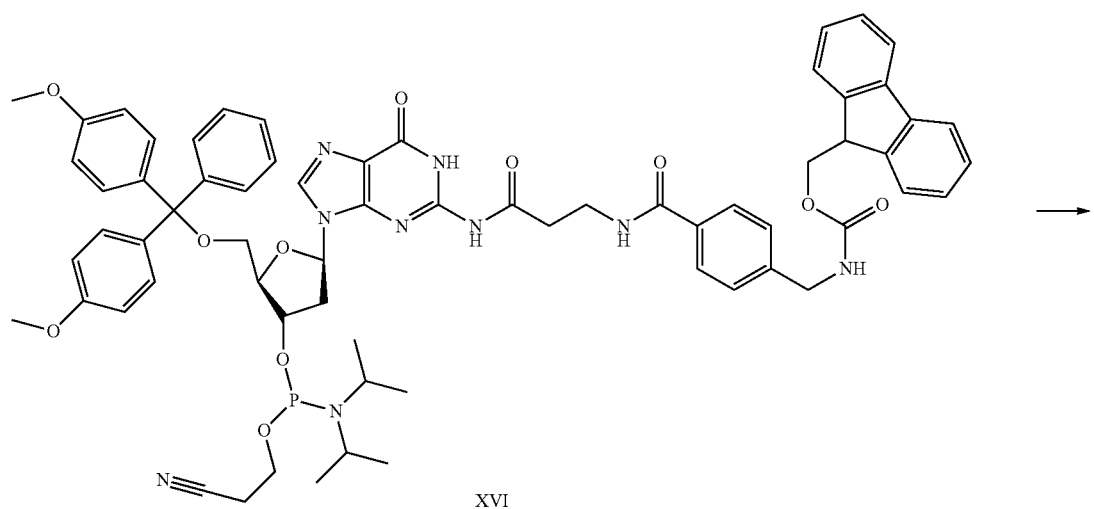
XVI
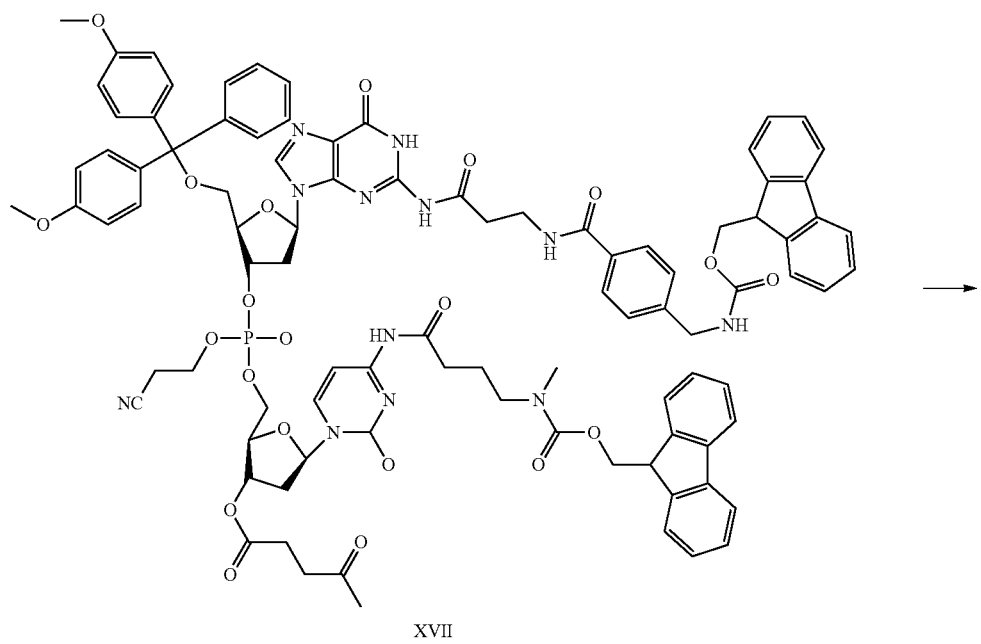
XVII

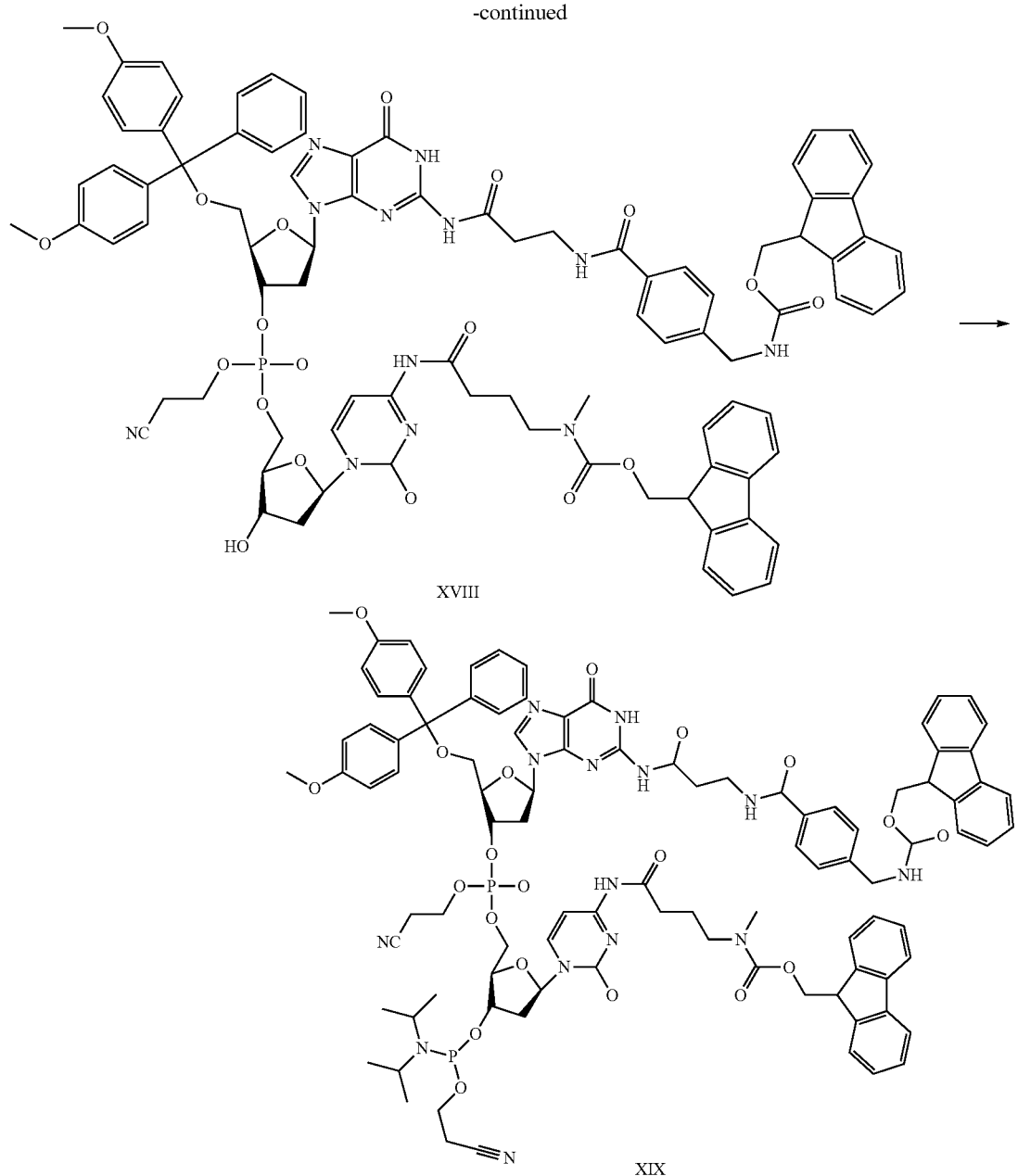

<Synthesis of XIII>

12.5 g (40 mmol) of FMOC-β-alanine was dissolved into 200 mL of dehydrated methylene chloride and 4.13 g (20 mmol) of N,N'-dicyclohexylcarbodiimide was added thereto at 0° C. The mixture solution was agitated at room temperature for 2 hours. After removing the insoluble by filtration, the solution was concentrated under reduced pressure to obtain residue A.

5.71 g (20 mmol) of deoxyguanosine monohydrate was suspended in dehydrated pyridine and an operation of concentrating it under reduced pressure was repeated three times. The residue was suspended in 100 mL of dehydrated pyridine and 8.45 mL (66 mmol) of trimethylchlorosilane was added thereto at 0° C. Then, the mixture solution was agitated at room temperature for 1 hour and subsequently cooled to 0° C. again before it was introduced to the residue A. The reaction mixture was agitated at room temperature for 2 hours. Then, 20 mL of water was added to the reaction mixture while the latter was being cooled with ice and the solution was agitated at room temperature overnight. The solution was diluted by methylene chloride and washed with water. The methylene chloride solution was concentrated under reduce pressure and the residue was purified by medium pressure chromatography (dichloromethane-ethanol 19:1→4:1) to obtain target product XIII in an amount of 8.90 g (79%).

<Synthesis of XIV>

8.41 g (15 mmol) of XIII was dissolved in dehydrated pyridine and an operation of concentrating the solution under reduced pressure was repeated three times. The residue was dissolved in 75 mL of dehydrated pyridine and 5.34 g (15.8 mmol) of 4,4'-dimethoxytritylchloride was added to the solution while being cooled with ice. The solution was agitated at room temperature for 4 hours. Subsequently, 15 mL of methanol was added and the solution was agitated for 30 minutes. Then, the solution was concentrated under reduced pressure, diluted by dichloromethane and washed with water. The dichloromethane solution was concentrated under reduced pressure and the residue was purified by medium pressure chromatography (dichloromethane-ethanol 19:1→9:1). In this way, target product XIV was obtained in an amount of 11.5 g (89%).

<Synthesis of XV>

7.13 g (8.27 mmol) of XIV was dissolved in 17 mL of dehydrated dichloromethane and 1.58 mL of triethylsilane and 1.24 mL (8.27 mmol) of diazabicycloundecene were added thereto. The mixture solution was agitated at room temperature for 3 hours. 5 mL of dehydrated dichloromethane dilute solution of containing 762 μL of trifluoroacetic acid and 401 μL of pyridine was added to the reaction mixture to obtain reaction mixture A.

3.35 g (9.92 mmol) of 4-(FMOC-aminomethyl)benzoic acid was suspended in 40 mL of dehydrated dichloromethane and 1.70 mL (18.8 mmol) of oxaryl chloride and 15 μL (0.19 mmol) of dimethylformamide were added thereto in an argon atmosphere and the mixture was agitated at room temperature overnight. The reaction solution was concentrated under reduced pressure. Dehydrated toluene was added to the residue and the mixture solution was concentrated under reduced pressure. The residue was dissolved in 50 mL of dehydrated dichloromethane and 1.61 g (11.9 mmol) of 1-hydroxybenzotriazole was added thereto. Subsequently, the mixture solution was cooled with ice and 1.20 mL of pyridine was added thereto. The mixture solution was then agitated at room temperature for 1 hour, diluted by dichloromethane and washed with water. The dichloromethane solution was then concentrated under reduced pressure and 12 mL of the dehydrated dichloromethane was added to the reaction mixture A. The mixture solution was then agitated at room temperature for 3 hours. Subsequently, 10 mL of methanol was added thereto and the mixture solution was agitated for 30 minutes. The reaction solution was diluted by dichloromethane and washed with water. The dichloromethane solution was concentrated under reduced pressure and the residue was purified by medium pressure chromatography (dichloromethane-ethanol 49:1→9:1). In this way, target product XV was obtained in an amount of 5.20 g (63%).

<Synthesis of XVI>

5.10 g (5.12 mmol) of XV was dissolved in a mixture solution of dehydrated acetonitrile and dehydrated dichloromethane and an operation of concentrating the solution under reduced pressure was repeated three times. The residue was dissolved in 40 mL of dehydrated dichloromethane and 31 mg (0.26 mmol) of dimethylaminopyridine, 1.3 mL (7.6 mmol) of diisopropylethylamine while being cooled with ice and then 1.3 mL (5.8 mmol) of 2-cyanoethyldiisopropylchlorophosphoroamidite were added to the solution. The mixture solution was agitated at room temperature for 2 hours. Subsequently, 15 mL of methanol was added and the solution was agitated for 30 minutes. Then, the solution was concentrated under reduced pressure, diluted by dichloromethane and washed with water. The dichloromethane solution was concentrated under reduced pressure. The residue was dissolved in 55 mL of ethyl acetate and added dropwise in 515 mL of hexane at −30° C. The insoluble was removed by filtration. The filtered product was washed with cold hexane and the solvent was removed from the product under reduced pressure. In this way, target product XVI was obtained in an amount of 5.78 g (94%).

<Synthesis of XVII>

2.13 g (1.78 mmol) of XVI was dissolved in dehydrated acetonitrile and an operation of concentrating the solution under reduced pressure was repeated three times. The residue was dissolved in 20 mL of dehydrated dichloromethane to obtain solution A. 1.15 g (1.78 mmol) of IVc was dissolved into dehydrated acetonitrile and dehydrated dichloromethane and an operation of concentrating the solution under pressure was repeated three times. The residue was added to the solution A, using 8 mL of dehydrated dichloromethane. 623 mg (8.9 mmol) of tetrazole was added to the reaction mixture and the mixture was agitated at room temperature for 2 hour. Subsequently, 1.0 mL of methanol was added to the mixture solution, which was then agitated for 30 minutes, diluted by dichloromethane and washed with water. The dichloromethane solution was concentrated under reduced pressure. The residue was dissolved into 28 mL of tetrahydrofuran, 8 mL of pyridine and 4 mL of water and 1.6 g (6.3 mmol) of iodine was added thereto. The reaction mixture solution was then agitated at room temperature for 30 minutes. 100 mL of dichloromethane was added to the reaction mixture and then 4.0 g of sodium sulfite was added thereto. The mixture was agitated at room temperature for 15 minutes. Then, about 10 g of sodium sulfate was added to the reaction mixture, which was then agitated well. Subsequently, the insoluble was removed by filtration and the filtered solution was concentrated under reduced pressure. The obtained residue was purified by medium pressure chromatography (dichloromethane-ethanol 19:1→9:1). In this way, target product XVII was obtained in an amount of 2.09 g (67%).

<Synthesis of XVIII>

1.92 g (1.10 mmol) of XVII was dissolved into 12 mL of pyridine and 14 mL of a diluted solution (pyridine:acetic acid=3:2) of 0.51 mL of hydrazine monohydrate was added thereto on ice and the mixture solution was agitated at room temperature for 10 minutes. 10 mL of acetone was added to the solution while being cooled with ice and the solution was agitated at 0° C. for 10 minutes, diluted by dichloromethane and washed with water. The dichloromethane solution was concentrated under reduced pressure. The residue was purified by medium pressure chromatography (dichloromethane-ethanol 93:7→17:3). In this way, target product XVIII was obtained in an amount of 1.54 g (85%).

<Synthesis of XIX>

830 mg (0.50 mmol) of XVIII was dissolved in dehydrated acetonitrile and an operation of concentrating the solution under reduced pressure was repeated three times. The residue was dissolved in 10 mL of dehydrated dichloromethane and 3.1 mg (0.025 mmol) of dimethylaminopyridine and 103 μL (0.60 mmol) of diisopropylethylamine were added to the solution while being cooled with ice. Then, 123 μL (0.55 mmol) of 2-cyanoethyldiisopropylchlorophosphoroamidite was added thereto. The mixture solution was agitated at room temperature for 3 hours. Subsequently, 1.0 mL of methanol was added and the solution was agitated for 30 minutes. Then, the reaction solution was diluted by dichloromethane and washed with water. The dichloromethane solution was concentrated under reduced pressure. The residue was dissolved in 5 mL of dichloromethane and added dropwise in 50 mL of hexane at −30° C. The insoluble was removed by filtration. The filtered product was washed with cold hexane and the solvent was removed from the product under reduced pressure. In this way, target product XIX was obtained in an amount of 882 mg (95%).

<Confirmation of Structure of Compound>

The structure of each of the above-described compounds was confirmed in a manner as describe below. FIGS. 1 through 41 show some of the obtained results. The results of the confirmation of the structure of each of the compounds I through III are same as those described in the specification of Japanese Patent Application No. 2007-000576.
[MALDI-TOF]

As for fat-soluble compounds, 8 μL of acetone solution containing Dithranol at a rate of 10 mg/ml and 2 μL of a sample dilute solution (approximately 20 pmol/L) were mixed and 1 μL of the mixture was developed on a massive target. A dithranol matrix was used as internal standard for calibration lines.

As for water-soluble oligonucleotides, a sample dilute solution was treated by a hydrogen ion type ion-exchange resin. Separately, 1 μL of a 1:1 mixture solution of diammonium hydrogen citrate (DAC) and 3-hydroxypicolinic acid (HPA) was developed in advance on a TOF-MS target Anchor Chip and 1 μL of a sample liquid is mixed with it. The mixture solution of the sample liquid was then slowly dried by air and observed. A specified peptide mixture sample for calibration lines was used as reference substance for calibration lines.
[$^1$H-NMR]

About 5 mg of each sample was dissolved in a heavy solvent and subjected to measurement. The peak of the heavy solvent was used as internal standard.
[$^{31}$P-NMR]

$PPh_3$ was used as external standard and −6.2 ppm was used as reference for observation. Measurements were conducted by BCM.

Example 2

Confirmation of Deprotection by DBU Treatment in Acetonitrile

A nucleic acid analogue was synthesized using a functional molecule synthesizing amidite and subsequently it was confirmed by way of the process shown below that the protection group (the group of the first stage) was forced to leave by conducting a DBU treatment in acetonitrile and a desired nucleic acid analogue (functional molecule) having a substituent was synthesized.

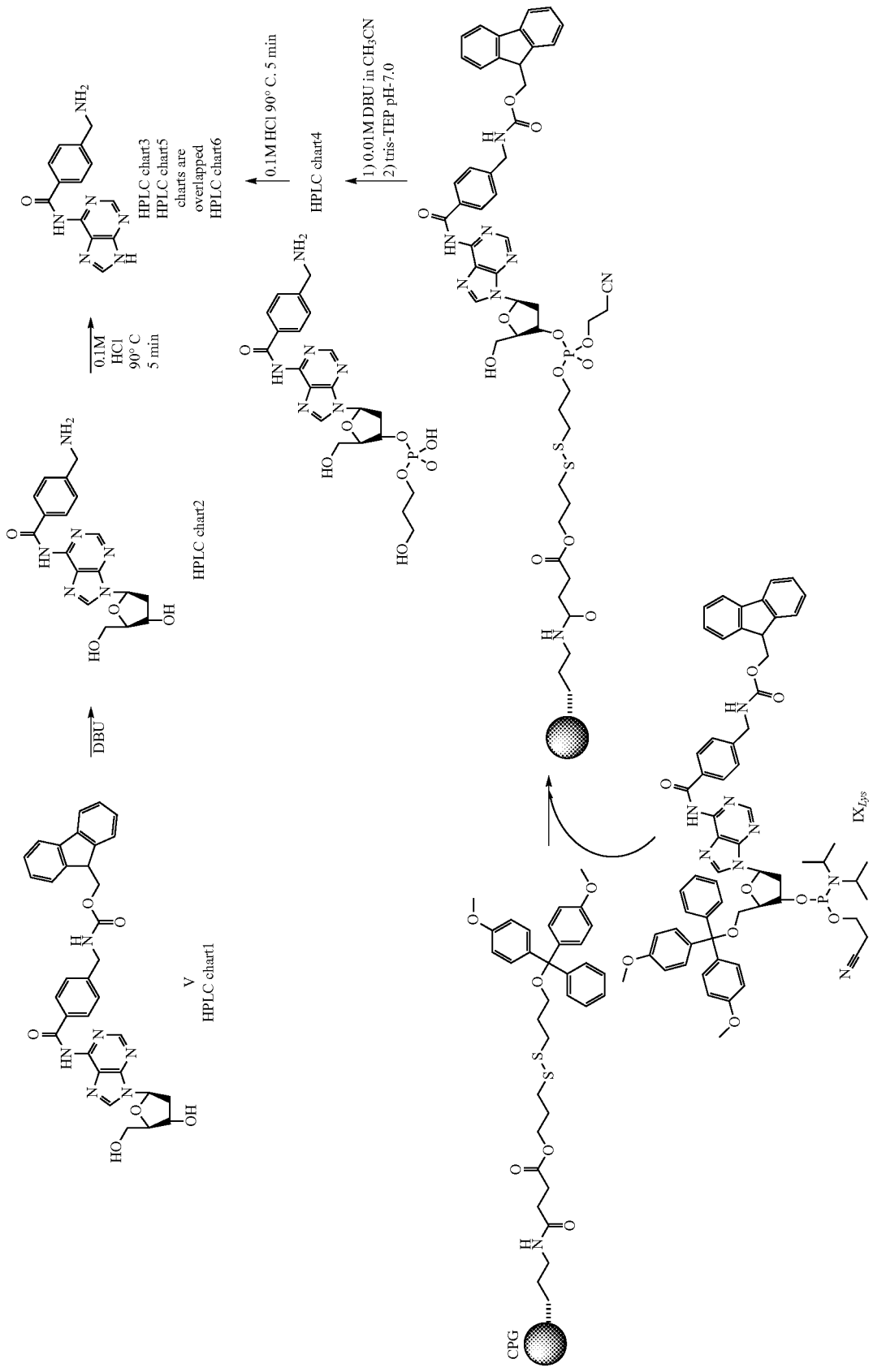

Figure 42:
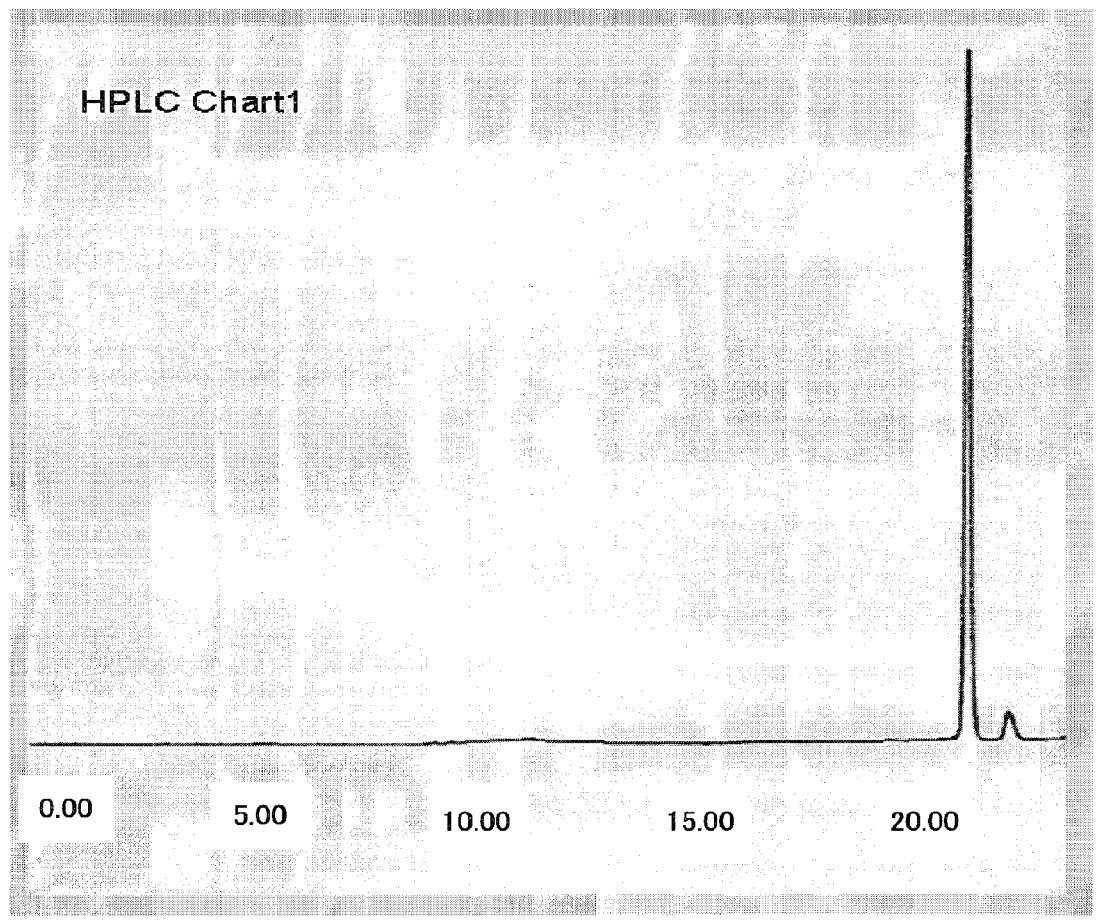
FIG. 42 is a HPLC Chart 1 of Example 2.
Figure 43:
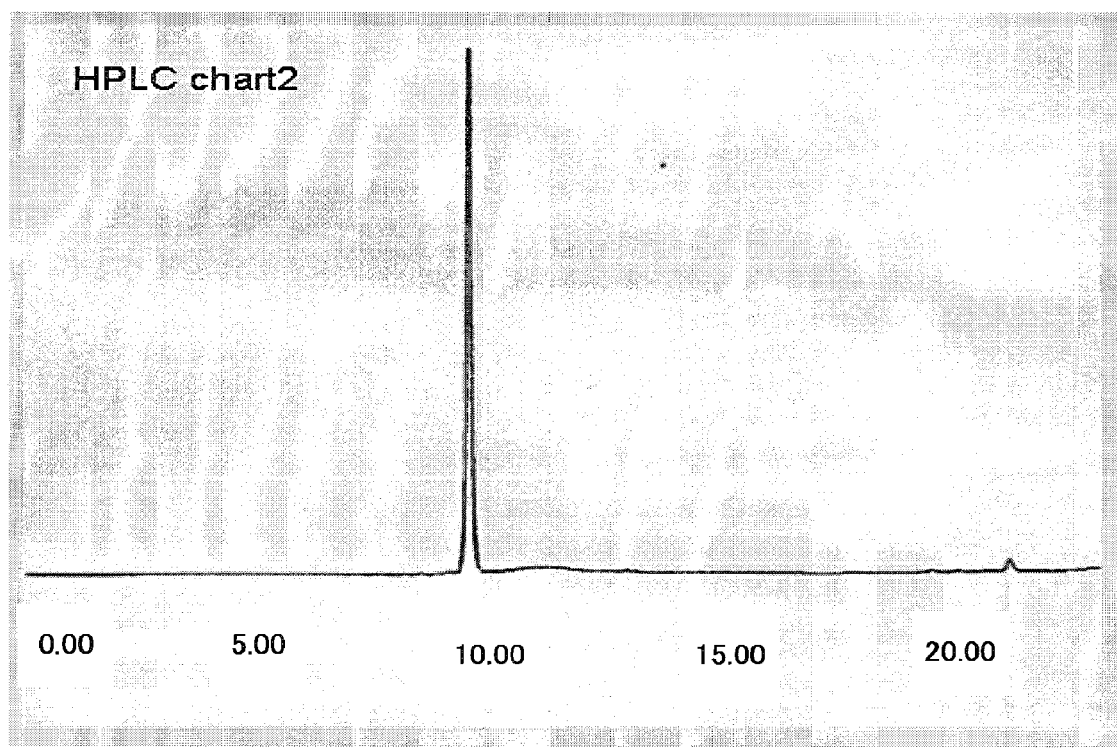
FIG. 43 is a HPLC Chart 2 of Example 2.
Figure 44:
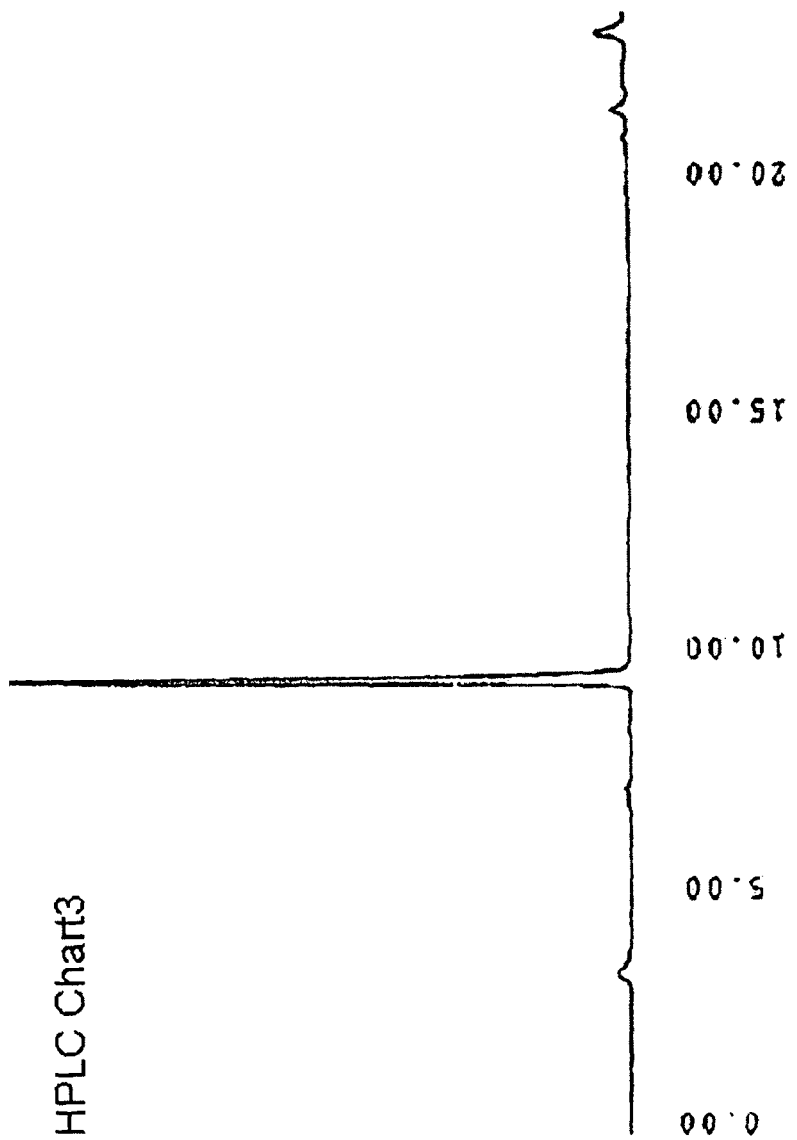
FIG. 44 is a HPLC Chart 3 of Example 2.

Firstly, 1.7 mM of the compound V obtained in Example 1 (HPLC Chart 1, FIG. 42) and 10 mM of a DBU (10% of DMF, 90% of acetonitrile) solution were put together and left to stand at room temperature for 15 minutes to obtain a reaction mixture (HPLC Chart2, FIG. 43). The main peak of HPLC Chart 2 was separated and left to stand in 0.1M HCl at 90° C. for 5 minutes to obtain a reaction mixture (HPLC Chart 3, FIG. 44).

Figure 45:
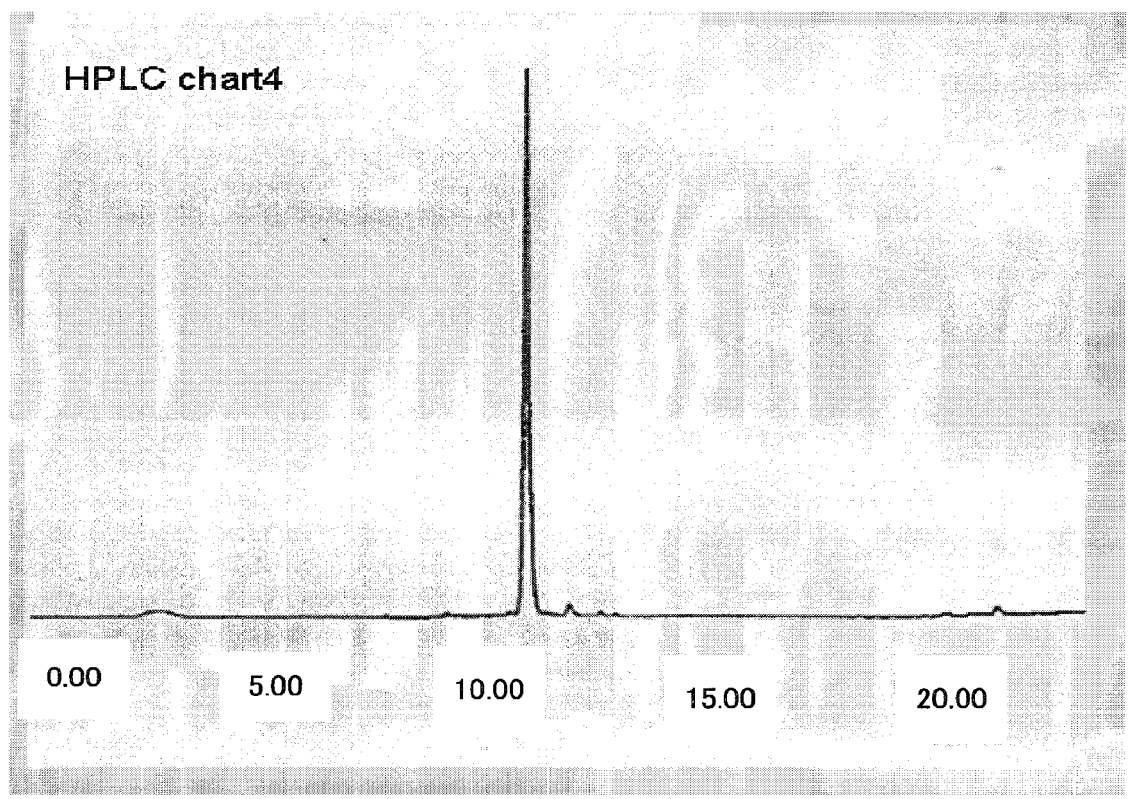
FIG. 45 is a HPLC Chart 4 of Example 2.
Figure 46:
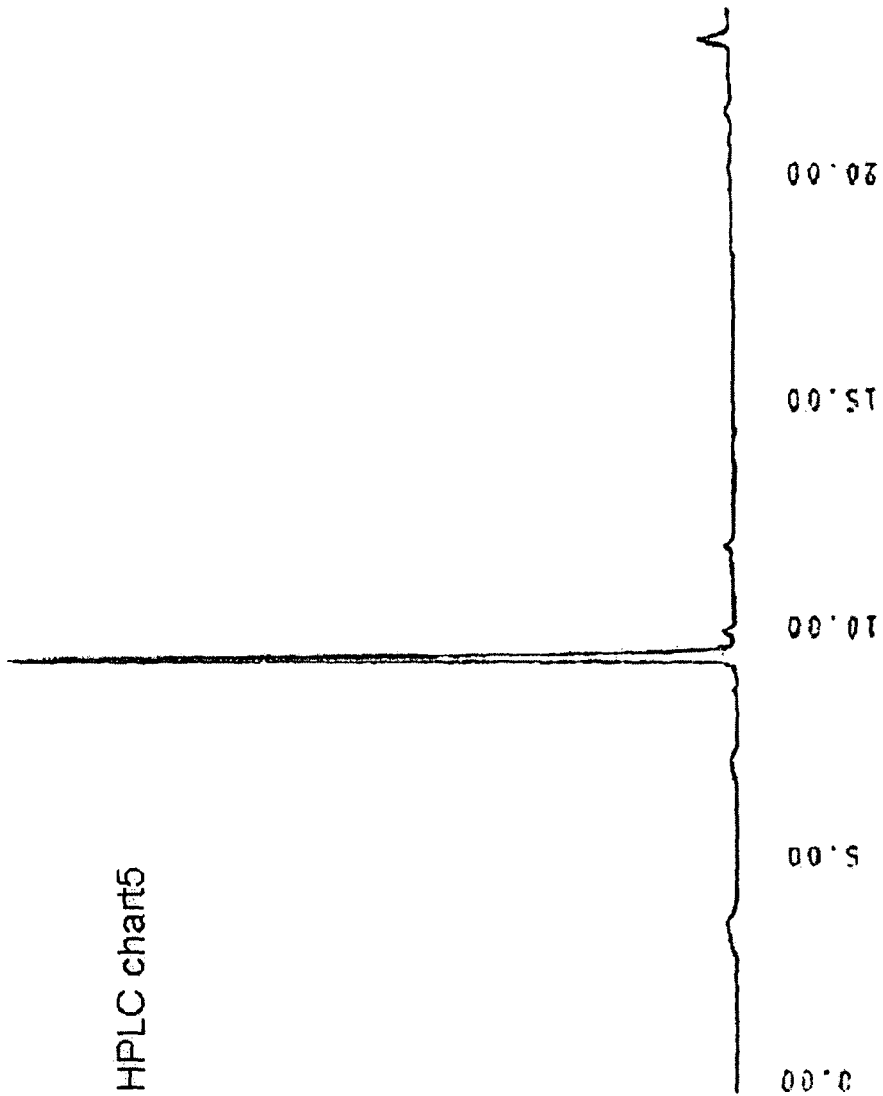
FIG. 46 is a HPLC Chart 5 of Example 2.

Thereafter, a residue was synthesized by way of an ordinary DNA synthesizing cycle, using $IX_{Lys}$ amidite obtained in Example 1 on commercially available C3SS-CPG, and 5 mL of 0.01M DBU acetonitrile solution was made to flow over an hour. Subsequently, it was washed consecutively with acetonitrile and water and then 0.25 mL of 0.1M tris(2-carboxyethyl)phosphine hydrochloride-tris(hydroxymethyl)aminoethane buffer solution with pH=7.0 (TCEP-Tris pH=7.0) was made to flow over an hour and collected (HPLC Chart4, FIG. 45). The solution (HPLC Chart4) was diluted to a concentration of 1/10 and left to stand under the condition of 0.1M HCl at 90° C. for 5 minutes to obtain a reaction mixture (HPLC Chart5, FIG. 46).

Figure 47:
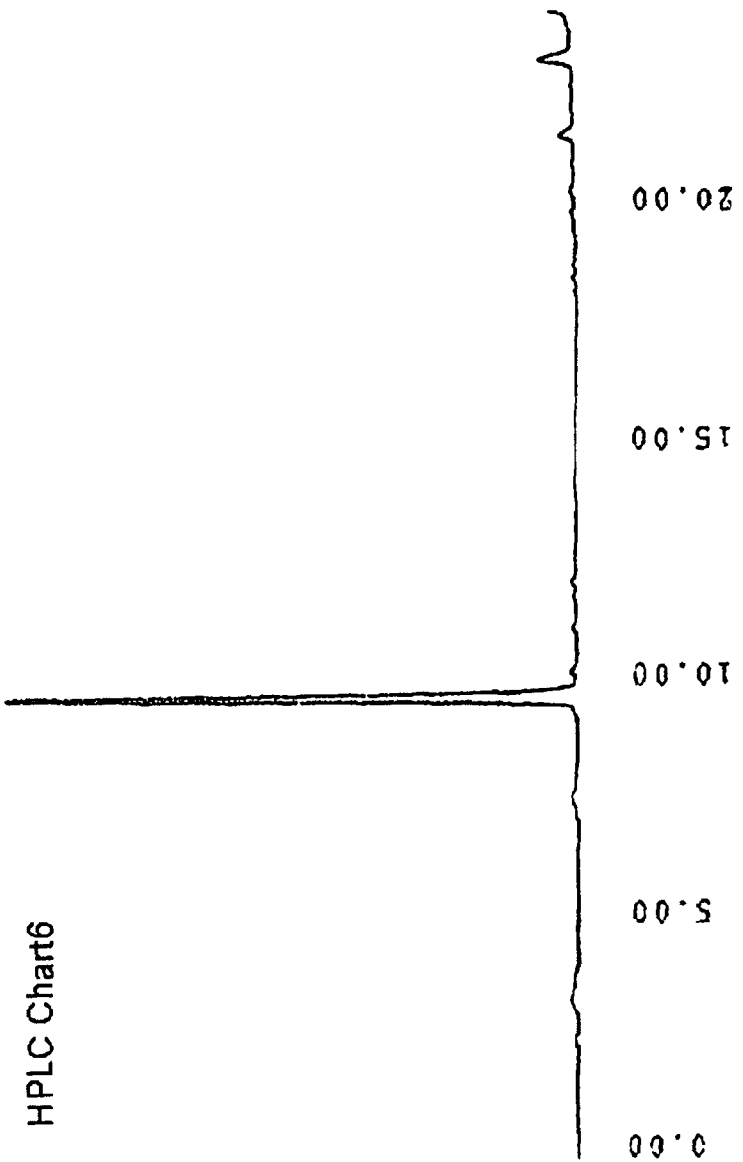
FIG. 47 is a HPLC Chart 6 of Example 2.

While the HPLC Chart obtained by the reaction mixture of HPLC Chart3 and the one obtained by the reaction mixture of HPLC Chart5 were similar to each other, the HPLC Chart of a mixture solution of HPLC Chart3 and HPLC Chart5 was checked (HPLC Chart6, FIG. 47) for the purpose of confirmation.

As a result, the reaction mixture of HPLC Chart3 and that of HPLC Chart5 were found to be identical. Therefore, it was confirmed that, after synthesizing a nucleic acid analogue by means of a functional molecule synthesizing amidite according to the present invention, the protection group (the group of the first stage) can be made to leave by means of a DBU treatment in acetonitrile and a desired nucleic acid analogue (functional molecule) having a substituent can be synthesized.

Example 3

Confirmation of Removal of Substituent by Ammonia Treatment

It was confirmed in a manner as described below that the substituent (the group of the second stage) of a functional molecule synthesized using the functional molecule synthesizing amidite according to the present invention can be removed by ammonia treatment and that the functional molecule can be readily amplified by PCR.

The sequence: GAAGGTGAAGGTCGGCTGAA88 V88V88V88VGCT88V88V88V88VACCATCATCACCAT CTT (80 mer, Sequence ID No. 1 (only A, C, G and T are shown in the Sequence Listing) was synthesized. An equivalent mixture amidite of IIIg, IIIc or the like was used for "V", while an equivalent mixture amidite of $XII_{Leu}$, $XII_{Phe}$, $XII_{Glu}$, $XII_{Lys}$, XIX or the like was used for "8".

The synthesized analogous DNA random mix was subjected to deprotection by feeding 0.01M diazabicycloundecene (DBU) in acetonitrile and cut out from the solid carrier using 250 μL of aqueous solution of 0.1 TCEP-tris pH-7.0, and an aqueous solution of 0.5M malein imide was added to the obtained SH terminal analogous DNA solution. The modified analogous DNA (functional molecule) was roughly purified by means of CTTCACCTTC (Sequence ID No. 2) oligomer modified resin and the DNA concentration was calculated approximately at λ=260.

Two volumes (v/v) of 28% ammonia water was added to the modified analogous DNA (functional molecule) obtained above and ammonia treatment was conducted by heating the resultant mixture at 55° C. for 8 hours, thereby removing substituents from the functional molecule. The obtained solution was concentrated under reduced pressure.

Figure 48:
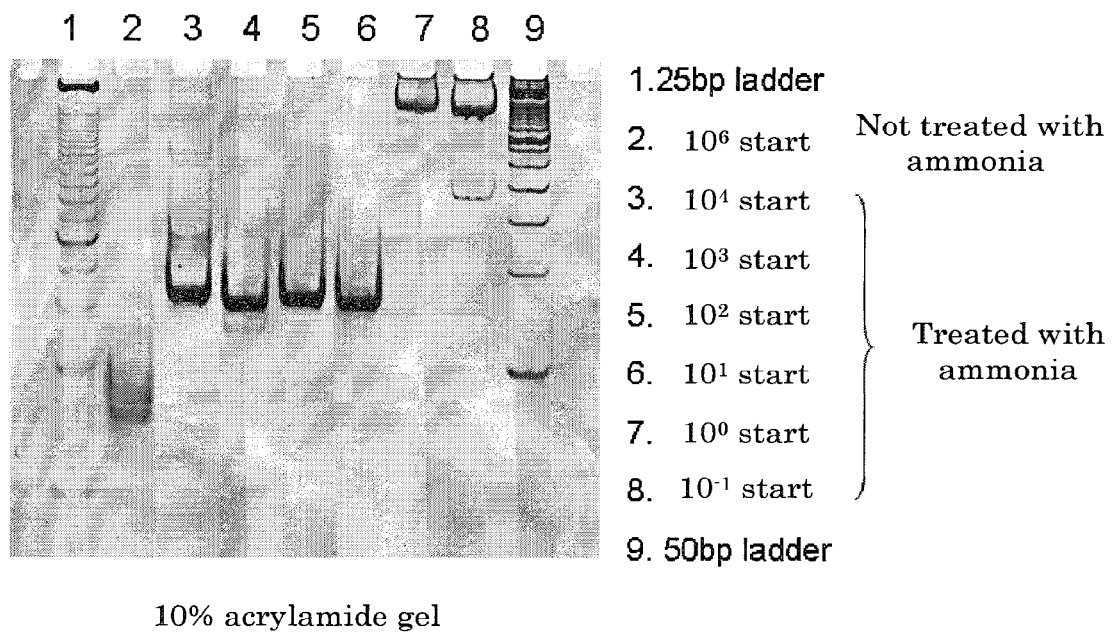
FIG. 48 is a schematic electrophoretic image, showing the PCR result of the modified DNA analogue samples (treated with and not treated with ammonia) of each group of Example 3.

A series of dilutions were prepared for each of the modified analogous DNA solutions (one after treated with ammonia, and the other not treated with ammonia) as shown in FIG. 48 and PCR amplification was performed (60 cycles).

The electrophoresis results shown in FIG. 48 show that bands around a normal 80 mer were seen only for the modified analogous DNA (functional molecule) treated with ammonia (Lanes 3 through 6). This proved that their substituents can be removed from a functional molecule synthesized using the functional molecule synthesizing amidite according to the present invention by way of ammonia treatment and therefore the functional molecule can be amplified with ease by PCR.

It was confirmed in a manner as described below that the dimer code of each amidite did not change in the process including the PCR of the functional molecule.

Figure 49:
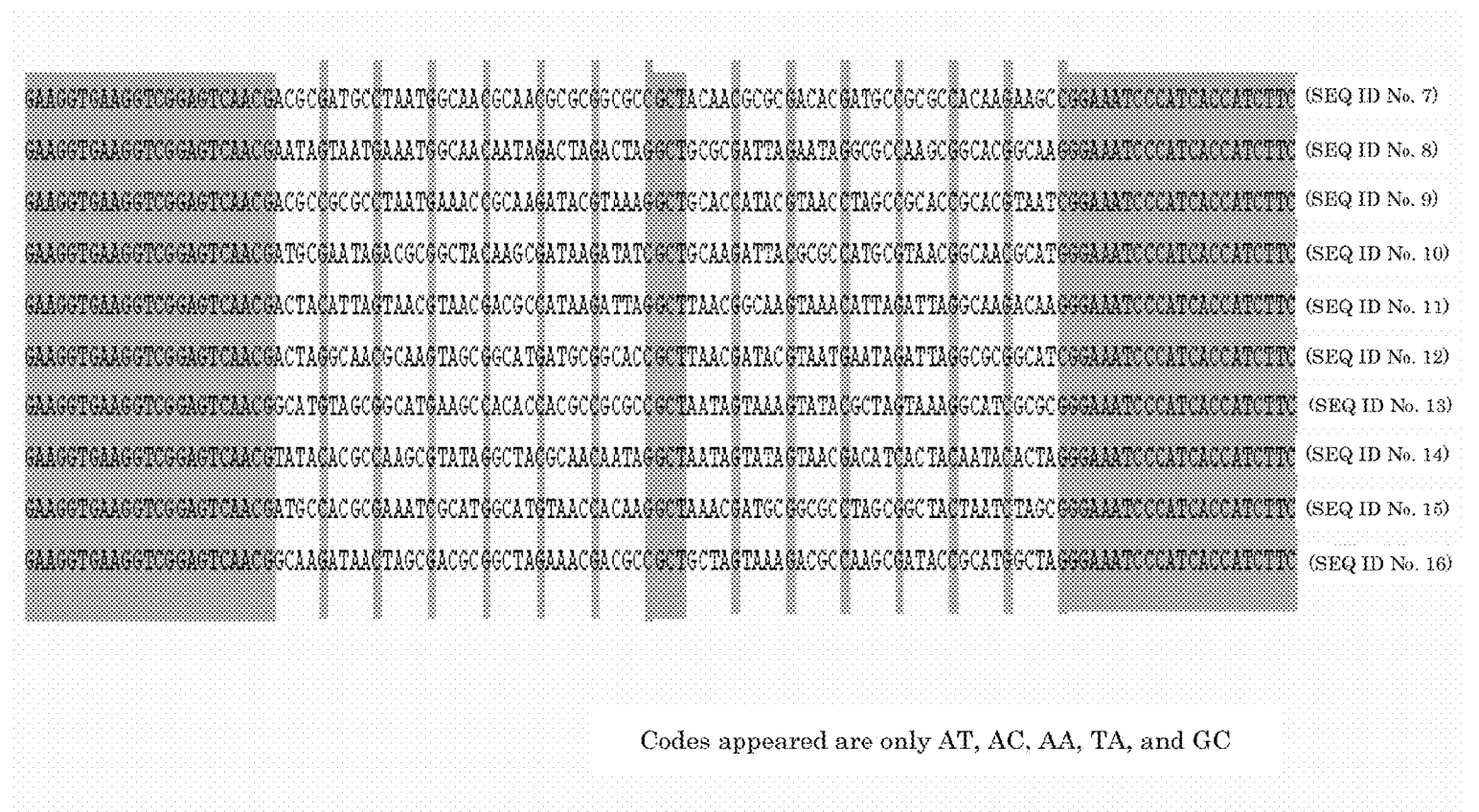

The sequence: GAAGGTGAAGGTCGGAGTCAACG 88V88V88V88V88V88V88VGCT88V88V88V88V88V 88V88VGGAAATCCCATCACCATCTTC, Sequence ID No. 3 (only A, C, G and T are shown in the Sequence Listing) was synthesized and the modified analogous DNA (functional molecule) was collected from the solid element. The product was roughly purified and treated with ammonia water. After PCR amplification, cloning and sequencing were conducted. FIG. 49 illustrates some of the obtained results. As seen from FIG. 49, only AA, AC, AT, TA and GC that correspond to the amidites appeared on the residue that corresponds to "8" where a mixture amidite of $XII_{Leu}$ (AA), $XII_{Phe}$ (AC), $XII_{Glu}$ (AT), $XII_{Lys}$ (TA) and XIX (GC) was used. On the basis of this fact, it was confirmed that the dimer code of each amidite was not changed by the cloning and sequencing process.

Thus, according to the present invention, the type of the substituent introduced in each dimer amidite is determined typically by referring to a dimer code correspondence table (showing the correspondence of the base sequences of dimer amidites and the types of substituent) and the functional molecule synthesized from the dimer amidite is coupled to a target substance. Then, after screening a functional molecule having affinity for a target substance, its substituents are removed and subjected to PCR amplification and sequencing (for determining the base sequence). In this way, the type of the substituent introduced to the functional molecule can be determined by referring to the dimer code correspondence table. Then, the functional molecule can be replicated.

Example 4

Target Substance Analysis Method

It was confirmed in a manner as described below that the functional molecule according to the present invention synthesized using the functional molecule synthesizing amidite according to the present invention can suitably be used for the analysis of target substance.

The dimer amides of five different types shown in Table 1 below (prepared in Example 1) were used to synthesize a modified analogous DNA random sequence shown below. The sites to be synthesized using the dimer amide are indicted by NpNp.

[Modified Analogous DNA Random Sequence]

ttatcaacaaaatactccaattgact (NpNpG/Cp)$_7$ gct (NpNpG/Cp)$_7$ ttcgaaagatcccaacgaaaagp (CH$_2$)$_3$SH (Sequence ID No. 4 (only a, c, g and t are shown in the Sequence Listing).

TABLE 1

|   |   | 3' |   |   |   |
|---|---|---|---|---|---|
|   |   | A | G | C | T |
| 5' | A | XIIILeu | — | XIIPhe | XIIGlu |
|   | G | — | — | XIX | — |
|   | C | — | — | — | — |
|   | T | XIIILys | — | — | — |

The modified analogous DNA random sequence shown above was synthesized using a DNA synthesizer (Applied 391A: tradename). In the modified analogous DNA random sequence, a, g, c and t amidites shown below were used for the parts of "a", "g", "c" and "t" and g amidite or c amidite shown below was used for the parts of "G/C", while a mixture dimer amidite of five different types shown in Table 1 above was used for the part of "NpNp".

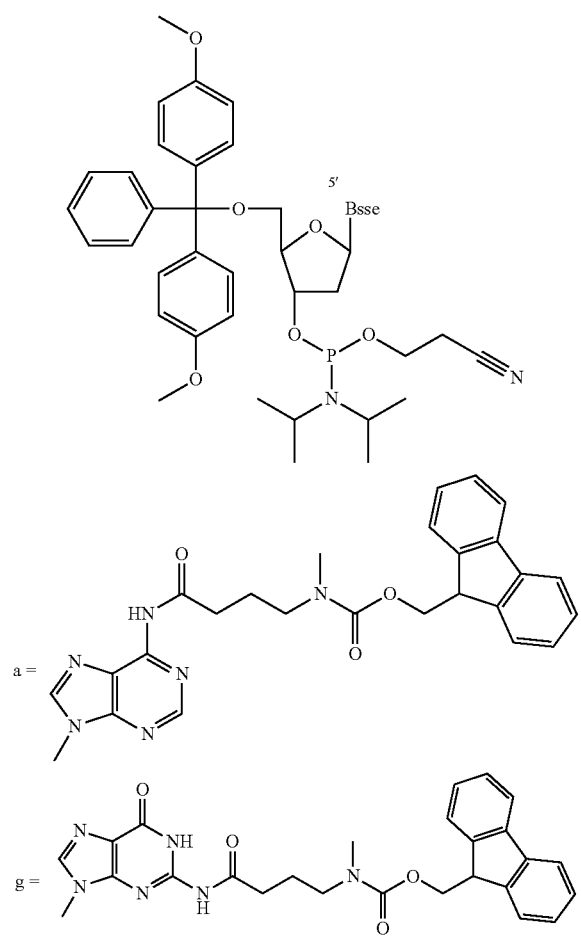

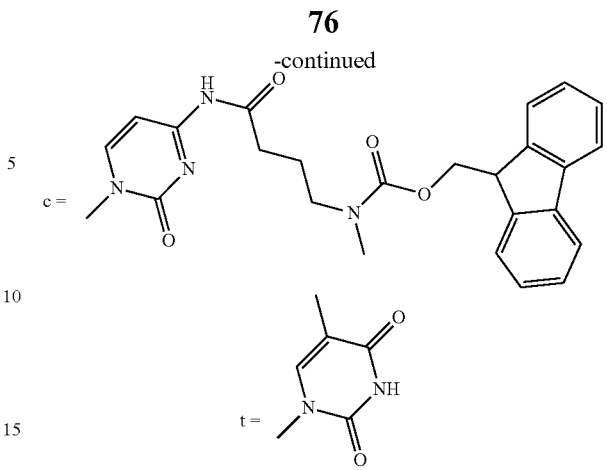

Deprotection (removal of protective group) was conducted for the synthesized modified analogous DNA random sequence mix (random pool of functional molecules) by feeding 0.01M diazabicycloundecene (DBU) in acetonitrile in the pool, and the sequence was cut out from the solid carrier using an aqueous solution of 0.1M DTT.

A GFP coupled resin was prepared by moisturizing a GFP solution having a biotination-modified terminal and an enterokinase cleavage site with avidin resin and by washing it. Then, 200 μL of 50 nmol of the above modified analogous DNA random sequence mix (random pool of functional molecules) was incubated with the resin at room temperature overnight to produce modified analogous DNA (functional molecule)-GFP-streptoavidin-biotin modified resin, which was then washed with 1 mL of 50 mM NaCl, 1 mM MgCl$_2$ and 0.05% Tween-20 and 10 mM Tris-HCl pH=8.5 for ten times or more at 50° C. After washing, it was confirmed by quantitative PCR that the modified analogous DNA (functional molecules) no longer existed.

Then, enterokinase was made to act on the resin and the occurrence of GFP flow was confirmed using fluorescence. An ammonia treatment was conducted by using a solution containing GFP, adding ammonia water and heating the solution. Subsequently, the ammonia was removed by reducing pressure.

PCR was conducted using TTATCAACAAAATACTC-CAATTG (Sequence ID No. 5) and CTTTTCGTTGG-GATCTTTC (Sequence ID No. 6) as primers for DNA amplification. The reaction product was then electrophoresed, purified and amplified by PCR. The PCR product was cloned by means of a known established method and 100 clones were sequenced. In a conventional method, only about 1% of clones have intermittent fixed sequences and satisfy the requirements of the dimer coding rules, and those sequences were examined elaborately. However, with the method for this Example (the target substance analysis method according to the present invention), 90% or more of the clones have intermittent fixed sequences and satisfy the requirements of the dimer coding rules. In other words, it was found that more than 90% of the clones can be decoded (translated, decrypted). After decoding (translating, or decrypting) by referring to a predefined dimer code correspondence table (Table 1), a modified analogous DNA was synthesized (replicated) using a DNA synthesizer and the association/dissociation constant for GFP was determined for each clone. As a result, it was confirmed that 20 clones had a Kd value of $10^{-7}$ or less.

From the above results, it was proved that, after screening a functional molecule having affinity for a target substance and subjecting it to an ammonia treatment to remove its substituents, it can be amplified with ease by PCR and that thereby the target substance can be analyzed efficiently by means of a target substance analysis method using the functional molecule according to the present invention (the target substance analysis method according to the present invention).

The functional molecule, functional molecule synthesizing amidite, and target substance analysis method according to the present invention are suitably used in a variety of fields including drugs, drug delivery and biosensors, as well as in controlling of gene expression level, overcoming diseases caused by abnormal genes, elucidation of the function of a protein translated from gene and development of reaction catalysts, and is particularly suitable for protein analysis.

What is claimed is:

1. A functional molecule synthesizing amidite expressed by General Formula (I) below and used for the manufacture of a functional molecule, where X represents a base, Y represents a substituent and Q represents one of a hydrogen atom and a hydroxyl group;

wherein the substituent Y is introduced to the base X through an aromatic carboxylic acid structure in the substituent Y, and the base X is one of adenine and cytosine; or the substituent Y is introduced to the base X through an aliphatic carboxylic acid structure in the substituent Y, and the base X is guanine, wherein the substituent Y can be removed by at least one method selected from the group consisting of a method involving an ammonia treatment, a method involving an alkali treatment using NaOH, a method involving a treatment using hydrofluoric acid and fluoride, a method involving a treatment using hydrazine, and a method involving irradiation of light, and wherein the functional molecule is convertible to be a molecule having a structure similar to that of naturally occurring nucleic acid by removing the substituent Y from the functional molecule;

General Formula (I)

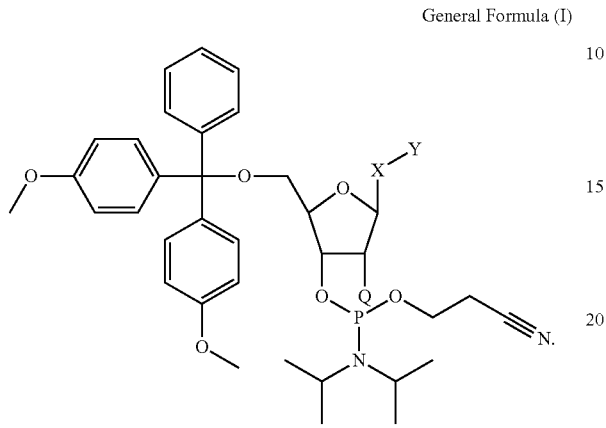

2. The functional molecule synthesizing amidite according to claim 1, wherein the substituent Y can be removed by at least one method selected from the group consisting of a method involving an ammonia treatment, a method involving an alkali treatment using NaOH, a method involving a treatment using hydrofluoric acid and fluoride, a method involving a treatment using hydrazine, and a method involving irradiation of light, but cannot be removed by DBU treatment in acetonitrile.

3. The functional molecule synthesizing amidite according to claim 1, wherein the amidite is expressed by General Formula (II) below in which the substituent Y is additionally protected by a protection group Z, where X represents a base, Y represents a substituent, Z represents a protection group and Q represents one of a hydrogen atom and hydroxyl group;

wherein the substituent Y is introduced to the base X through an aromatic carboxylic acid structure in the substituent Y, and the base X is one of adenine and cytosine; or the substituent Y is introduced to the base X through an aliphatic carboxylic acid structure in the substituent Y, and the base X is guanine, wherein the substituent Y can be removed by at least one method selected from the group consisting of a method involving an ammonia treatment, a method involving an alkali treatment using NaOH, a method involving a treatment using hydrofluoric acid and fluoride, a method involving a treatment using hydrazine, and a method involving irradiation of light, and wherein the functional molecule is convertible to be a molecule having a structure similar to that of naturally occurring nucleic acid by removing the substituent Y from the functional molecule;

General Formula (II)

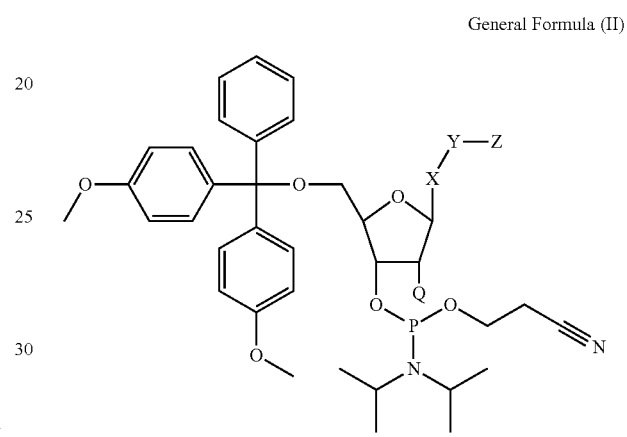

4. The functional molecule synthesizing amidite according to claim 3, wherein the protection group Z can be removed under conditions where the substituent Y is not removed.

5. The functional molecule synthesizing amidite according to claim 3, wherein the protection group Z can be removed by DBU treatment in acetonitrile.

* * * * *